(12) United States Patent
Ronsch et al.

US010358370B2

(10) Patent No.: US 10,358,370 B2
(45) Date of Patent: Jul. 23, 2019

(54) METHODS OF PROCESSING MUNICIPAL SOLID WASTE (MSW) USING MICROBIAL HYDROLYSIS AND FERMENTATION

(71) Applicant: Renescience A/S, Fredericia (DK)

(72) Inventors: Georg Ornskov Ronsch, Vejen (DK); Jacob Wagner Jensen, Egtved (DK); Sebastian Buch Antonsen, Horsens (DK)

(73) Assignee: RENESCIENCE A/S, Fredericia (DK)

( * ) Notice: Subject to any disclaimer, the term of this patent is extended or adjusted under 35 U.S.C. 154(b) by 0 days.

(21) Appl. No.: 14/897,963

(22) PCT Filed: Dec. 18, 2013

(86) PCT No.: PCT/DK2013/050443
§ 371 (c)(1),
(2) Date: Dec. 11, 2015

(87) PCT Pub. No.: WO2014/198274
PCT Pub. Date: Dec. 18, 2014

(65) Prior Publication Data
US 2016/0115063 A1 Apr. 28, 2016

(30) Foreign Application Priority Data
Jun. 12, 2013 (WO) ................ PCT/DK2013/050193
Jun. 12, 2013 (WO) ................ PCT/DK2013/050194

(51) Int. Cl.
| | |
|---|---|
| C02F 11/04 | (2006.01) |
| C02F 3/34 | (2006.01) |
| B09B 3/00 | (2006.01) |
| B09B 5/00 | (2006.01) |
| C12P 5/02 | (2006.01) |
| C12P 7/08 | (2006.01) |
| C12P 7/56 | (2006.01) |
| C12R 1/225 | (2006.01) |
| C12R 1/245 | (2006.01) |
| C12R 1/23 | (2006.01) |
| C12R 1/24 | (2006.01) |
| C12R 1/25 | (2006.01) |
| C12R 1/07 | (2006.01) |
| C12R 1/125 | (2006.01) |
| C12R 1/08 | (2006.01) |
| C12R 1/10 | (2006.01) |
| C12R 1/01 | (2006.01) |
| C12R 1/04 | (2006.01) |

(52) U.S. Cl.
CPC .............. *C02F 11/04* (2013.01); *B09B 3/00* (2013.01); *B09B 5/00* (2013.01); *C02F 3/342* (2013.01); *C12P 5/023* (2013.01); *C12P 7/08* (2013.01); *C12P 7/56* (2013.01); *C12R 1/01* (2013.01); *C12R 1/04* (2013.01); *C12R 1/07* (2013.01); *C12R 1/08* (2013.01); *C12R 1/10*
(2013.01); *C12R 1/125* (2013.01); *C12R 1/225* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 5,506,123 A * | 4/1996 | Chieffalo | ................ B03B 9/06 435/262 |
| 2007/0031918 A1 | 2/2007 | Dunson, Jr. et al. | |
| 2010/0086981 A1 | 4/2010 | Latouf et al. | |
| 2010/0319424 A1 * | 12/2010 | Wietgrefe | ................ C12P 7/10 71/23 |
| 2011/0165639 A1 * | 7/2011 | Ascon | ................ C12M 21/12 435/134 |
| 2012/0129229 A1 * | 5/2012 | McBride | ................ C12P 7/10 435/105 |

FOREIGN PATENT DOCUMENTS

| | | |
|---|---|---|
| AU | 2010206047 A1 | 8/2010 |
| CN | 1843152 A | 10/2006 |

(Continued)

OTHER PUBLICATIONS tenBrummeler, E. et al. 1991. Dry anaerobic batch digestion of the organic fraction of municipal solid waste. Journal of Chemical Technology and Biotechnology 50: 191-209. specif. pp. 191, 192, 193, 194, 195, 196, 199, 202.*
John, R.P. et al. 2007. Statistical optimization of simultaneous saccharification and L(+)—lactic acid fermentation from cassava bagasse using mixed culture of lactobacilli by response surface methodology. Biochemical Engineering Journal 36: 262-267. specif. p. 2007.*

(Continued)

*Primary Examiner* — Renee Claytor
*Assistant Examiner* — Sharon M. Papciak
(74) *Attorney, Agent, or Firm* — Womble Bond Dickinson (US) LLP

(57) ABSTRACT

The invention provides a method of processing MSW comprising the steps of —providing a stream of unsorted MSW to a microbial fermentation reactor in which the MSW is fermented with agitation at a non-water content of between 10 and 50% by weight and at a temperature of between 35 and 75 degrees for a period of between 1 and 72 hours under conditions sufficient to maintain a live lactic acid bacteria concentration of at least 10.000.000.000 CFU/L, and —removing a stream of fermented unsorted MSW from the reactor and subjecting it to a separation step whereby non-degradable solids are removed to provide a slurry of bio-degradable components. Further, a slurry of bio-degradable components prepared according to said method is provided.

14 Claims, 16 Drawing Sheets

(56) References Cited

FOREIGN PATENT DOCUMENTS

| | | |
|---|---|---|
| CN | 101003819 A | 7/2007 |
| CN | 101544990 A | 9/2009 |
| DE | 10 2009 00998 | 8/2010 |
| KR | 10-2010-0095994 A | 9/2010 |
| WO | WO 96/17949 A1 | 6/1996 |
| WO | WO 97/27158 A1 | 7/1997 |
| WO | WO 2006/029971 A2 | 3/2006 |
| WO | WO 2007/036795 A1 | 4/2007 |
| WO | WO 2009/003167 A1 | 12/2008 |
| WO | WO 2009/045653 A2 | 4/2009 |
| WO | WO 2011/100272 A1 | 8/2011 |
| WO | WO 2011/112737 A2 | 9/2011 |
| WO | WO 2013/185777 A1 | 12/2013 |
| WO | WO 2013/185778 A1 | 12/2013 |

OTHER PUBLICATIONS

Hawkes, F.R. et al. 2002. Sustainable fermentative hydrogen production: challenges for process optimisation. International Journal of Hydrogen Energy 27: 1339-1347. specif. pp. 1339, 1340, 1341, 1342.*

International Search Report and Written Opinion for corresponding International Application No. PCT/DK2013/050194, dated Oct. 29, 2013.

International Search Report and Written Opinion for International Application No. PCT/DK2013/050193, dated Oct. 29, 2013.

International Search Report and Written Opinion for International Application No. PCT/DK2013/050443, dated Mar. 26, 2014.

Ballesteros, M., et al., "Ethanol Production from the Organic Fraction Obtained After Thermal Pretreatment of Municipal Solid Waste," *Appl. BioChem. Biotechnol.*, 2010, pp. 423-431, vol. 161.

Consonni, S., et al., "Alternative Strategies for Energy Recovery from Municipal Solid Waste Part A: Mass and Energy Balances," *Waste Management*, 2005, pp. 123-135, vol. 25(2).

Fdez.-Güelfo, L. A. et al., "The Use of Thermochemical and Biological Pretreatments to Enhance Organic Matter Hydrolysis and Solubilization from Organic Fraction of Municipal Solid Waste (OFMSW)," *Chemical Engineering Journal*, 2011, pp. 249-254, vol. 168(1).

Fdez.-Güelfo, L. A., et al., "Biological Pretreatment Applied to Industrial Organic Fraction of Municipal Solid Waste (OFMSW): Effect on Anaerobic Digestion," *Chemical Engineering Journal*, 2011, pp. 321-325, vol. 172(1).

Hartmann, H., and B. K. Ahring, "Strategies for the Anaerobic Digestion of the Organic Fraction of Municipal Solid Waste: An Overview," *Water Science & Technology*, 2006, pp. 7-22, vol. 53(8).

Jensen, J. W., et al., "Enzymatic Processing of Municipal Solid Waste," *Waste Management*, 2010, pp. 2497-2503, vol. 30(12).

Jensen, J. W., et al., "Cellulase Hydrolysis of Unsorted MSW," *Appl. Biochem. Biotechnol.*, 2011, pp. 1799-1811, vol. 165.

Morita, M., and K. Sasaki, "Factors Influencing the Degradation of Garbage in Methanogenic Bioreactors and Impacts on Biogas Formation," *Applied Microbiol Biotechnol*, 2012, pp. 575-582, vol. 94(3).

Sasaki, D., et al., "Acceleration of Cellulose Degradation and Shift of Product via Methanogenic Co-culture of a Cellulolytic Bacterium with a Hydrogenotrophic Methanogen," *Journal of Bioscience and Bioengineering*, 2012, pp. 435-439, vol. 114(4).

Schmit, K. H., and T. G. Ellis, "Comparison of Temperature-Phased and Two-Phase Anaerobic Co-Digestion of Primary Sludge and Municipal Solid Waste," *Water Environment Research*, 2001, pp. 314-321, vol. 73(3).

Stehlík, P., "Contribution to Advances in Waste-to-Energy Technologies," *Journal of Cleaner Production*, 2009, pp. 919-931, vol. 17(10).

Tonini, D., and T. Astrup, "Life-Cycle Assessment of a Waste Refinery Process for Enzymatic Treatment of Municipal Solid Waste," *Waste Management*, 2012, pp. 165-176, vol. 32(1).

Yu, L., et al., "Experimental and Modeling Study of a Two-Stage Pilot Scale High Solid Anaerobic Digester System," *Bioresource Technology*, 2012, pp. 8-17, vol. 124.

Zhang, B., et al., "Extracellular Enzyme Activities During Regulated Hydrolysis of High-Solid Organic Wastes," *Water Research*, 2007, pp. 4468-4478, vol. 41(19).

Zverlov, V., et al., "Hydrolytic Bacteria in Mesophilic and Thermophilic Degradation of Plant Biomass," *Eng. Life Sci.*, 2010, pp. 528-536, vol. 10(6).

He, R., et al., "Biological degradation of MSW in a methanogenic reactor using treated lechate recirculation," *Process Biochemistry*, 2005, vol. 40, pp. 3660-3666.

Pipyn, P., et anon., "Lactate and Ethanol as Intermediates in Two-Phase Anaerobic Digestion," *Biotechnology and Bioengineering*, 1981, vol. XXIII, pp. 1145-1154.

* cited by examiner

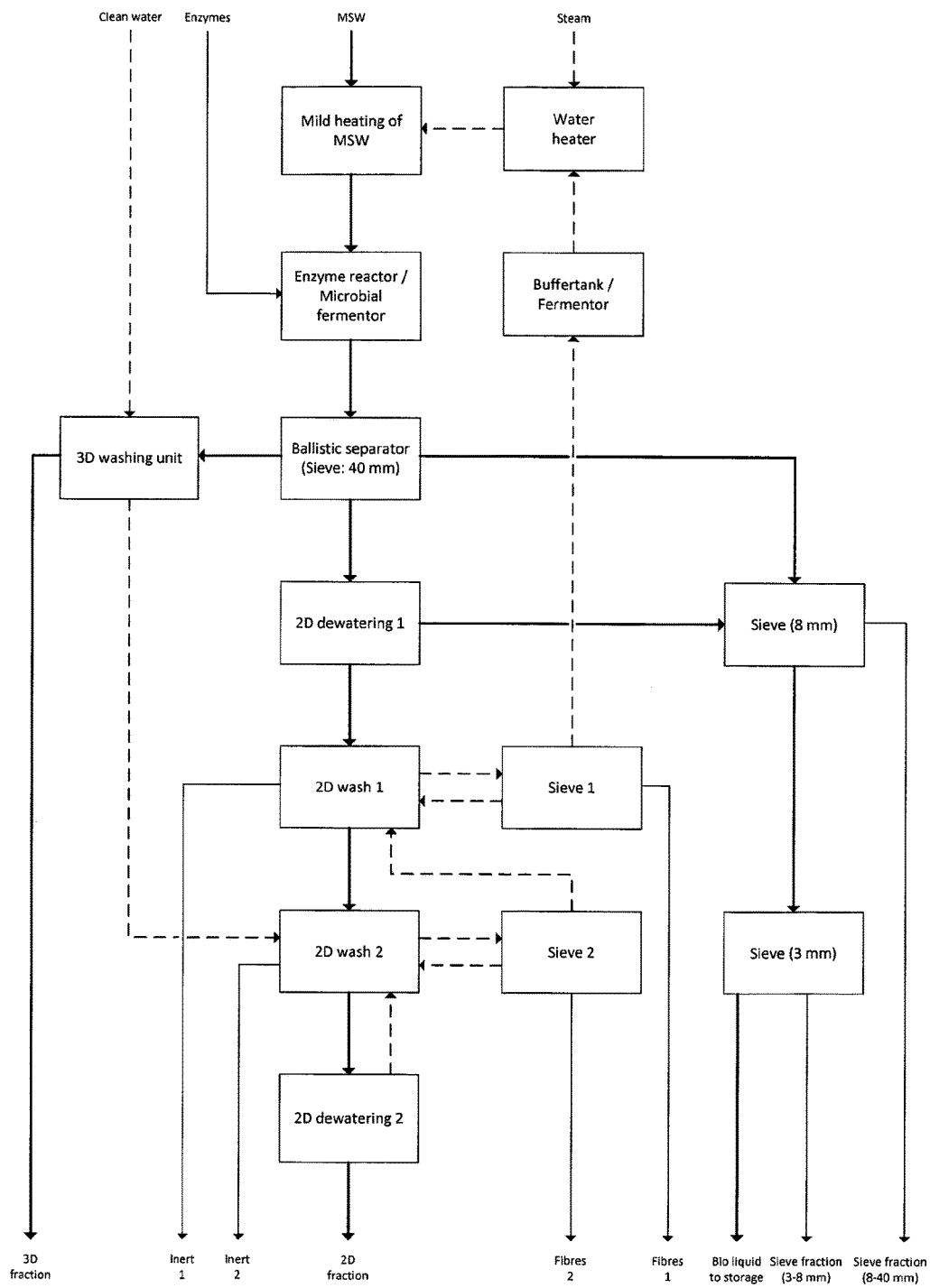
Figure 1. Schematic illustration of principle features of the demonstration plant

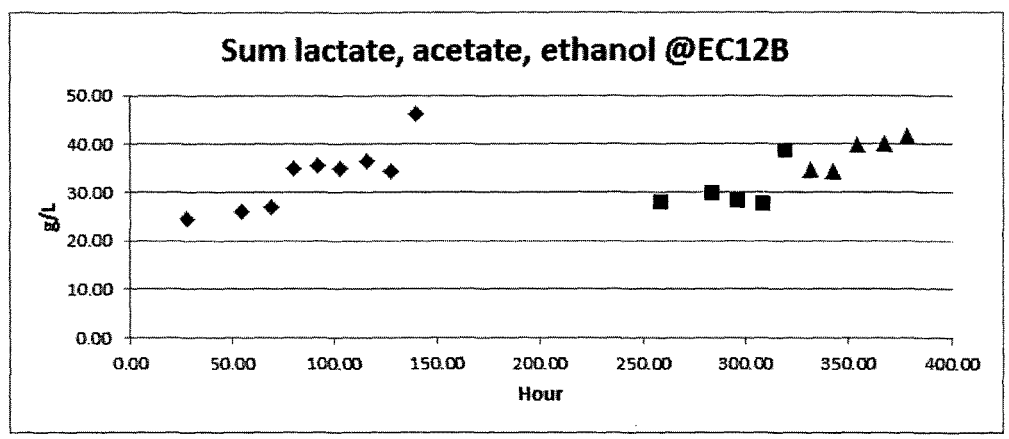
Figure 2: Sum of lactate, acetate and ethanol concentration in the biogenic slurry obtained with and without supplemental cellulase activity provided by isolated enzyme preparations.

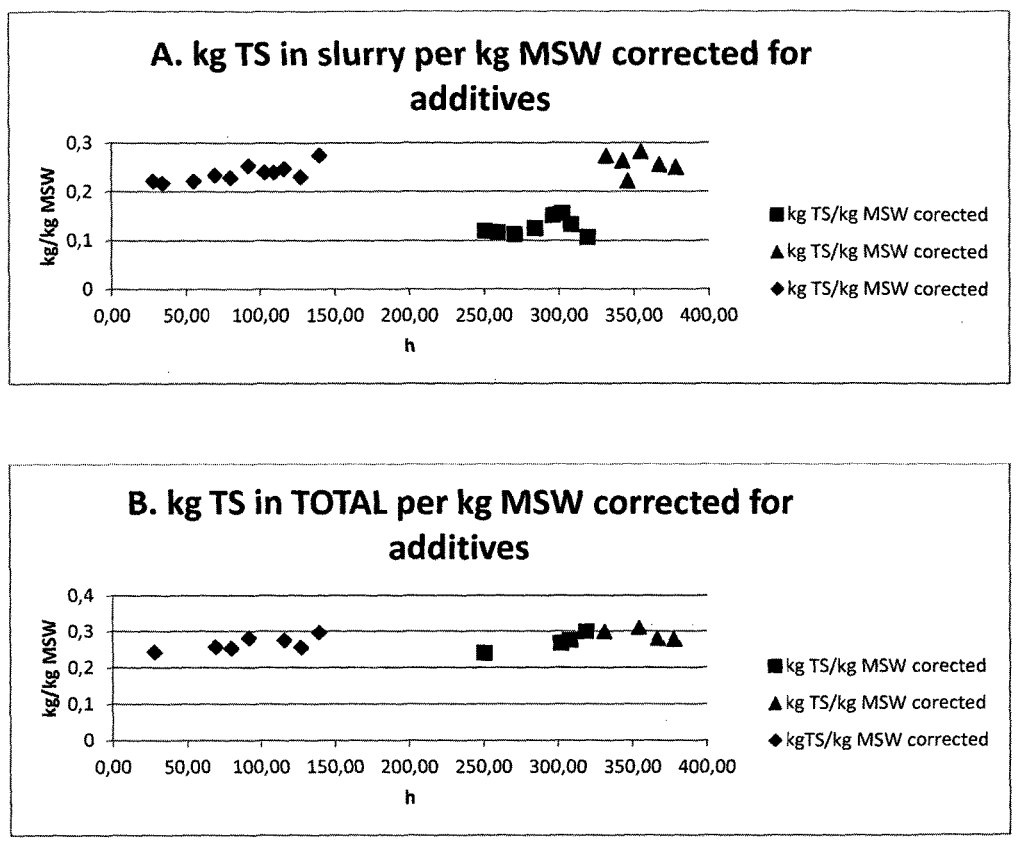
Figure 3. Bio-degradable capture in kg TS/ kg waste. (A). In biogenic slurry after 3 mm sieves. (B) Total capture including material retained by sieves.

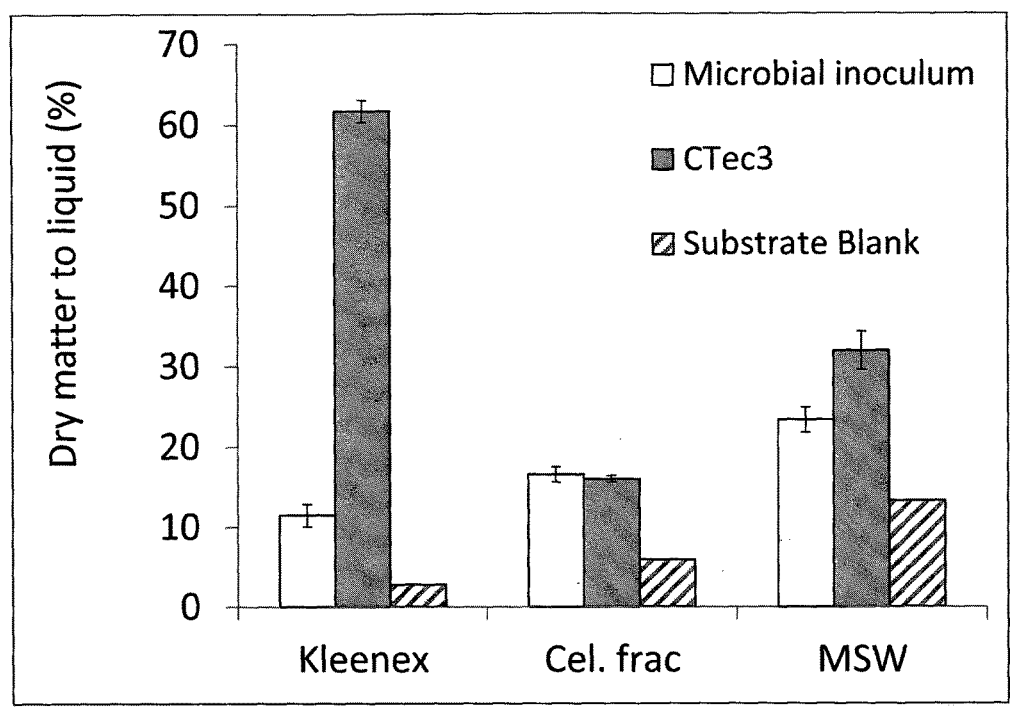
Figure 4 Degradation of cellulosic substrates and model MSW by microbial inoculum and CTEC3.

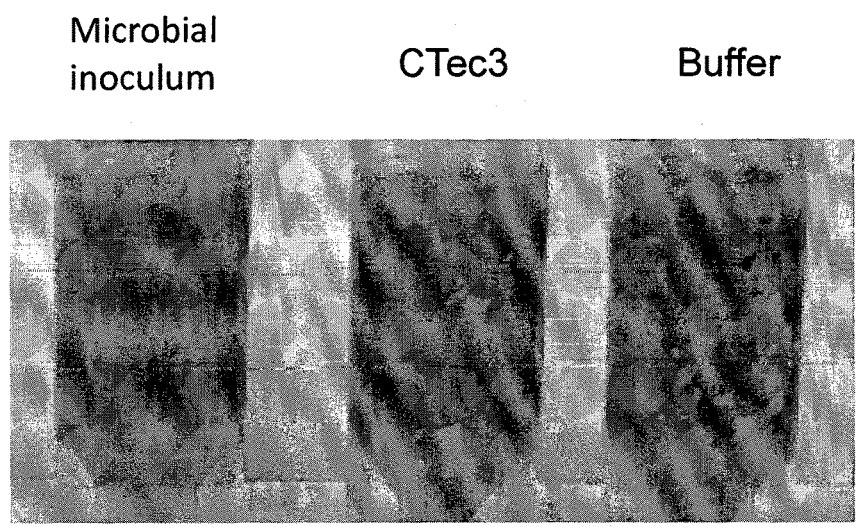
Figure 5. Comparative degradation of cellulosic fraction of model MSW by microbial inoculum and CTEC3.

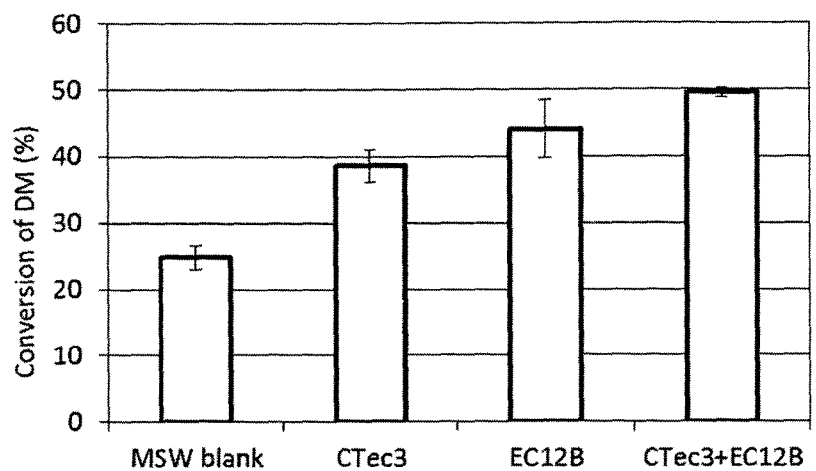
Figure 6. Conversion of dry matter in concurrent enzymatic hydrolysis with CTEC3 and microbial fermentation.

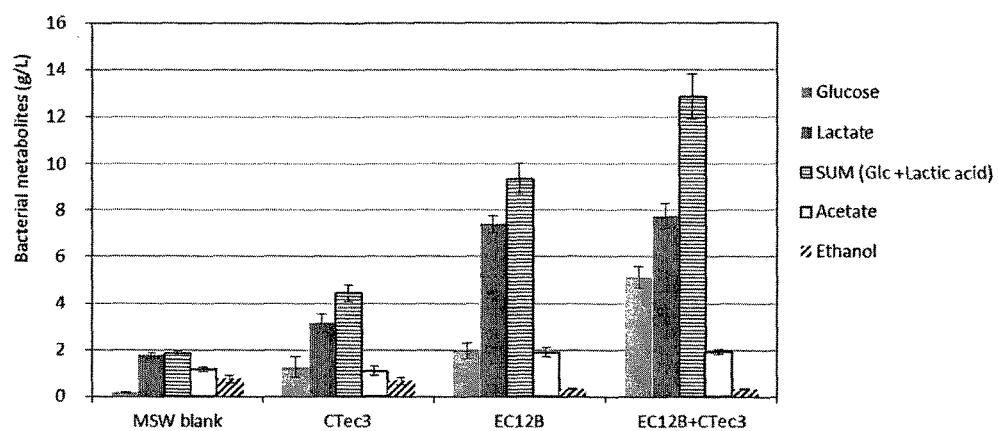
Figure 7. Bacterial metabolites recovered in supernatant following concurrent enzymatic hydrolysis with CTEC3 and microbial fermentation.

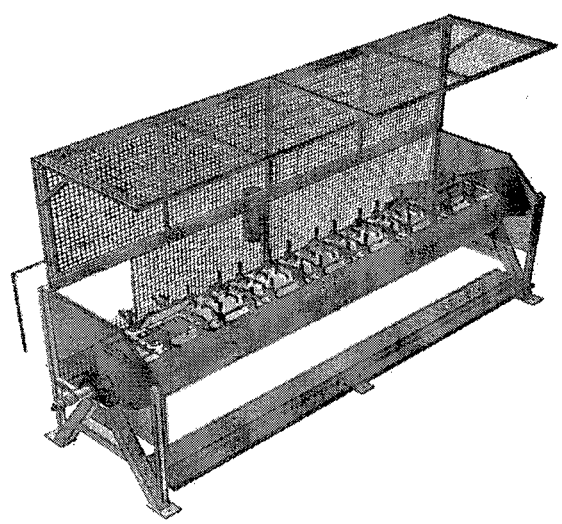
Figure 8. Graphical presentation of the REnescience test-reactor.

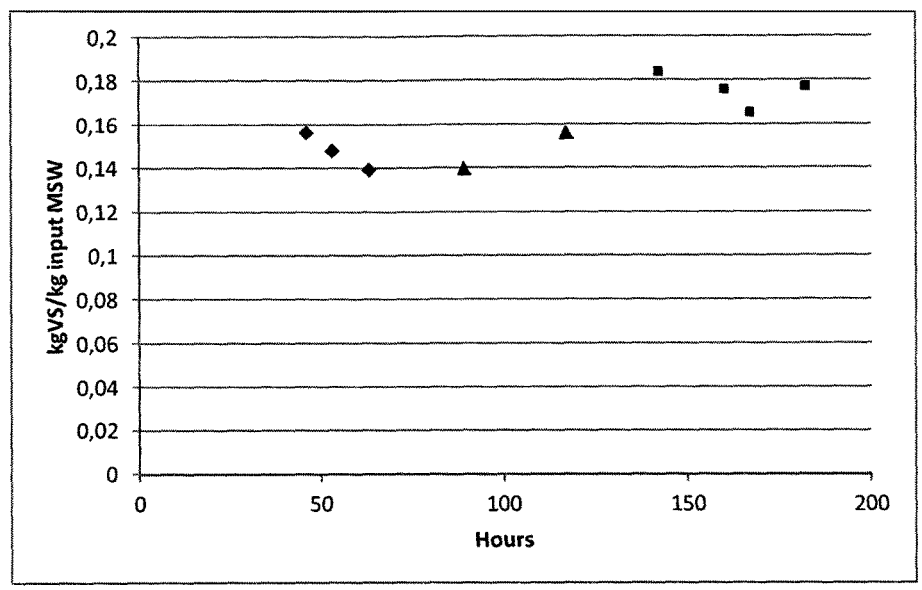
Figure 9. Bio-degradable capture in biogenic slurry during different time periods expressed as kg VS per kg MSW processed.

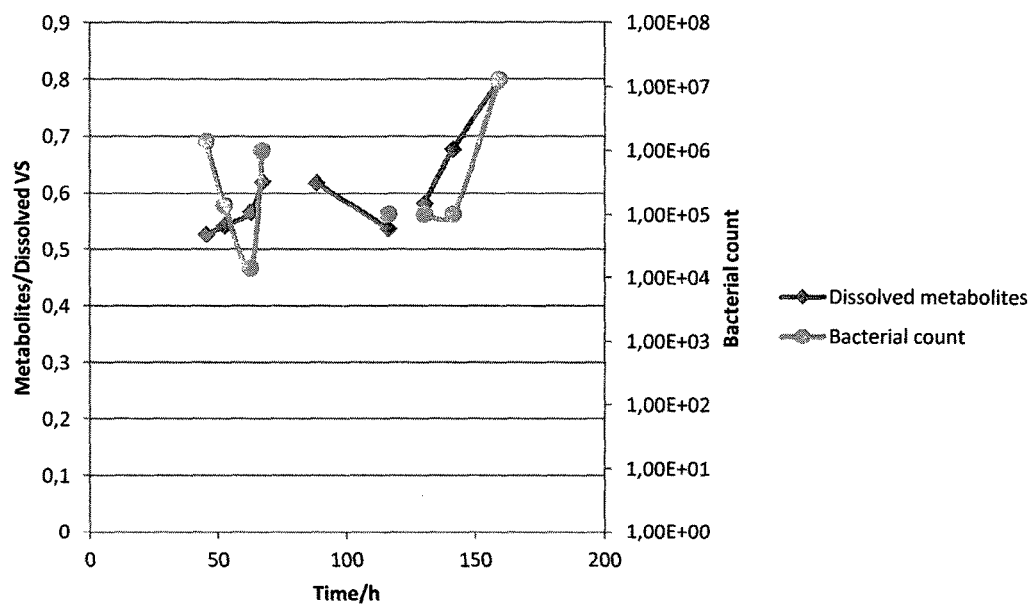
Figure 10. Bacterial metabolites in biogenic slurry and aerobic bacterial counts at different time points.

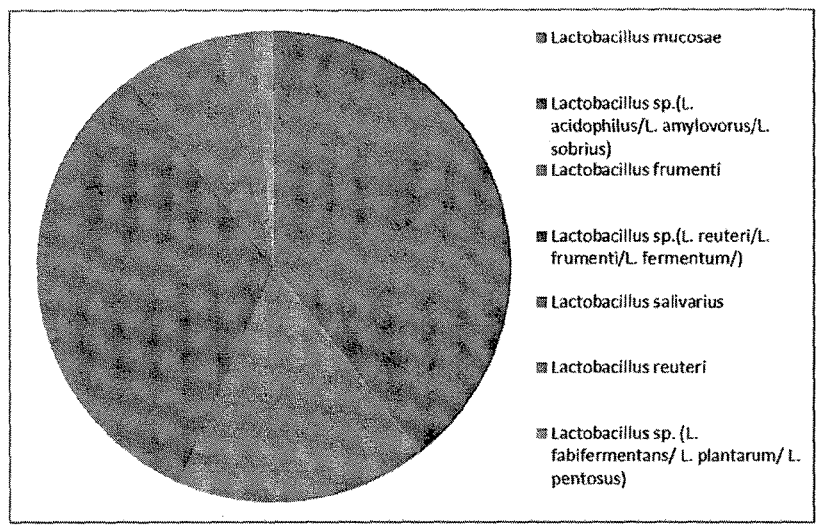
Figure 11. Distribution of bacterial species identified in biogenic slurry from example 7.

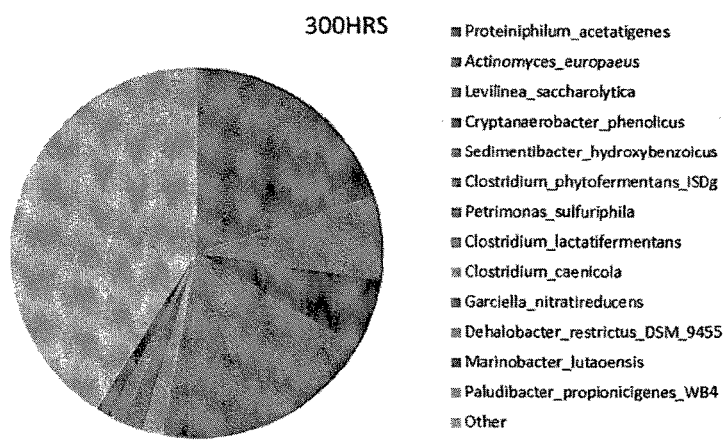
Figure 12. Distribution of the 13 predominant bacteria in biogenic slurry from example 9.

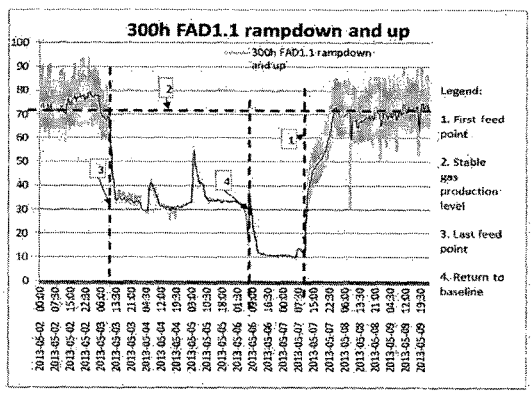
Figure 13. Biomethane production ramp-up and ramp-down using biogenic slurry from example 9.

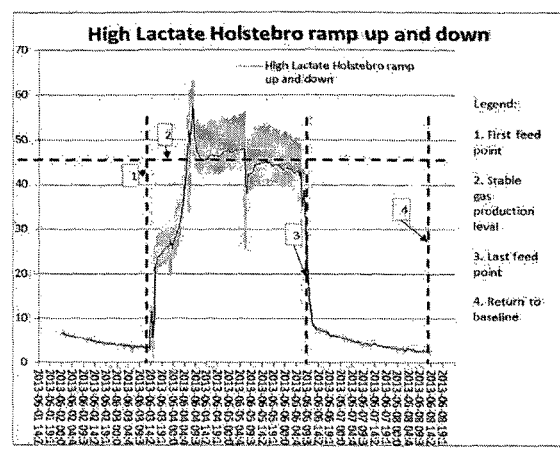
Figure 14. Biomethane production ramp-up and ramp-down characterization of the "high lactate" bioliquid from example 6.

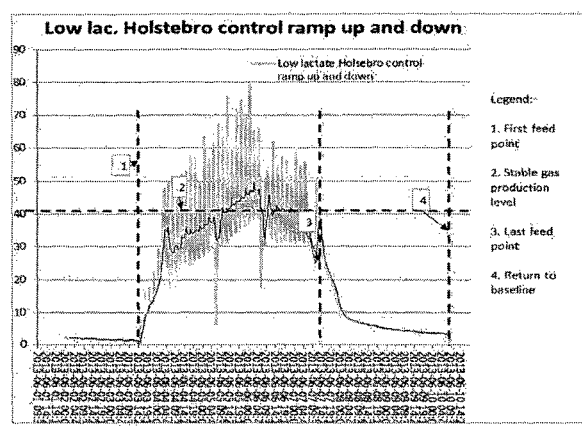
Figure 15. Biomethane production ramp-up and ramp-down characterization of the "low lactate" bioliquid from example 6.

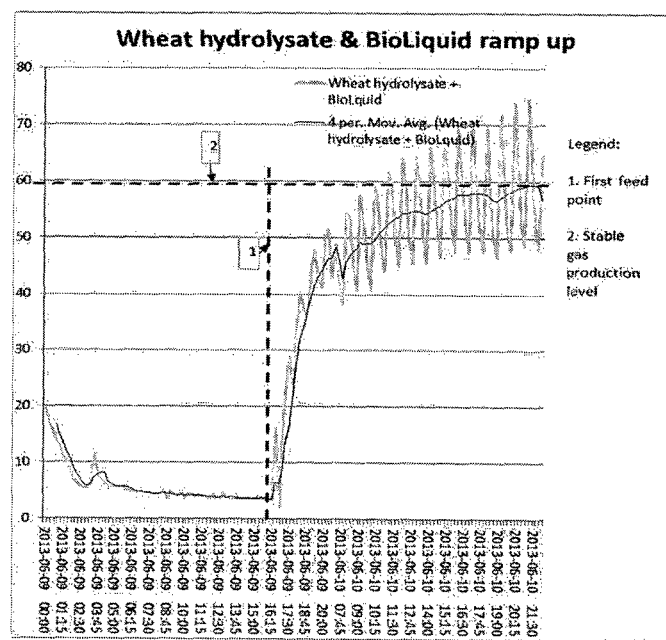
Figure 16. Biomethane production ramp-up characterization of the hydrolysed wheat straw bioliquid.

METHODS OF PROCESSING MUNICIPAL SOLID WASTE (MSW) USING MICROBIAL HYDROLYSIS AND FERMENTATION

CROSS-REFERENCE TO RELATED APPLICATIONS

This application is a national stage filing under 35 U.S.C. 371 of PCT/DK2013/050443 filed Dec. 18, 2013, which International Application was published by the International Bureau in English on Dec. 18, 2014, and application claims priority from International Application No. PCT/DK2013/050193, filed Jun. 12, 2013, and International Application No. PCT/DK2013/050194, filed Jun. 12, 2013, which applications are hereby incorporated in their entirety by reference in this application.

FIELD

The invention relates in general to methods of processing solid wastes, and in particular to methods that rely on microbial fermentation.

Municipal solid wastes (MSW), particularly including domestic household wastes, wastes from restaurants and food processing facilities, and wastes from office buildings comprise a very large component of organic material that can be further processed to energy, fuels and other useful products. At present only a small fraction of available MSW is recycled, the great majority being dumped into landfills.

Considerable interest has arisen in development of efficient and environmentally friendly methods of processing solid wastes, to maximize recovery of their inherent energy potential and, also, recovery of recyclable materials. One significant challenge in "waste to energy" processing has been the heterogeneous nature of MSW. Solid wastes typically comprise a considerable component of organic, degradable material intermingled with plastics, glass, metals and other non-degradable materials. Unsorted wastes can be directly used in incineration, as is widely practiced in countries such as Denmark and Sweden, which rely on district heating systems. See Strehlik 2009. However, incineration methods are associated with negative environmental consequences and do not accomplish effective recycling of raw materials. Clean and efficient use of the degradable component of MSW combined with recycling typically requires some method of sorting to separate degradable from non-degradable material.

The degradable component of MSW can be used in "waste to energy" processing using both thermo-chemical and biological methods. MSW can be subject to pyrolysis or other modes of thermo-chemical gasification. Organic wastes thermally decomposed at extreme high temperatures, produce volatile components such as tar and methane as well as a solid residue or "coke" that can be burned with less toxic consequences than those associated with direct incineration. Alternatively, organic wastes can be thermally converted to "syngas," comprising carbon monoxide, carbon dioxide and hydrogen, which can be further converted to synthetic fuels. See e.g. Malkow 2004 for review.

Biological methods for conversion of degradable components of MSW include fermentation to produce specific useful end products, such as ethanol. See e.g. WO2009/150455; WO2009/095693; WO2007/036795; Ballesteros et al. 2010; Li et al 2007.

Alternatively, biological conversion can be achieved by anaerobic digestion to produce biomethane or "biogas." See e.g. Hartmann and Ahring 2006 for review. Pre-sorted organic component of MSW can be converted to biomethane directly, see e.g. US2004/0191755, or after a comparatively simple "pulping" process involving mincing in the presence of added water, see e.g. US2008/0020456.

However, pre-sorting of MSW to obtain the organic component is typically costly, inefficient or impractical. Source-sorting requires large infrastructure and operating expenses as well as the active participation and support from the community from which wastes are collected—an activity which has proved difficult to achieve in modern urban societies. Mechanical sorting is typically capital intensive and further associated with a large loss of organic material, on the order of at least 30% and often much higher. See e.g. Connsonni 2005.

Some of these problems with sorting systems have been successfully avoided through use of liquefaction of organic, degradable components in unsorted waste. Liquefied organic material can be readily separated from non-degradable materials. Once liquefied into a pumpable slurry, organic component can be readily used in thermo-chemical or biological conversion processes. Liquefaction of degradable components has been widely reported using high pressure, high temperature "autoclave" processes, see e.g. US2013/0029394; US2012/006089; US20110008865; WO2009/150455; WO2009/108761; WO2008/081028; US2005/0166812; US2004/0041301; U.S. Pat. No. 5,427,650; U.S. Pat. No. 5,190,226.

A radically different approach to liquefaction of degradable organic components is that this may achieved using biological process, specifically through enzymatic hydrolysis, see Jensen et al. 2010; Jensen et al. 2011; Tonini and Astrup 2012; WO2007/036795; WO2010/032557.

Enzymatic hydrolysis offers unique advantages over "autoclave" methods for liquefaction of degradable organic components. Using enzymatic liquefaction, MSW processing can be conducted in a continuous manner, using comparatively cheap equipment and non-pressurized reactions run at comparatively low temperatures. In contrast, "autoclave" processes must be conducted in batch mode and generally involve much higher capital costs.

A perceived need for "sterilization" so as to reduce possible health risks posed by MSW-bourne pathogenic microorganisms has been a prevailing theme in support of the predominance of "autoclave" liquefaction methods. See e.g. WO2009/150455; WO2000/072987; Li et al. 2012; Ballesteros et al. 2010; Li et al. 2007. Similarly, it was previously believed that enzymatic liquefaction required thermal pre-treatment to a comparatively high temperature of at least 90-95° C. This high temperature was considered essential, in part to effect a "sterilization" of unsorted MSW and also so that degradable organic components could be softened and paper products "pulped." See Jensen et al. 2010; Jensen et al. 2011; Tonini and Astrup 2012.

We have discovered that safe enzymatic liquefaction of unsorted MSW using isolated cellulase preparations can be achieved without high temperature pre-treatment. Indeed, contrary to expectations, high temperature pre-treatment is not only unnecessary, but can be actively detrimental, since this kills ambient microorganisms which are thriving in the waste. Promoting microbial fermentation concurrently with cellulase hydrolysis at thermophilic conditions typically between 40 and 55° C. improves "bio-degradable capture," either using "ambient" microorganisms or using selectively "inoculated" organisms. That is, concurrent thermophilic microbial fermentation safely increases the yield of "bio-degradable slurry" that is recovered. Under these conditions, pathogenic microorganisms typically found in MSW do not thrive. See e.g. Hartmann and Ahring 2006; Deportes et al. 1998; Carrington et al. 1998; Bendixen et al. 1994; Kubler et al. 1994; Six and De Baerre et al. 1992. Under these conditions, typical MSW-bourne pathogens are easily outcompeted by ubiquitous lactic acid bacteria and other safe organisms.

In addition to improving "bio-degradable capture" from enzymatic hydrolysis using isolated cellulase preparations, concurrent microbial fermentation using any combination of lactic acid bacteria, or acetate-, ethanol-, formate-, butyrate-, lactate-, pentanoate- or hexanoate-producing microorganisms, "pre-conditions" the bio-degradable slurry so as to render it more efficient as a substrate for biomethane production. Microbial fermentation produces bio-degradable slurry having a generally increased percentage of dissolved compared with suspended solids, relative to bio-degradable slurry produced by enzymatic liquefaction using isolated cellulase preparations alone. Higher chain polysaccharides are generally more thoroughly degraded due to microbial "pre-conditioning." Concurrent microbial fermentation and enzymatic hydrolysis using isolated cellulase preparations degrades biopolymers into readily usable substrates and, further, achieves metabolic conversion of primary substrates to short chain carboxylic acids and/or ethanol. The resulting bio-degradable comprising a high percentage of microbial metabolites provides a biomethane substrate which effectively avoids the rate limiting "hydrolysis" step, see e.g. Delgenes et al. 2000; Angelidaki et al. 2006; Cysneiros et al. 2011, and which offers further advantages for methane production, particularly using very rapid "fixed filter" anaerobic digestion systems.

Surprisingly, sufficient liquefaction of degradable components of unsorted MSW prior to separation of non-degradable material can be achieved within a relatively short processing time, typically 36 hours or less, by microbial fermentation alone, without any requirement for isolated cellulase preparations. An improved "fast" biomethane substrate comprising a high degree of dissolved solids and bacterial metabolites can be achieved, even where the initial separation of non-degradable material is achieved by microbial fermentation alone, by the simple expedient of continued fermentation of the recovered bio-degradable slurry following the initial separation of non-degradable solids.

BRIEF DESCRIPTION OF THE FIGURES

FIG. 1. Schematic illustration of principle features of the demonstration plant.

FIG. 2: Sum of lactate, acetate and ethanol concentration in the biogenic slurry obtained with and without supplemental cellulase activity provided by isolated enzyme preparations.

FIG. 3. Bio-degradable capture in kg TS/kg affald. (A). In biogenic slurry after 3 mm sieves. (B) Total capture including material retained by sieves.

FIG. 4 Degradation of cellulosic substrates and model MSW by microbial inoculum and CTEC3.

FIG. 5. Comparative degradation of cellulosic fraction of model MSW by microbial inoculum and CTEC3.

FIG. 6. Conversion of dry matter in concurrent enzymatic hydrolysis with CTEC3 and microbial fermentation.

FIG. 7. Bacterial metabolites recovered in supernatant following concurrent enzymatic hydrolysis with CTEC3 and microbial fermentation.

FIG. 8. Graphical presentation of the REnescience test-reactor.

FIG. 9. Bio-degradable capture in biogenic slurry during different time periods expressed as kg VS per kg MSW processed.

FIG. 10. Bacterial metabolites in biogenic slurry and aerobic bacterial counts at different time points.

FIG. 11. Distribution of bacterial species identified in biogenic slurry from example 7.

FIG. 12. Distribution of the 13 predominant bacteria in biogenic slurry from example 9.

FIG. 13. Biomethane production ramp-up and ramp-down using biogenic slurry from example 9.

FIG. 14. Biomethane production ramp-up and ramp-down characterization of the "high lactate" bioliquid from example 6.

FIG. 15. Biomethane production ramp-up and ramp-down characterization of the "low lactate" bioliquid from example 6.

FIG. 16. Biomethane production ramp-up characterization of the hydrolysed wheat straw bioliquid.

DETAILED DESCRIPTION OF EMBODIMENTS

In some embodiments, the invention provides a method of processing MSW comprising the steps of
  providing a stream of unsorted MSW to a microbial fermentation reactor in which the MSW is fermented with agitation at a non-water content of between 10 and 50% by weight and at a temperature of between 35 and 75 degrees for a period of between 1 and 72 hours under conditions sufficient to maintain a live lactic acid bacteria concentration of at least $1.0 \times 10^{10}$ CFU/L, and
  removing a stream of fermented unsorted MSW from the reactor and subjecting it to a separation step whereby non-degradable solids are removed to provide a slurry of bio-degradable components.

Naturally occurring strains of Lactic Acid Bacteria (LAB) present in waste have been previously shown to provide effective conversion, to lactate, of model kitchen wastes comprising fruits, vegetables, grains, meat, fish and the like. See Sakai et al. 2000; Sakai et al. 2004; Akao et al. 2007a; Akao et al. 2007b. No particular inoculation procedure was required to produce an effective lactate fermentation of the wastes—these were simply minced in an equal volume of water, then heated to temperatures between 37 and 55° C. A community of naturally occurring strains typically emerged, with one or another species emerging as clearly dominant. See Sakai et al. 2004. However, in order to facilitate large scale processing, it is advantageous to keep fermentation times as short as practicable during the initial step prior to removal of non-degradable solids. Some degradation by microbially-derived enzyme activity should generally be achieved prior to the separation of non-degradable solids. Ideally, the bio-degradable component of the MSW is liquefied prior to the separation, meaning that a sufficient degradation has occurred such that the slurry of dissolved and undissolved solids is pumpable.

Where lactic acid fermentations have been conducted using substrates that include a large percentage of cellulosic and lignocellulosic materials, isolated cellulase enzyme preparations have typically been used to promote cellulase hydrolysis simultaneously with fermentation using lactic acid bacteria. See e.g. Abe and Takagi 1990; Parajo et al. 1997; Chen and Lee 1997; Schmidt and Padukone 1997. Yet many species of LAB, including almost every species of *Lactobaccillus* tested and many species of *Pediococcus* have been shown to exhibit extra-cellular cellulase activity. See e.g. Yang et al. 2001; Matthews et al. 2004; Matthews et al. 2006; Gao et al. 2008. Thus, it is possible to practice methods of the invention using a microbial fermentation comprising primarily or even solely LAB and nevertheless achieve effective levels of cellulase activity.

Any suitable solid waste may be used to practice methods of the invention. As will be understood by one skilled in the art, the term "municipal solid waste" (MSW) refers to waste fractions which are typically available in a city, but that need not come from any municipality per se. MSW can be any combination of cellulosic, plant, animal, plastic, metal, or glass waste including but not limited to any one or more of the following: Garbage collected in normal municipal collections systems, optionally processed in some central sorting, shredding or pulping device such Dewaster® or ReCulture®; solid waste sorted from households, including both organic fractions and paper rich fractions; waste fractions derived from industry such as restaurant industry, food processing industry, general industry; waste fractions from paper industry; waste fractions from recycling facilities; waste fractions from food or feed industry; waste fraction from the medicinal industry; waste fractions derived from agriculture or farming related sectors; waste fractions from processing of sugar or starch rich products; contaminated or in other ways spoiled agriculture products such as grain, potatoes and beets not exploitable for food or feed purposes; garden refuse.

MSW is by nature typically heterogeneous. Statistics concerning composition of waste materials are not widely known that provide firm basis for comparisons between countries. Standards and operating procedures for correct sampling and characterisation remain unstandardized. Indeed, only a few standardised sampling methods have been reported. See e.g. Riber et al., 2007. At least in the case of household waste, composition exhibits seasonal and geographical variation. See e.g. Dahlen et al., 2007; Hansen et al., 2007b; Muhle et al., 2010; Riber et al., 2009. Geographical variation in household waste composition has also been reported, even over small distances of 200-300 km between municipalities. See Hansen et al., 2007b. As a general rule, the dry weight of modern urban wastes from Western Europe typically comprise on the order of 25% by weight of "vegetable and food wastes" In China, in contrast, the relative proportions of "food wastes" are typically increased by a factor of at least two relative to MSW from Western Europe. See e.g. Zhang et al. 2010.

In some embodiments, MSW is processed as "unsorted" wastes. The term "unsorted" as used herein refers to a process in which MSW is not substantially fractionated into separate fractions such that biogenic material is not substantially separated from plastic and/or other non-biogenic material. As used herein the term "biogenic" refers to materials that are bio-degradable and comprise materials derived from living organisms. Wastes may be "unsorted" as used herein notwithstanding removal of some large objects or metal objects and notwithstanding some separation of plastic and/or other non-biogenic material. The terms "unsorted waste" (or "unsorted MSW") as used herein refers to waste comprising a mixture of biogenic and non-biogenic material in which 15% by weight or greater of the dry weight is non-biogenic material.

Typically unsorted MSW comprises biogenic wastes, including food and kitchen waste, paper- and/or cardboard-containing materials, food wastes and the like; recyclable materials, including glass, bottles, cans, metals, and certain plastics; other burnable materials, which while not practically recyclable per se may give heat value in the form of refuse derived fuels; as well as inert materials, including ceramics, rocks, and various forms of debris.

In some embodiments, MSW can be processed as "sorted" waste. The term "sorted" as used herein refers to a process in which MSW is substantially fractionated into separate fractions such that biogenic material is substantially separated from plastic and/or other non-biogenic material. The term "sorted waste" (or "sorted MSW") as used herein refers to waste in which less than 15% by weight of the dry weight is non-biogenic material.

In some embodiments, MSW can be source-separated organic waste comprising predominantly fruit, vegetable and/or animal wastes. A variety of different sorting systems can be applied to unsorted MSW in some embodiments, including source sorting, where households dispose of different waste materials separately. Source sorting systems are currently in place in some municipalities in Austria, Germany, Luxembourg, Sweden, Belgium, the Netherlands, Spain and Denmark. Alternatively industrial sorting systems can be used. Means of mechanical sorting and separation may include any methods known in the art including but not limited to the systems described in US2012/0305688; WO2004/101183; WO2004/101098; WO2001/052993; WO2000/0024531; WO1997/020643; WO1995/0003139; CA2563845; U.S. Pat. No. 5,465,847. In some embodiments, wastes may be lightly sorted yet still produce a waste fraction that is "unsorted" as used herein. In some embodiments, unsorted MSW is used in which greater than 15% by weight of the dry weight is non-biogenic material, or greater than 18%, or greater than 20%, or greater than 21%, or greater than 22%, or greater than 23%, or greater than 24%, or greater than 25%.

In practicing methods of the invention, water content of the MSW is adjusted so that the MSW comprises a non-water content of between 10 and 50% by weight, or in some embodiments between 12 and 40%, or between 13 and 35%, or between 14 and 30%, or between 15 and 25%. In some embodiments the water content is considered to be "adjusted" as used herein where the MSW comprises the appropriate non-water content, whether or not water has been directly added. MSW typically comprises considerable water content. All other solids comprising the MSW are termed "non-water content" as used herein. The level of water content used in practicing methods of the invention relates to several interrelated variables. Methods of the invention typically produce a biogenic slurry. As will be readily understood, the slurry is biogenic where it comprises predominantly biogenic material, but may also include non-biogenic contaminants. A slurry is "liquid" as used herein to the extent that it is pumpable, notwithstanding substantial content of undissolved solids.

As will be readily understood by one skilled in the art, the capacity to render solid components into a liquid slurry is increased with increased water content. Effective pulping of paper and cardboard, which comprise a substantial fraction of MSW in some countries, is typically improved where water content is increased. Water content provides a medium in which the microbial preparation can propagate and which dissolves metabolites. Further, as is well known in the art, enzyme activities can exhibit diminished activity when hydrolysis is conducted under conditions with low water content. For example, cellulases typically exhibit diminished activity in hydrolysis mixtures that have non-water content higher than about 10% by weight. In the case of cellulases, which degrade paper and cardboard, an effectively linear inverse relationship has been reported between substrate concentration and yield from the enzymatic reaction per gram substrate. See Kristensen et al. 2009.

In some embodiments, some water content should normally be added to the waste in order to achieve an appropriate non-water content. For example, consider a fraction of unsorted Danish household waste. Table 1, which describes characteristic composition of unsorted MSW reported by Riber et al. (2009), "Chemical composition of material fractions in Danish household waste," Waste Management 29:1251. Riber et al. characterized the component fractions of household wastes obtained from 2220 homes in Denmark on a single day in 2001. It will be readily understood by one skilled in the art that this reported composition is simply a representative example, useful in explaining methods of the invention. In the example shown in Table 1, without any addition of water content, the biogenic, bio-degradable fraction comprising vegetable, paper and animal waste would be expected to have approximately 47% non-water content on average. [(absolute % non-water)/(% wet weight) =(7.15+18.76+4.23)/(31.08+23.18+9.88)=47% non-water content.] Addition of a volume of water corresponding to one weight equivalent of the waste fraction being processed would reduce the non-water content of the waste itself to 29.1% (58.2%/2) while reducing the non-water content of the degradable component to about 23.5% (47%/2). Addition of a volume of water corresponding to two weight equivalents of the waste fraction being processed would reduce the non-water content of the waste itself to 19.4% (58.2%/3) while reducing the non-water content of the degradable component to about 15.7% (47%/3).

TABLE 1

Summarised mass distribution of waste fractions from Denmark 2001

| Waste fraction | Part of overall waste quantity % wet weight | Part of overall waste expressed as absolute contribution to total non water content of 58.2% |
| --- | --- | --- |
| Vegetable waste (a) | 31.08 | 7.15 |
| Paper waste (b) | 23.18 | 18.76 |
| Animal waste (a) | 9.88 | 4.23 |
| Plastic waste (c) | 9.17 | 8.43 |
| Diapers (a) | 6.59 | 3.59 |
| Non combustibles (d) | 4.05 | 3.45 |
| Metal (e) | 3.26 | 2.9 |
| Glass (f) | 2.91 | 2.71 |
| Other (g) | 9.88 | 6.98 |
| TOTAL | 100.00% | 58.20% |

(a) Pure fraction.
(b) Sum of: newspaper, magazines, advertisements, books, office and clean/dirty paper, paper and carton containers, cardboard, carton with plastic, carton with Al foil, dirty cardboard and kitchen tissues.
(c) Sum of: Soft plastic, plastic bottles, other hard plastic and non-recyclable plastic.
(d) Sum of: Soil, Rocks etc., ash, ceramics, cat litter and other non combustibles.
(e) Sum of: Al containers, al foil, metal-like foil, metal containers and other metal.
(f) Sum of: Clear, green, brown and other glass.
(g) Sum of: The remaining 13 material fractions.

One skilled in the art will readily be able to determine an appropriate quantity of water content, if any, to add to wastes in adjusting water content. Typically as a practical matter, notwithstanding some variability in the composition of MSW being processed, it is convenient to add a relatively constant mass ratio of water (which includes aqueous solution), in some embodiments between 0.8 and 1.8 kg water per kg MSW, or between 0.5 and 2.5 kg water per kg MSW, or between 1.0 and 3.0 kg water per kg MSW. As a result, the actual non-water content of the MSW during processing may vary within the appropriate range.

A variety of different microbial fermentation reactors may be used. In some embodiments, a reactor similar to that described in WO2011/032557 can be used featuring a chamber that rotates on a substantially horizontal axis, equipped with attachments on its inner surface that form a spiral array, which moves MSW continuously from the input to the output end. Depending on the degree to which the reactor is filled, and depending on the size of the reactor, the average "residence time" of MSW within the reactor can be controlled. The reactor can be equipped with heating elements such that an appropriate temperature could be maintained. While continuously introducing MSW into the reactor and continuously removing partially degraded MSW from the reactor, a certain average residence time is obtained. In other embodiments, large vessels, possibly built of concrete or other simple building materials, can be used that are equipped with means for agitation, such as a horizontally mounted shaft having paddles that lift and blend incoming MSW. The reactor may be equipped with means for passive aeration, whereby air exposure is provided and agitation facilitates air exposure. Alternatively the reactor may be configured so as to maintain effectively anaerobic conditions by limiting air exposure.

Agitation may be achieved by a variety of different means. Agitation is advantageous because it promotes not only microbial fermentation per se but also hydrolysis catalysed by enzymes secreted by or otherwise provided by the living microorganisms. Indeed, in this context microbial fermentation is effectively hydrolysis and fermentation. In some embodiments agitation is provided by a kind of free-fall mixing, such as a rotating vessel, or a horizontally mounted shaft providing lifting and blending of MSW in the microbial fermentation milieu. In other embodiments, agitation may be provided by simpler means, such as augers.

A variety of different means may be used to achieve and maintain a lactic acid bacteria concentration of at least $1.0 \times 10^{10}$ CFU (colony forming unit)/L during the course of fermentation. As used herein the lactic acid bacteria concentration is maintained at a concentration during the fermentation step prior to separation of non-degradable solids, to the extent that the concentration of live bacterial cells in the fermentation is on average at least $1.0 \times 10^{10}$ CFU/L over the course of the fermentation. An average of at least $1.0 \times 10^{10}$ CFU/L during the fermentation is typically demonstrated by a series of measurements on samples taken before and after or during the fermentation. The measurement of CFU/L is determined by a measurement expressed as CFU per g total solids present in a representative sample of the mixture, and then expressed as a measurement per L by a measurement of weight percentage total solids content of the mixture. Total solids percentage of a 5 ml representative sample is determined by drying at room temperature in order to provide a basis for calculations. CFU is determined using quantitative PCR (qPCR). 5 ml aliquots of sampled material suspended in 50% by weight glycerol are suspended in 5 ml of sterile-filtered H2O. An aliquot is filtered onto a filter and DNA is extracted from the filtered cell mass. The number of the 16S rRNA gene copy numbers in the extracted DNA are quantified by qPCR analysis with universal 16S rRNA gene primers. Bacterial cell number are calculated based on these data assuming an average of 3.0 copy numbers of the 16s rRNA gene per live cell and expressed in terms of total solids content of the sample analysed. Archaea counts are not included in the count of CFU/L. The percentage of the measured live cell counts that corresponds to lactic acid bacteria is determined based on an estimate provided by 16S rDNA analysis, as well known in the art. A liquid sample of fermentation mixture is frozen in 20% by weight glycerol and stored at −20° C. for the purpose of performing 16S rDNA analysis to identify the microorganisms. This analysis is well known in the art and is widely used for identification and phylogenic analysis of prokaryotes based on the 16S component of the small ribosomal subunit. The analysis comprises extraction of genomic DNA, amplicon library preparation using the universal primers primer pair spanning the hypervariable regions V1 to V3 27F: AGAGTTTGATCCTGGCTCAG/ 534R: ATTACCGCGGCTGCTGG; 507 bp length), PCR tagging with GS FLX adaptors, and sequencing to obtain 104.000-160.000 number of reads per tested sample. The resulting sequences can be queried in a BlastN against the rDNA database from Ribosomal Database Project (Cole et al., 2009). The database contains good quality sequences with at least 1200 bp in length and a NCBI taxonomic association. The current release (RDP Release 10, Updated on Sep. 19, 2012) contains 9,162 bacteria and 375 archaeal sequences The BLAST results can be filtered to remove short and low quality hits (sequence identity ≥90%, alignment coverage ≥90%). The numerical percentage of bacteria detected by this analysis which are lactic acid bacteria, including but not limited to *Lactobacillus* species, is then applied to the total measured CFU/L as a fractional measure of LAB CFU/L. For example, where $2.0\times10^{12}$ CFU/L total live bacterial counts are determined in representative samples of a fermentation mixture, and where 16s RNA analysis of representatives samples of the fermentation mixture indicate that 50% of the detected microorganisms are *Lactobacillus* species, the concentration of lactic acid bacteria is established at the time of the measurement to be at least $1.0\times10^{12}$ CFU/L.

It is generally quite simple to achieve concentrations of lactic acid bacteria of at least $1.0\times10^{10}$ CFU/L. Whether aeration conditions are aerobic or anaerobic, LAB will generally comprise a major proportion of the microbial population that evolves where MSW is simply incubated at temperatures between 37 and 50 degrees C. See e.g Akao et al. 2007a; Akao et al. 2007b; Sakai et al. 2000; Sakai et al. 2004. Accordingly, microbial fermentation conditions can be either aerobic or anaerobic. Live LAB bacteria counts on the order of $1.0\times10^{10}$ CFU/L can be routinely obtained within about 12 hours in lactic acid fermentation of model kitchen waste, without added enzyme activity. See Sakai et al. 2000 and Sakai et al. 2004. Generation doubling times of lactic acid bacteria identified in examples presented subsequently are reportedly on the order of 4 to 5 hours. See Liong and Shaw 2005.

In some embodiments, the incoming MSW stream is simply inoculated with an inoculum of microorganisms naturally occurring in the waste, and optionally "raised" on local waste or components of local waste as a food source in fermentation conditions of temperature within the range 37 to 55 degrees C., or 40 to 55 degrees C., or 45 to 50 degrees C., and at a pH within the range 4.2 and 6.0.

Because LAB generate acidic metabolites, their continuing growth typically involves a requirement for pH adjustment to maintain appropriate growing conditions. Typically LAB prefer pH conditions within the range 4.2 to 6.0. In some embodiments, pH adjustment during microbial fermentation may be provided by microbial means, for example, by including in the microbial fermentation mixture yeast or bacteria or other microorganisms that convert acidic products to non-acidic one, such as the methods described by Nakaski et al. 1996 and Nakasaki et al. 2013.

It is generally advantageous to achieve biological sorting in the shortest practicable time frame, that is, to keep the duration of the microbial fermentation prior to separation of non-degradable solids as short as practicable. This can be achieved with particular speed by providing an initial inoculation of the incoming stream of unsorted MSW. In some embodiments, the inoculum may simply be re-circulated process waters, which can be advantageously heated to temperatures of between 37 and 55 degrees C. In some embodiments the inoculum itself imparts concentrations of live LAB of at least $1.0\times10^{10}$ CFU/L to the incoming MSW stream. In some embodiments freeze-dried cells may be directly added as inoculum. In some embodiments, biodegradable components of MSW from a given location can be used as substrate upon which a lactic acid bacterial inoculum is raised in a fermenter and introduced to the incoming stream of unsorted MSW. In some embodiments, the incoming MSW stream may be subject to heat-sterilization in order that a specific strain of lactic acid bacteria may be inoculated that has specialized advantageous properties.

In some embodiments, a concentration of live LAB is maintained at levels at least $1.0\times10^{10}$ CFU/L or of at least $2.0\times10^{10}$ CFU/L or of at least $3.0\times10^{10}$ CFU/L in the microbial fermentation reactor during continuous operation, with a stream of incoming MSW being continuously introduced, and a stream of fermented MSW being continuously removed prior to separation of non-degradable solids, for a period of at least 20 hours, or at least 50 hours, or at least 70 hours. In some embodiments, microbial fermentation may be conducted concurrently with enzymatic hydrolysis using isolated enzyme preparations. In these embodiments, levels of live LAB during the microbial fermentation prior to separation of non-degradable solids may be much lower, on the order of $5.0\times10^{7}$ CFU/L, or between $5.0$ c $10^{7}$ CFU/L and $1.0\times10^{10}$ CFU/L.

In some embodiments, a microbially-derived cellulase activity of at least 30 FPU/L is provided by the microbial consortium providing microbial fermentation. As used herein the term microbially-derived cellulase activity refers to an activity that is not directly provided by an isolated enzyme preparation that has been added to a fermentation mixture, but rather to an activity provided by living organisms. In some cases, living organisms can provide cellulase activity by bulk secretion of cellulytic enzymes. In other cases, living organisms can provide cellulase activity in comparatively local contact with cellulosic substrates. Microbially-derived cellulase activity is determined as follows: A sample containing living microbes is incubated with addition of a clean, pure cellulose substrate, either tissue paper or filter paper, for a period of 24 hours under conditions of temperature, pH and aeration for which the activity measurement is desired. The solid mass transferred from the added cellulosic substrate to the liquid phase, corrected for "background" transfer of solid mass to the liquid phase by the microbe-containing sample itself, and corrected for "background" transfer of solid mass from the added cellulosic substrate to the liquid phase by water alone under the tested reaction conditions provides a measure of microbially-derived cellulase activity. This measure is then compared with the activity achieved under equivalent conditions by an isolated cellulase enzyme preparation having known cellulase activity in Filter Paper Units (FPU), as determined by the method of Ghose, T. K. (1987), *Measurement of cellulase activities*. Pure & Appl. Chem., 59(2): p. 257-268. The [(sample-background and water-background percentage transfer of solid mass from cellulosic substrate to the liquid phase achieved by the microbe-containing sample) divided by the (water-background percentage transfer of solid mass from cellulosic substrate to the liquid phase achieved by the isolated enzyme preparation)] times the known FPU activity of the isolated enzyme preparation provides a measure of microbially-derived cellulase activity. This activity measurement is then divided by the reaction volume in which the measurement is made to provide a measurement expressed as FPU/L. It will be readily understood by one skilled in the art that the microbe-containing sample may have been diluted prior to measurement, and that a final estimate of FPU/L in the source of the sample may involve a correction for dilution. In cases where some component of FPU activity provided by an isolated enzyme preparation is combined with microbially-derived cellulase activity, the measured microbially-derived cellulase activity is simply corrected by a linear subtraction of the activity provided by isolated enzymes in isolation from the microbial context. An example calculation is given as follows: A 20 ml microbial inoculum sample is incubated for 24 hours in the presence of 1 g added cellulosic substrate. After correcting for background solids release by the inoculum sample itself, a net total of 12% of cellulosic mass is observed to transfer from the cellulosic substrate to the liquid phase. A 20 ml buffer sample to which is added 1 g added cellulosic substrate and an isolated cellulase preparation previously measured to have known FPU activity in an amount corresponding to 5.7 FPU/g cellulose is incubated for 24 hours under equivalent conditions. A net total of 62% of cellulosic mass is observed to transfer from the cellulosic substrate to the liquid phase. A 20 ml water sample to which is added 1 g added cellulosic substrate is incubated for 24 hours under equivalent conditions. A net total of 3% of cellulosic mass is observed to transfer from the cellulosic substrate to the liquid phase. Some small quantity of isolated enzyme preparation having known FPU activity is added to the fermenter from which the microbial inoculum was withdrawn in an amount that, expressed in terms of total volume of the fermenter contents, can be expressed as 8 FPU/L. The measured microbially-derived cellulase activity is given by: [(12% self-background corrected transfer−3% water background transfer)/(62% transfer−3% water transfer)]*(5.7 FPU/0.020 L)=43.5 FPU/L initial microbial−8 FPU/L isolated enzyme contribution=35.47 FPU/L microbially-derived cellulase activity.

In some embodiments, microbially-derived cellulase activity may be provided by specialized cellulase-secreting organisms, which have been included in an inoculum applied to the incoming MSW stream. In some embodiments, microbially-derived cellulase activity may reach levels of at last 50 FPU/L or at least 75 FPU/L or at least 100 FPU/L or at least 300 FPU/L or at least 500 FPU/L or at least 700 FPU/L, or at least 1000 FPU/L. In some embodiments, it can be advantageous to add isolated enzyme preparations to the microbial fermentation mixture, including amylase preparations, or other enzyme preparations.

The duration of microbial fermentation prior to separation of non-degradable solids is determined by the average residence time within the microbial fermentation reactor. In some embodiments, average residence time of the MSW stream in microbial fermentation prior to separation of degradable materials is 18 hours or less, or 24 hours or less, or 36 hours or less, or between 36 hours and 48 hours, or between 48 hours and 60 hours, or between 60 hours and 72 hours, or 72 hours or less. In some embodiments the invention provides a bio-degradable slurry obtained by the method of processing MSW.

A steam of fermented MSW is removed from the microbial fermentation reactor, typically in a continuous manner. That is a stream of unsorted MSW is continuously introduced to the reactor and a stream of partially hydrolysed, fermented MSW is continuously removed from the reactor. In some embodiments, however, the stream of MSW may be introduced in a pulsatile manner, with one injection of MSW, followed by a pause, followed by a subsequent injection of MSW. Similarly in some embodiments the stream of partially hydrolysed, fermented MSW may be removed from the reactor in a pulsatile manner, with one ejection of MSW, followed by a pause, followed by a subsequent ejection of MSW and so on.

After removal from the microbial fermentation reactor, the partially hydrolysed, fermented MSW is subject to a separation step whereby non-degradable solids are removed to provide a slurry of biodegradable components. This separation step, and subsequent processing, can be achieved in a variety of different ways.

In some embodiments, the separation step is achieved in two steps. First, a ballistic separator removes two streams of non-degradable materials, producing a "two dimensional" (2D) fraction comprising plastic bags and other generally formless material, a "three dimensional" (3D) fraction comprising bottles and containers having a definite shape, and a volume of a biogenic liquid slurry of bio-degradable components. In a second step, the 2D fraction is further subject to pressing with a screw press or similar device to further increase the yield of the biogenic slurry.

In some embodiments, the 2D fraction is further subject to washing, in order to further recover bio-degradable material. The wash waters obtained in this step can then be maintained at the fermentation temperature and used to wet and also inoculate incoming unsorted MSW.

In some embodiments the processing scheme described in FIG. 1 can be used. FIG. 1 shows a schematic illustration of principle features of the REnescience Version 1 demonstration plant. Unsorted MSW is subject to a biological sorting process that produces four products—a biogenic slurry suitable for biomethane production or other processes, inerts (glass and sand) for recycling, and both a "two dimensional" (2D) and a "three dimensional" (3D) fraction of inorganic materials suitable for RDF production as well as for recycling of metals, plastic and wood. MSW from urban areas is collected as-is in plastic bags. The MSW is transported to the REnescience Waste Refinery where it is stored in a silo until processing. Depending on the character of the MSW a sorting step can be installed in front of the REnescience system to take out oversize particles (above 500 mm). A stream of unsorted MSW is heated and its non-water content adjusted by addition of heated aqueous solution. In some embodiments, cellulase activity provided by isolated enzyme preparations may be added to facilitate rapid degradation of the biodegradable component of the MSW. In some embodiments isolated enzyme preparations are added to the heated MSW at an appropriate non-water content. In some embodiments, no isolated enzyme preparations are added and microbial hydrolysis and fermentation is provided by maintain lactic acid bacteria during the course of fermentation at levels of live bacterial cells at least $1.0 \times 10^{\wedge} 10$ CFU/L. The MSW, with or without added enzymes, can be incubated in a microbial fermentation reactor similar to that described in WO2011/032557. While continuously introducing MSW into the reactor and continuously removing partially degraded MSW from the reactor, a certain average residence time is obtained. Partially degraded MSW removed from the reactor can then be subject to two distinct separation steps. First, a ballistic separator, often used in sorting, can be used, for example having sieves between 20-50 mm to produce a biogenic slurry stream, as well as a 3D non-degradable fraction and a 2D non-degradable fraction.

In some embodiments, as shown in FIG. 1, the 2D non-degradable fraction can be further subject to de-watering using a screw press, with recovery of additional biogenic slurry that is, in turn, blended with the slurry obtained from the ballistic separator step.

In some embodiments, as shown in FIG. 1, the obtained biogenic slurry can be subject to further "fine" separation using a series of vibrating sieves, for example a course sieve of 6-10 mm, for example 8 mm, followed by one or more finer sieves of 2-6 mm, for example, 3 mm. These coarser sieves typically separate out primarily non-degradable contaminants. The finer sieves, for example 3 mm sieves, typically separate out larger fibers, which comprise a considerable amount of bio-degradable material. After passing through the finer sieves, in some embodiments the obtained biogenic slurry, which is typically pumpable (i.e., liquid) can be stored in a large tank.

In some embodiments, bio-degradable materials retained by one or more sieve systems may be re-introduced to the stored biogenic slurry and subject to post-fermentation, so as to achieve more complete degradation of the material, at a temperature between 35 and 75 degrees for a period of between 1 and 72 hours.

In some embodiments, as shown in FIG. 1, the de-watered solid non-degradable 2D fraction can be subject to a counter-current washing train to both clean the 2D fraction and also to recover additional bio-degradable material that would otherwise be lost. For example the water flows in some embodiments may be as shown in FIG. 1. Fresh water can be applied to washing 3D non-degradable material recovered from the ballistic separator in a simple drum. This wash water can then be used as "clean" water which is fed into the second of two identical washing units so as to provide counter-current washing—the "clean" new water encounters the "cleanest" trash while consecutively more dirty water is applied to incoming "dirtier" trash. In some embodiments, the washing train works as follows: the dirty 2D fraction enters a drum in the first washing unit, where the waste is mixed with the counter-current washing water and mechanically mixed.

Additionally the dirty wash water can be subjected to sieve filtration having 0.04 to 0.08 mm sieves, to remove fibres, which typically comprise primarily bio-degradable material. Sand and heavy material can also be removed by sedimentation and by a screw conveyer in the bottom of each washing unit. The fraction removed is typically mostly sand/glass/heavy plastic/and other inorganics. After the first wash, the waste can be moved by screw auger or other means into a second washing unit, which can be identical to the first. The wash water from the first wash unit in such embodiments typically has between 1-4% by weight TS (total solids) whereas the wash water from the second wash unit typically has 0.5-3.0% by weight.

The wash waters, comprising some bio-degradable material recovered from the MSW as well as associated microorganisms, in some embodiments can be stored in a "buffer" tank. Aqueous solution from this "buffer" tank can then be used to adjust the non-water content of incoming MSW. In some embodiments the solution from the "buffer" tank can be heated by applying steam, then mixing the heated solution with incoming MSW so as to simultaneously heat it to an appropriate temperature and also adjust the non-water content. In some embodiments, the solution from the "buffer" tank is itself heated in the buffer tank to a temperature within the range of 35 to 55 degrees C. The mere act of heating the buffer tank storing wash waters is sufficient to induce fermentation and promote bacterial growth, enriching the capacity of the solution to serve as an "inoculum" to incoming MSW, to facilitate microbial fermentation. In some embodiments, the heated "buffer" tank storing wash waters can be agitated, pH adjusted, and "fed" with biodegradable material retained by one or more sieve system or by obtained biogenic slurry or both, so as to further promote bacterial fermentation and so as to further enhance the "potency" of the solution as an inoculum for incoming MSW.

The separation of non-degradable solids and the scheme for promoting microbial fermentation can be achieved by a variety of means. In some embodiments, the incoming MSW stream can be fed into the microbial fermentation reactor, then after a period of microbial fermentation, directly subject to pressing with a screw press, with separation of biogenic slurry, followed by addition of fresh water, followed by a second screw press treatment, producing a dilute biogenic slurry recovered from the second screw press treatment which can be used to adjust non-water content and provide inoculation of the incoming MSW stream. Or in some embodiments a similar scheme is applied, directly, and some or all of the biogenic slurry is used to adjust non-water content of the incoming MSW stream.

In some embodiments, the incoming MSW stream can be fed into the microbial fermentation reactor, then after a period of microbial fermentation subject to a separation step such as ballistic separator or drum separator or vibrating sieve, with some recovery of biogenic slurry, followed by pressing with a screw press to recover additional biogenic slurry, some of which slurry can be used directly to adjust non-water content of the incoming MSW stream.

In some embodiments, microbial fermentation is accomplished concurrently with enzymatic hydrolysis. Enzymatic hydrolysis can be achieved using a variety of different means. In some embodiments, enzymatic hydrolysis can be achieved using isolated enzyme preparations. As used herein, the term "isolated enzyme preparation" refers to a preparation comprising enzyme activities that have been extracted, secreted or otherwise obtained from a biological source and optionally partially or extensively purified.

A variety of different enzyme activities may be advantageously used to practice methods of the invention. Considering, for example, the composition of MSW shown in Table 1, it will be readily apparent that, at least in Denmark, paper-containing wastes comprise the greatest single component, by dry weight, of the biogenic material. Accordingly, as will be readily apparent to one skilled in the art, for typical household waste, cellulose-degrading activity will be particularly advantageous. In paper-containing wastes, cellulose has been previously processed and separated from its natural occurrence as a component of lignocellulosic biomass, intermingled with lignin and hemicellulose. Accordingly, paper-containing wastes can be advantageously degraded using a comparatively "simple" cellulase preparation.

"Cellulase activity" refers to enzymatic hydrolysis of 1,4-B-D-glycosidic linkages in cellulose. In isolated cellulase enzyme preparations obtained from bacterial, fungal or other sources, cellulase activity typically comprises a mixture of different enzyme activities, including endoglucanases and exoglucanases (also termed cellobiohydrolases), which respectively catalyse endo- and exo-hydrolysis of 1,4-B-D-glycosidic linkages, along with B-glucosidases, which hydrolyse the oligosaccharide products of exoglucanase hydrolysis to monosaccharides. Complete hydrolysis of insoluble cellulose typically requires a synergistic action between the different activities.

As a practical matter, it can be advantageous in some embodiments to simply use a commercially available isolated cellulase preparation optimized for lignocellulosic biomass conversion, since these are readily available at comparatively low cost. These preparations are certainly suitable for practicing methods of the invention. The term "optimized for lignocellulosic biomass conversion" refers to a product development process in which enzyme mixtures have been selected and modified for the specific purpose of improving hydrolysis yields and/or reducing enzyme consumption in hydrolysis of pretreated lignocellulosic biomass to fermentable sugars.

However, commercial cellulase mixtures optimized for hydrolysis of lignocellulosic biomass typically contain high levels of additional and specialized enzyme activities. For example, we determined the enzyme activities present in commercially available cellulase preparations optimized for lignocellulosic biomass conversion and provided by NOVOZYMES™ under the trademarks CELLIC CTEC2™ and CELLIC CTEC3™ as well as similar preparations provided by GENENCOR™ under the trademark ACCELLERASE 1500™ and found that each of these preparations contained endoxylanase activity over 200 U/g, xylosidase activity at levels over 85 U/g, B-L-arabinofuranosidase activity at levels over 9 U/g, amyloglucosidase activity at levels over 15 U/g, and a-amylase activity at levels over 2 U/g.

Simpler isolated cellulase preparations may also be effectively used to practice methods of the invention. Suitable cellulase preparations may be obtained by methods well known in the art from a variety of microorganisms, including aerobic and anaerobic bacteria, white rot fungi, soft rot fungi and anaerobic fungi. As described in ref. 13, R. Singhania et al., "Advancement and comparative profiles in the production technologies using solid-state and submerged fermentation for microbial cellulases," Enzyme and Microbial Technology (2010) 46:541-549, which is hereby expressly incorporated by reference in entirety, organisms that produce cellulases typically produce a mixture of different enzymes in appropriate proportions so as to be suitable for hydrolysis of lignocellulosic substrates. Preferred sources of cellulase preparations useful for conversion of lignocellulosic biomass include fungi such as species of *Trichoderma, Penicillium, Fusarium, Humicola, Aspergillus* and *Phanerochaete*.

In addition to cellulase activity, some additional enzyme activities which can prove advantageous in practicing methods of the invention include enzymes which act upon food wastes, such as proteases, glucoamylases, endoamylases, proteases, pectin esterases, pectin lyases, and lipases, and enzymes which act upon garden wastes, such as xylanases, and xylosidases. In some embodiments it can be advantageous to include other enzyme activities such as laminarases, ketatinases or laccases.

In some embodiments, a selected microorganism that exhibits extra-cellular cellulase activity may be directly inoculated in performing concurrent enzymatic hydrolysis and microbial fermentation, including but not limited to any one or more of the following thermophilic, cellulytic organisms can be inoculated, alone or in combination with other organisms *Paenibacillus barcinonensis*, see Asha et al 2012, *Clostridium thermocellum*, see Blume et al 2013 and Lv and Yu 2013, selected species of *Streptomyces, Microbispora*, and *Paenibacillus*, see Eida et al 2012, *Clostridium straminisolvens*, see Kato et al 2004, species of *Firmicutes, Actinobacteria, Proteobacteria* and *Bacteroidetes*, see Maki et al 2012, *Clostridium clariflavum*, see Sasaki et al 2012, new species of *Clostridiales* phylogenetically and physiologically related to *Clostridium thermocellum* and *Clostridium straminisolvens*, see Shiratori et al 2006, *Clostridium clariflavum* sp. nov. and *Clostridium Caenicola*, see Shiratori et al 2009, *Geobacillus Thermoleovorans*, see Tai et al 2004, *Clostridium stercorarium*, see Zverlov et al 2010, or any one or more of the thermophilic fungi *Sporotrichum thermophile, Scytalidium thermophillum, Clostridium straminisolvens* and *Thermonospora curvata*, Kumar et al. 2008 for review. In some embodiments, organisms exhibiting other useful extra cellular enzymatic activities may be inoculated to contribute to concurrent enzymatic hydrolysis and microbial fermentation, for example, proteolytic and keratinolytic fungi, see Kowalska et al. 2010, or lactic acid bacteria exhibiting extra-cellular lipase activity, see Meyers et al. 1996.

Enzymatic hydrolysis can be conducted by methods well known in the art, using one or more isolated enzyme preparations comprising any one or more of a variety of enzyme preparations including any of those mentioned previously or, alternatively, by inoculating the process MSW with one or more selected organisms capable of affecting the desired enzymatic hydrolysis. In some embodiments, enzymatic hydrolysis can be conducted using an effective amount of one or more isolated enzyme preparations comprising cellulase, B-glucosidase, amylase, and xylanase activities. An amount is an "effective amount" where collectively the enzyme preparation used achieves solubilisation of at least 40% of the dry weight of degradable biogenic material present in MSW within a hydrolysis reaction time of 18 hours under the conditions used. In some embodiments, one or more isolated enzyme preparations is used in which collectively the relative proportions of the various enzyme activities is as follows: A mixture of enzyme activities is used such that 1 FPU cellulase activity is associated with at least 31 CMC U endoglucanase activity and such that 1 FPU cellulase activity is associated with at least at least 7 pNPG U beta glucosidase activity. It will be readily understood by one skilled in the art that CMC U refers to carboxymethylcellulose units. One CMC U of activity liberates 1 umol of reducing sugars (expressed as glucose equivalents) in one minute under specific assay conditions of 50° C. and pH 4.8. It will be readily understood by one skilled in the art that pNPG U refers to pNPG units. One pNPG U of activity liberates 1 umol of nitrophenol per minute from para-nitrophenyl-B-D-glucopyranoside at 50° C. and pH 4.8. It will be further readily understood by one skilled in the art that FPU of "filter paper units" provides a measure of cellulase activity. As used herein, FPU refers to filter paper units as determined by the method of Adney, B. and Baker, J., Laboratory Analytical Procedure #006, "Measurement of cellulase activity", Aug. 12, 1996, the USA National Renewable Energy Laboratory (NREL), which is expressly incorporated by reference herein in entirety.

In practicing embodiments of the invention, it can be advantageous to adjust the temperature of the MSW prior to initiation of enzymatic hydrolysis. As is well known in the art, cellulases and other enzymes typically exhibit an optimal temperature range. While examples of enzymes isolated from extreme thermophilic organisms are certainly known, having optimal temperatures on the order of 60 or even 70 degrees C., enzyme optimal temperature ranges typically fall within the range 35 to 55 degrees. In some embodiments, enzymatic hydrolysis are conducted within the temperature range 30 to 35 degrees C., or 35 to 40 degrees C., or 40 to 45 degrees C., or 45 to 50 degrees C., or 50 to 55 degrees C., or 55 to 60 degrees C., or 60 to 65 degrees C., or 65 to 70 degrees C., or 70 to 75 degrees C. In some embodiments it is advantageous to conduct enzymatic hydrolysis and concurrent microbial fermentation at a temperature of at least 45 degrees C., because this is advantageous in discouraging growth of MSW-bourne pathogens. See e.g. Hartmann and Ahring 2006; Deportes et al. 1998; Carrington et al. 1998; Bendixen et al. 1994; Kubler et al. 1994; Six and De Baerre et al. 1992.

Enzymatic hydrolysis using cellulase activity will typically sacchartify cellulosic material. Accordingly, during enzymatic hydrolysis, solid wastes are both saccharified and liquefied, that is, converted from a solid form into a liquid slurry.

Previously, methods of processing MSW using enzymatic hydrolysis to achieve liquefaction of biogenic components have envisioned a need for heating MSW to a temperature considerably higher than that required for enzymatic hydrolysis, specifically to achieve "sterilization" of the waste, followed by a necessary cooling step, to bring the heated waste back down to a temperature appropriate for enzymatic hydrolysis. In practicing methods of the invention, it is sufficient that MSW be simply brought to a temperature appropriate for enzymatic hydrolysis. In some embodiments it can be advantageous to simply adjust MSW to an appropriate non-water content using heated water, administered in such manner so as to bring the MSW to a temperature appropriate for enzymatic hydrolysis. In some embodiments, MSW is heated, either by adding heated water content, or steam, or by other means of heating, within a reactor vessel. In some embodiments, MSW is heated within a reactor vessel to a temperature greater than 30° C. but less than 85° C., or to a temperature of 84° C. or less, or to a temperature of 80° C. or less, or to a temperature of 75° C. or less, or to a temperature of 70° C. or less, or to a temperature of 65° C. or less, or to a temperature of 60° C. or less, or to a temperature of 59° C. or less, or to a temperature of 58° C. or less, or to a temperature of 57° C. or less, or to a temperature of 56° C. or less, or to a temperature of 55° C. or less, or to a temperature of 54° C. or less, or to a temperature of 53° C. or less, or to a temperature of 52° C. or less, or to a temperature of 51° C. or less, or to a temperature of 50° C. or less, or to a temperature of 49° C. or less, or to a temperature of 48° C. or less, or to a temperature of 47° C. or less, or to a temperature of 46° C. or less, or to a temperature of 45° C. or less. In some embodiments, MSW is heated to a temperature not more than 10° C. above the highest temperature at which enzymatic hydrolysis is conducted.

As used herein MSW is "heated to a temperature" where the average temperature of MSW is increased within a reactor to the temperature. As used herein, the temperature to which MSW is heated is the highest average temperature of MSW achieved within the reactor. In some embodiments, the highest average temperature may not be maintained for the entire period. In some embodiments, the heating reactor may comprise different zones such that heating occurs in stages at different temperatures. In some embodiments, heating may be achieved using the same reactor in which enzymatic hydrolysis is conducted. The object of heating is simply to render the majority of cellulosic wastes and a substantial fraction of the plant wastes in a condition optimal for enzymatic hydrolysis. To be in a condition optimal for enzymatic hydrolysis, wastes should ideally have a temperature and water content appropriate for the enzyme activities used for enzymatic hydrolysis.

In some embodiments, it can be advantageous to agitate during heating so as to achieve evenly heated waste. In some embodiments, agitation can comprise free-fall mixing, such as mixing in a reactor having a chamber that rotates along a substantially horizontal axis or in a mixer having a rotary axis lifting the MSW or in a mixer having horizontal shafts or paddles lifting the MSW. In some embodiments, agitation can comprise shaking, stirring or conveyance through a transport screw conveyor. In some embodiments, agitation continues after MSW has been heated to the desired temperature. In some embodiments, agitation is conducted for between 1 and 5 minutes, or between 5 and 10 minutes, or between 10 and 15 minutes, or between 15 and 20 minutes, or between 20 and 25 minutes, or between 25 and 30 minutes, or between 30 and 35 minutes, or between 35 and 40 minutes, or between 40 and 45 minutes, or between 45 and 50 minutes, or between 50 and 55 minutes, or between 55 and 60 minutes, or between 60 and 120 minutes.

Enzymatic hydrolysis is initiated at that point at which isolated enzyme preparations are added. Alternatively, in the event that isolated enzyme preparations are not added, but instead microorganisms that exhibit desired extracellular enzyme activities are used, enzymatic hydrolysis is initiated at that point which the desired microorganism is added.

In practicing some embodiments, enzymatic hydrolysis is conducted concurrently with microbial fermentation. Concurrent microbial fermentation can be achieved using a variety of different methods. In some embodiments, microorganisms naturally present in the MSW are simply allowed to thrive in the reaction conditions, where the processed MSW has not previously been heated to a temperature that is sufficient to effect a "sterilization." Typically, microorganisms present in MSW will include organisms that are adapted to the local environment. The general beneficial effect of concurrent microbial fermentation is comparatively robust, meaning that a very wide variety of different organisms can, individually or collectively, contribute to organic capture through enzymatic hydrolysis of MSW. Without wishing to be bound by theory, we consider that co-fermenting microbes individually have some direct effect on degradation of food wastes that are not necessarily hydrolysed by cellulase enzymes. At the same time, carbohydrate monomers and oligomers released by cellulase hydrolysis, in particular, are readily consumed by virtually any microbial species. This gives a beneficial synergy with cellulase enzymes, possibly through release of product inhibition of the enzyme activities, and also possibly for other reasons that are not immediately apparent. The end products of microbial metabolism in any case are typically appropriate for biomethane substrates. The enrichment of enzymatically hydrolysed MSW in microbial metabolites is, thus, already, in and of itself, an improvement in quality of the resulting biomethane substrate. Lactic acid bacteria in particular are ubiquitous in nature and lactic acid production is typically observed where MSW is enzymatically hydrolysed at non-water content between 10 and 45% within the temperature range 45-50%. At higher temperatures, possibly other species of naturally occurring microorganisms may predominate and other microbial metabolites than lactic acid may become more prevalent.

In some embodiments, microbial fermentation can be accomplished by a direct inoculation using one or more microbial species. It will be readily understood by one skilled in the art that one or more bacterial species used for inoculation so as to provide simultaneous enzymatic hydrolysis and fermentation of MSW can be advantageously selected where the bacterial species is able to thrive at a temperature at or near the optimum for the enzymatic activities used.

Inoculation of the hydrolysis mixture so as to induce microbial fermentation can be accomplished by a variety of different means.

In some embodiments, it can be advantageous to inoculate the MSW either before, after or concurrently with the addition of enzymatic activities or with the addition of microorganisms that exhibit extra-cellular cellulase activity. In some embodiments, it can be advantageous to inoculate using one or more species of LAB including but not limited to any one or more of the following, or genetically modified variants thereof: *Lactobacillus plantarum, Streptococcus lactis, Lactobacillus casei, Lactobacillus lactis, Lactobacillus curvatus, Lactobacillus sake, Lactobacillus helveticus, Lactobacillus jugurti, Lactobacillus fermentum, Lactobacillus camis, Lactobacillus piscicola, Lactobacillus coryniformis, Lactobacillus rhamnosus, Lactobacillus maltaromicus, Lactobacillus pseudo plantarum, Lactobacillus agilis, Lactobacillus bavaricus, Lactobacillus alimentarius, Lactobacillus uamanashiensis, Lactobacillus amylophilus, Lactobacillus farciminis, Lactobacillus sharpeae, Lactobacillus divergens, Lactobacillus alactosus, Lactobacillus paracasei, Lactobacillus homohiochii, Lactobacillus sanfrancisco, Lactobacillus fructivorans, Lactobacillus brevis, Lactobacillus ponti, Lactobacillus reuteri, Lactobacillus buchneri, Lactobacillus viridescens, Lactobacillus confusus, Lactobacillus minor, Lactobacillus kandleri, Lactobacillus halotolerans, Lactobacillus hilgardi, Lactobacillus kefir, Lactobacillus collinoides, Lactobacillus vaccinostericus, Lactobacillus delbrueckii, Lactobacillus bulgaricus, Lactobacillus leichmanni, Lactobacillus acidophilus, Lactobacillus salivarius, Lactobacillus salicinus, Lactobacillus gasseri, Lactobacillus suebicus, actobacillus oris, Lactobacillus brevis, Lactobacillus vaginalis, Lactobacillus pentosus, Lactobacillus panis, Lactobacillus amylolyticus, Lactobacillus similis, Lactobacillus parabuchneri, Lactobacillus pontis, Lactobacillus paraplantarum, Lactobacillus mucosae, Lactobacillus amylovorus, Lactobacillus sobrius, Lactobacillus frumenti, Lactobacillus pentosus, Lactococcus cremoris, Lactococcus dextranicum, Lactococcus garvieae, Lactococcus hordniae, Lactococcus raffinolactis, Streptococcus diacetylactis, Leuconostoc mesenteroides, Leuconostoc dextranicum, Leuconostoc cremoris, Leuconostoc oenos, Leuconostoc paramesenteroides, Leuconostoc pseudoesenteroides, Leuconostoc citreum, Leuconostoc gelidum, Leuconostoc carnosum, Pediococcus damnosus, Pediococcus acidilactici, Pediococcus cervisiae, Pediococcus parvulus, Pediococcus halophilus, Pediococcus pentosaceus, Pediococcus intermedius, Bifidobacterium longum, Streptococcus thermophilus, Oenococcus oeni, Bifidobacterium breve*, and *Propionibacterium freudenreichii*, or with some subsequently discovered species of LAB or with other species from the genera *Enterococcus, Lactobacillus, Lactococcus, Leuconostoc, Pediococcus*, or *Carnobacterium* that exhibit useful capacity for metabolic processes that produce lactic acid.

It will be readily understood by one skilled in the art that a bacterial preparation used for inoculation may comprise a community of different organisms. In some embodiments, naturally occurring bacteria which exist in any given geographic region and which are adapted to thrive in MSW from that region, can be used. As is well known in the art, LAB are ubiquitous and will typically comprise a major component of any naturally occurring bacterial community within MSW.

In some embodiments, MSW can be inoculated with naturally occurring bacteria, by continued recycling of wash waters or process solutions used to recover residual organic material from non-degradable solids. As the wash waters or process solutions are recycled, they gradually acquire higher microbe levels. In some embodiments, microbial fermentation has a pH lowering effect, especially where metabolites comprise short chain carboxylic acids/fatty acids such as formate, acetate, butyrate, proprionate, or lactate. Accordingly in some embodiments it can be advantageous to monitor and adjust pH of the concurrent enzymatic hydrolysis and microbial fermentation mixture. Where wash waters or process solutions are used to increase water content of incoming MSW prior to enzymatic hydrolysis, inoculation is advantageously made prior to addition of enzyme activities, either as isolated enzyme preparations or as microorganisms exhibiting extra-cellular cellulase activity. In some embodiments, naturally occurring bacteria adapted to thrive on MSW from a particular region can be cultured on MSW or on liquefied organic component obtained by enzymatic hydrolysis of MSW. In some embodiments, cultured naturally occurring bacteria can then be added as an inoculum, either separately or supplemental to inoculation using recycled wash waters or process solutions. In some embodiments, bacterial preparations can be added before or concurrently with addition of isolated enzyme preparations, or after some initial period of pre-hydrolysis.

In some embodiments, specific strains can be cultured for inoculation, including strains that have been specially modified or "trained" to thrive under enzymatic hydrolysis reaction conditions and/or to emphasize or de-emphasize particular metabolic processes. In some embodiments, it can be advantageous to inoculate MSW using bacterial strains which have been identified as capable of surviving on phthalates as sole carbon source. Such strains include but are not limited to any one or more of the following, or genetically modified variants thereof: *Chryseomicrobium intechense* MW10T, *Lysinibacillus fusiformis* NBRC 157175, *Tropicibacter phthalicus*, *Gordonia* JDC-2, *Arthobacter* JDC-32, *Bacillus subtilis* 3C3, *Comamonas testosteronii*, *Comamonas* sp E6, *Delftia tsuruhatensis*, *Rhodoccoccus jostii*, *Burkholderia cepacia*, *Mycobacterium vanbaalenii*, *Arthobacter keyseri*, *Bacillus* sb 007, *Arthobacter* sp. PNPX-4-2, *Gordonia namibiensis*, *Rhodococcus phenolicus*, *Pseudomonas* sp. PGB2, *Pseudomonas* sp. Q3, *Pseudomonas* sp. 1131, *Pseudomonas* sp. CAT1-8, *Pseudomonas* sp. *Nitroreducens*, *Arthobacter* sp AD38, *Gordonia* sp CNJ863, *Gordonia rubripertinctus*, *Arthobacter oxydans*, *Acinetobacter genomosp*, and *Acinetobacter calcoaceticus*. See e.g. Fukuhura et al 2012; Iwaki et al. 2012A; Iwaki et al. 2012B; Latorre et al. 2012; Liang et al. 2010; Liang et al. 2008; Navacharoen et al. 2011; Park et al. 2009; Wu et al. 2010; Wu et al. 2011. Phthalates, which are used as plasticizers in many commercial poly vinyl chloride preparations, are leachable and, in our experience, are often present in liquefied organic component at levels that are undesirable. In some embodiments, strains can be advantageously used which have been genetically modified by methods well known in the art, so as to emphasize metabolic processes and/or de-emphasize other metabolic processes including but not limited to processes that consume glucose, xylose or arabinose.

In some embodiments, it can be advantageous to inoculate MSW using bacterial strains which have been identified as capable of degrading lignin. Such strains include but are not limited to any one or more of the following, or genetically modified variants thereof: *Comamonas* sp 8-9, *Citrobacter freundii*, *Citrobacter* sp FJ581023, *Pandorea norimbergensis*, *Amycolatopsis* sp ATCC 39116, *Streptomyces viridosporous*, *Rhodococcus jostii*, and *Sphingobium* sp. SYK-6. See e.g. Bandounas et al. 2011; Bugg et al. 2011; Chandra et al. 2011; Chen et al. 2012; Davis et al. 2012. In our experience, MSW typically comprises considerable lignin content, which is typically recovered as undigested residual after AD.

In some embodiments, it can be advantageous to inoculate MSW using an acetate-producing bacterial strain, including but not limited to any one or more of the following, or genetically modified variants thereof: *Acetitomaculum ruminis*, *Anaerostipes caccae*, *Acetoanaerobium noterae*, *Acetobacterium carbinolicum*, *Acetobacterium wieringae*, *Acetobacterium woodii*, *Acetogenium kivui*, *Acidaminococcus fermentans*, *Anaerovibrio lipolytica*, *Bacteroides coprosuis*, *Bacteroides pro pionicifaciens*, *Bacteroides cellulosolvens*, *Bacteroides xylanolyticus*, *Bifidobacterium catenulatum*, *Bifidobacterium bifidum*, *Bifidobacterium adolescentis*, *Bifidobacterium angulatum*, *Bifidobacterium breve*, *Bifidobacterium gallicum*, *Bifidobacterium infantis*, *Bifidobacterium longum*, *Bifidobacterium pseudolongum*, *Butyrivibrio fibrisolvens*, *Clostridium aceticum*, *Clostridium acetobutylicum*, *Clostridium acidurici*, *Clostridium bifermentans*, *Clostridium botulinum*, *Clostridium butyricum*, *Clostridium cellobioparum*, *Clostridium formicaceticum*, *Clostridium histolyticum*, *Clostridium lochheadii*, *Clostridium methylpentosum*, *Clostridium pasteurianum*, *Clostridium perfringens*, *Clostridium propionicum*, *Clostridium putrefaciens*, *Clostridium sporogenes*, *Clostridium tetani*, *Clostridium tetanomorphum*, *Clostridium thermocellum*, *Desulfotomaculum orientis*, *Enterobacter aerogenes*, *Escherichia coli*, *Eubacterium limosum*, *Eubacterium ruminantium*, *Fibrobacter succinogenes*, *Lachnospira multiparus*, *Megasphaera elsdenii*, *Moorella thermoacetica*, *Pelobacter acetylenicus*, *Pelobacter acidigallici*, *Pelobacter massiliensis*, *Prevotella ruminocola*, *Propionibacterium freudenreichii*, *Ruminococcus flavefaciens*, *Ruminobacter amylophilus*, *Ruminococcus albus*, *Ruminococcus bromii*, *Ruminococcus champanellensis*, *Selenomonas ruminantium*, *Sporomusa paucivorans*, *Succinimonas amylolytica*, *Succinivibrio dextrinosolven*, *Syntrophomonas wolfei*, *Syntrophus aciditrophicus*, *Syntrophus gentianae*, *Treponema bryantii* and *Treponema primitia*.

In some embodiments, it can be advantageous to inoculate MSW using a butyrate-producing bacterial strain, including but not limited to any one or more of the following, or genetically modified variants thereof: *Acidaminococcus fermentans*, *Anaerostipes caccae*, *Bifidobacterium adolescentis*, *Butyrivibrio crossotus*, *Butyrivibrio fibrisolvens*, *Butyrivibrio hungatei*, *Clostridium acetobutylicum*, *Clostridium aurantibutyricum*, *Clostridium beijerinckii*, *Clostridium butyricum*, *Clostridium cellobioparum*, *Clostridium difficile*, *Clostridium innocuum*, *Clostridium kluyveri*, *Clostridium pasteurianum*, *Clostridium perfringens*, *Clostridium proteoclasticum*, *Clostridium sporosphaeroides*, *Clostridium syrnbiosum*, *Clostridium tertium*, *Clostridium tyrobutyricum*, *Coprococcus eutactus*, *Coprococcus comes*, *Escherichia coli*, *Eubacterium barkeri*, *Eubacterium biforme*, *Eubacterium cellulosolvens*, *Eubacterium cylindroides*, *Eubacterium dolichum*, *Eubacterium hadrum*, *Eubacterium halii*, *Eubacterium limosum*, *Eubacterium moniliforme*, *Eubacterium oxiororeducens*, *Eubacterium ramulus*, *Eubacterium rectale*, *Eubacterium saburreum*, *Eubacterium tortuosum*, *Eubacterium ventriosum*, *Faecalibacterium prausnitzii*, *Fusobacterium prausnitzii*, *Peptostreptoccoccus vaginalis*, *Peptostreptoccoccus tetradius*, *Pseudobutyrivibrio ruminis*, *Pseudobutyrivibrio xylanivorans*, *Roseburia cecicola*, *Roseburia intestinalis*, *Roseburia hominis* and *Ruminococcus bromii*.

In some embodiments, it can be advantageous to inoculate MSW using a propionate-producing bacterial strain, including but not limited to any one or more of the following, or genetically modified variants thereof: *Anaerovibrio lipolytica*, *Bacteroides coprosuis*, *Bacteroides pro pionicifaciens*, *Bifidobacterium adolescentis*, *Clostridium acetobutylicum*, *Clostridium butyricium*, *Clostridium methylpentosum*, *Clostridium pasteurianum*, *Clostridium perfringens*, *Clostridium propionicum*, *Escherichia coli*, *Fusobacterium nucleatum*, *Megasphaera elsdenii*, *Prevotella ruminocola*, *Propionibacterium freudenreichii*, *Ruminococcus bromii*, *Ruminococcus champanellensis*, *Selenomonas ruminantium* and *Syntrophomonas wolfei*.

In some embodiments, it can be advantageous to inoculate MSW using an ethanol-producing bacterial strain, including but not limited to any one or more of the following, or genetically modified variants thereof: *Acetobacterium carbinolicum*, *Acetobacterium wieringae*, *Acetobacterium woodii*, *Bacteroides cellulosolvens*, *Bacteroides xylanolyticus*, *Clostridium acetobutylicum*, *Clostridium beijerinckii*, *Clostridium butyricium*, *Clostridium cellobioparum*, *Clostridium lochheadii*, *Clostridium pasteurianum*, *Clostridium perfringens*, *Clostridium thermocellum*, *Clostridium thermohydrosulfuricum*, *Clostridium thermosaccharolyticum*, *Enterobacter aerogenes*, *Escherichia coli*, *Klebsiella oxytoca*, *Klebsiella pneumonia*, *Lachnospira multiparus*, *Lactobacillus brevis*, *Leuconostoc mesenteroides*, *Paentacilius macerans*, *Pelobacter acetylenicus*, *Ruminococcus albus*, *Thermoanaerobacter mathranii*, *Treponema bryantii* and *Zymomonas mobilis*.

In some embodiments, a consortium of different microbes, optionally including different species of bacteria and/or fungi, may be used to accomplish concurrent microbial fermentation. In some embodiments, suitable microorganisms may be selected so as to provide a desired metabolic outcome at the intended reaction conditions, and then inoculated at a high dose level so as to outcompete naturally occurring strains. For example, in some embodiments, it can be advantageous to inoculate using a homofermentive lactate producer, since this provides a higher eventual methane potential in a resulting biomethane substrate than can be provided by a heterofermentive lactate producer.

In some embodiments, the invention provides a method of processing municipal solid waste (MSW) comprising the steps of (i). providing MSW at a non-water content of between 5 and 40% and at a temperature of within the range 35 and 75 degrees C., (ii). subjecting the biodegradable parts of the MSW to microbial fermentation and enzymatic hydrolysis at a temperature within the range 35 and 75 degrees C. resulting in partial liquefaction of biodegradable parts of the waste and accumulation of microbial metabolites, followed by (iii). sorting of the liquefied, biodegradable parts of the waste from non-biodegradable solids to produce a biodegradable slurry characterized in comprising dissolved volatile solids of which at least 25% by weight comprise any combination of acetate, butyrate, ethanol, formate, lactate and/or propionate, optionally followed by (iv). anaerobic digestion of the bioliquid to produce biomethane.

Following some period of enzymatic hydrolysis and concurrent microbial fermentation, MSW provided at a non-water content between 10 and 45% is transformed such that biogenic or "fermentable" components become liquefied and microbial metabolites accumulate in the aqueous phase. After some period of enzymatic hydrolysis and concurrent microbial fermentation, the liquefied, fermentable parts of the waste are separated from non-fermentable solids. The liquefied material, once separated from non-fermentable solids, is what we term a "bio-degradable slurry." In some embodiments, at least 40% of the non-water content of this bio-degradable slurry comprises dissolved volatile solids, or at least 35%, or at least 30%, or at least 25%. In some embodiments, at least 25% by weight of the dissolved volatile solids in the biodegradable slurry comprise any combination of acetate, butyrate, ethanol, formate, lactate, and/or propionate, or at least 30%, or at least 35% or at least 40%. In some embodiments, at least 70% by weight of the dissolved volatile solids comprises lactate, or at least 60%, or at least 50%, or at least 40%, or at least 30%, or at least 25%.

In some embodiments, separation of non-fermentable solids from liquefied, degradable parts of the MSW so as to produce a bio-degradable slurry characterized in comprising dissolved volatile solids of which at least 25% by weight comprise any combination of acetate, butyrate, ethanol, formate, lactate and/or propionate is conducted in less than 16 hours after the initiation of enzymatic hydrolysis, or in less than 18 hours, or in less than 20 hours, or in less than 22 hours, or in less than 24 hours, or in less than 30 hours, or in less than 34 hours, or in less than 36 hours, or between 36 and 48 hours, or between 48 and 60 hours, or between 60 and 72 hours.

Separation of liquefied, degradable parts of the waste from non-degradable solids can be achieved by a variety of means. In some embodiments, this may be achieved using any combination of at least two different separation operations, including but not limited to screw press operations, ballistic separator operations, vibrating sieve operations, or other separation operations known in the art. In some embodiments, the non-degradable solids separated from bio-degradable parts of the waste comprise on average at least about 20% of the dry weight of the processed MSW, or at least 25%, or at least 30%. In some embodiments, the non-degradable solids separated from degradable parts of the processed waste comprise on average at least 20% by dry weight of recyclable materials, or at least 25%, or at least 30%, or at least 35%. In some embodiments, separation using at least two separation operations produces a bio-degradable slurry that comprises at least 0.15 kg volatile solids per kg MSW processed, or at least 0.10. It will be readily understood by one skilled in the art that the inherent biogenic composition of MSW is variable. Nevertheless, the figure 0.15 kg volatile solids per kg MSW processed reflects a total capture of biogenic material in typical unsorted MSW of at least 80% by dry weight. The calculation of kg volatile solids captured in the bio-degradable slurry per kg MSW processed can be estimated over a time period in which total yields and total MSW processed are determined. For a given period, the average production of biogenic slurry obtained can be calculated=kg slurry/H; the average throughput of MSW is calculated=kg MSW/H; the average VS content of the slurry is analysed and the result expressed as VS % of total mass; the kg VS is calculated as kg slurry/H*VS %=kg VS/H Then kg VS/H/kg MSW/H=kg VS/kg MSW.

In some embodiments, after separation of non-degradable solids from liquefied, fermentable parts of the MSW is achieved to produce a bio-degradable slurry, the slurry may be subject to post-fermentation under different conditions, including different temperature or pH.

The term "dissolved volatile solids" as used here refers to a simple measurement calculated as follows: A sample of bio-degradable slurry is centrifuged at 6900 g for 10 minutes in a 50 ml Falcon tube to produce a pellet and a supernatant. The supernatant is decanted and the wet weight of the pellet expressed as a percentage fraction of the total initial weight of the liquid sample. A sample of supernatant is dried at 60 degrees for 48 hours to determine dry matter content. The volatile solids content of the supernatant sample is determined by subtracting from the dry matter measurement the ash remaining after furnace burning at 550° C. and expressed as a mass percentage as dissolved volatile solids in %. The dry matter content of the pellet is determined by drying at 60 degrees C. for 48 hours. The liquid part of the pellet being (1-dry matter of the pellet) is expressed as a mass percentage of the pellet. The composition of the liquid part of the pellet is estimated to be similar to the supernatant. Thus the total dissolved volatile solids of the sample is the sum of the dissolved volatile solids of the supernatant and the (mass percentage of the liquid part of the pellet)×(the dissolved volatile solid of the supernatant).

In some embodiments the invention provides compositions and methods for biomethane production. The preceding detailed discussion concerning embodiments of methods of processing MSW, including details concerning compositional features of the bio-degradable slurry obtained, may optionally be applied to embodiments providing methods and compositions for biomethane production. In some embodiments, any of the details concerning compositional features of bio-degradable slurry may be obtained by a process in which unsorted MSW subject to microbial fermentation is subject to separation of non-degradable solids to produce a bio-degradable slurry, which slurry is then subject to continued fermentation at a temperature within the range of 35 to 75 degrees C., or between 40 and 55 degrees C., or between 45 and 50 degrees C., at a pH within the range 4.2 to 6.0 for a time of between 1 and 72 hours. In some embodiments, this continued fermentation is supplemented in that bio-degradable material recovered by sieves or other systems such the material was not technically part of the initially recovered bio-degradable slurry, can be added to the slurry.

The metabolic dynamics of microbial communities engaged in anaerobic digestion are complex. See Supaphol et al. 2010; Morita and Sasaki 2012; Chandra et al. 2012. In typical anaerobic digestion (AD) for production of methane biogas, biological processes mediated by microorganisms achieve four primary steps—hydrolysis of biological macromolecules into constituent monomers or other metabolites; acidogenesis, whereby short chain hydrocarbon acids and alcohols are produced; acetogenesis, whereby available nutrients are catabolized to acetic acid, hydrogen and carbon dioxide; and methanogenesis, whereby acetic acid and hydrogen are catabolized by specialized archaea to methane and carbon dioxide. The hydrolysis step is typically rate-limiting See e.g. Delgenes et al. 2000; Angelidaki et al. 2006; Cysneiros et al. 2011.

Accordingly, it is advantageous in preparing substrates for biomethane production that these be previously hydrolysed through some form of pretreatment. In some embodiments, methods of the invention combine microbial fermentation with enzymatic hydrolysis of MSW as both a rapid biological pretreatment for eventual biomethane production as well as a method of sorting degradable organic components from otherwise unsorted MSW.

Biological pretreatments have been reported using solid biomethane substrates including source-sorted organic component of MSW. See e.g. Fdez-Guelfo et al. 2012; Fdez-Guelfo et al. 2011 A; Fdez-Guelfo et al. 2011 B; Ge et al. 2010; Lv et al. 2010; Borghi et al. 1999. Improvements in eventual methane yields from anaerobic digestion were reported as a consequence of increased degradation of complex biopolymers and increased solubilisation of volatile solids. However the level of solubilisation of volatile solids and the level of conversion to volatile fatty acids achieved by these previously reported methods do not even approach the levels achieved by methods of the invention. For example, Fdez-Guelfo et al. 2011 A report a 10-50% relative improvement in solubilisation of volatile solids achieved through various biological pretreatments of pre-sorted organic fraction from MSW—this corresponds to final absolute levels of solubilisation between about 7 to 10% of volatile solids. In contrast, methods of the invention produce liquid biomethane substrates comprising at least 40% dissolved volatile solids.

Two-stage anaerobic digestion systems have also been reported in which the first stage process hydrolyses biomethane substrates including source-sorted organic component of MSW and other specialized biogenic substrates. During the first anaerobic stage, which is typically thermophilic, higher chain polymers are degraded and volatile fatty acids produced. This is followed by a second stage anaerobic stage conducted in a physically separate reactor in which methanogenesis and acetogenesis dominate. Reported two-stage anaerobic digestion systems have typically utilized source-sorted, specialized biogenic substrates having less than 7% total solids. See e.g. Supaphol et al. 2011; Kim et al. 2011; Lv et al. 2010; Riau et al. 2010; Kim et al. 2004; Schmit and Ellis 2000; Lafitte-Trouque and Forster 2000; Dugba and Zhang 1999; Kaiser et al. 1995; Harris and Dague 1993. More recently, some two stage AD systems have been reported which utilize source-sorted, specialized biogenic substrates at levels as high as 10% total solids. See e.g. Yu et al. 2012; Lee et al. 2010; Zhang et al. 2007. Certainly none of the reported two-stage anaerobic digestion systems has ever contemplated use of unsorted MSW as a substrate, much less in order to produce a high solids liquid biomethane substrate. Two stage anaerobic digestion seeks to convert solid substrates, continuously feeding additional solids to and continuously removing volatile fatty acids from the first stage reactor.

In some embodiments, the method of producing biomethane comprises the steps of (i). providing an liquid biomethane substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate, (ii). transferring the liquid substrate into an anaerobic digestion system, followed by (iii). conducting anaerobic digestion of the liquid substrate to produce biomethane.

In some embodiments, the invention provides a liquid biomethane substrate produced by microbial fermentation and hydrolysis of municipal solid waste (MSW), or of pretreated lignocellusic biomass, alternatively, comprising enzymatically hydrolysed and microbially fermented MSW, or comprising enzymatically hydrolysed and microbially fermented pretreated lignocellulosic biomass characterized in that at least 40% by weight of the non-water content exists as dissolved volatile solids, which dissolved volatile solids comprise at least 25% by weight of any combination of acetate, butyrate, ethanol, formate, lactate and/or propionate.

In some embodiments, the invention provides an organic liquid biogas substrate produced by microbial fermentation and hydrolysis of municipal solid waste (MSW) characterized in that at least 40% by weight of the non-water content exists as dissolved volatile solids, which dissolved volatile solids comprise at least 25% by weight of any combination of acetate, butyrate, ethanol, formate, lactate and/or propionate.

In some embodiments, the invention provides a method of producing biogas comprising the steps of (i). providing a liquid biogas substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate, (ii). transferring the liquid substrate into an anaerobic digestion system, followed by (iii). conducting anaerobic digestion of the liquid substrate to produce biomethane.

As used herein the term "anaerobic digestion system" refers to a fermentation system comprising one or more reactors operated under controlled aeration conditions in which methane gas is produced in each of the reactors comprising the system. Methane gas is produced to the extent that the concentration of metabolically generated dissolved methane in the aqueous phase of the fermentation mixture within the "anaerobic digestion system" is saturating at the conditions used and methane gas is emitted from the system.

In some embodiments, the "anaerobic digestion system" is a fixed filter system. A "fixed filter anaerobic digestion system" refers to a system in which an anaerobic digestion consortium is immobilized, optionally within a biofilm, on a physical support matrix.

In some embodiments, the liquid biomethane substrate comprises at least 8% by weight total solids, or at least 9% total solids, or at least 10% total solids, or at least 11% total solids, or at least 12% total solids, or at least 13% total solids. "Total solids" as used herein refers to both soluble and insoluble solids, and effectively means "non-water content." Total solids are measured by drying at 60° C. until constant weight is achieved.

In some embodiments, microbial fermentation of MSW is conducted under conditions that discourage methane production by methanogens, for example, at pH of 6.0 or lower, or at pH less than 5.8, or at pH less than 5.6, or at pH less than 5.5. In some embodiments, the liquid biomethane substrate comprises less than saturating concentrations of dissolved methane. In some embodiments, the liquid biomethane substrate comprises less than 15 mg/L dissolved methane, or less than 10 mg/L, or less than 5 mg/L.

In some embodiments, prior to anaerobic digestion to produce biomethane, one or more components of the dissolved volatile solids may be removed from the liquid biomethane substrate by distillation, filtration, electrodialysis, specific binding, precipitation or other means well known in the art. In some embodiments, ethanol or lactate may be removed from the liquid biomethane substrate prior to anaerobic digestion to produce biomethane.

In some embodiments, a solid substrate such as MSW or fiber fraction from pretreated lignocellulosic biomass, is subject to enzymatic hydrolysis concurrently with microbial fermentation so as to produce a liquid biomethane substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate. In some embodiments, a liquid biomethane substrate having the above mentioned properties is produced by concurrent enzymatic hydrolysis and microbial fermentation of liquefied organic material obtained from unsorted MSW by an autoclave process. In some embodiments, pretreated lignocellulosic biomass can be mixed with enzymatically hydrolysed and microbially fermented MSW, optionally in such manner that enzymatic activity from the MSW-derived bioliquid provides enzymatic activity for hydrolysis of the lignocellulosic substrate to produce a composite liquid biomethane substrate derived from both MSW and pretreated lignocellulosic biomass.

"Soft lignocellulosic biomass" refers to plant biomass other than wood comprising cellulose, hemicellulose and lignin. Any suitable soft lignocellulosic biomass may be used, including biomasses such as at least wheat straw, corn stover, corn cobs, empty fruit bunches, rice straw, oat straw, barley straw, canola straw, rye straw, sorghum, sweet sorghum, soybean stover, switch grass, Bermuda grass and other grasses, bagasse, beet pulp, corn fiber, or any combinations thereof. Lignocellulosic biomass may comprise other lignocellulosic materials such as paper, newsprint, cardboard, or other municipal or office wastes. Lignocellulosic biomass may be used as a mixture of materials originating from different feedstocks, may be fresh, partially dried, fully dried or any combination thereof. In some embodiments, methods of the invention are practiced using at least about 10 kg biomass feedstock, or at least 100 kg, or at least 500 kg.

Lignocellulosic biomass should generally be pretreated by methods known in the art prior to conducting enzymatic hydrolysis and microbial pre-conditioning. In some embodiments, biomass is pretreated by hydrothermal pretreatment. "Hydrothermal pre-treatment" refers to the use of water, either as hot liquid, vapor steam or pressurized steam comprising high temperature liquid or steam or both, to "cook" biomass, at temperatures of 120° C. or higher, either with or without addition of acids or other chemicals. In some embodiments, lignocellulosic biomass feedstocks are pretreated by autohydrolysis. "Autohydrolysis" refers to a pretreatment process in which acetic acid liberated by hemicellulose hydrolysis during pre-treatment further catalyzes hemicellulose hydrolysis, and applies to any hydrothermal pre-treatment of lignocellulosic biomass conducted at pH between 3.5 and 9.0.

In some embodiments, hydrothermally pretreated lignocellulosic biomass may be separated into a liquid fraction and a solid fraction. "Solid fraction" and "Liquid fraction" refer to fractionation of pretreated biomass in solid/liquid separation. The separated liquid is collectively referred to as "liquid fraction." The residual fraction comprising considerable insoluble solid content is referred to as "solid fraction." Either the solid fraction or the liquid fraction or both combined may be used to practice methods of the invention or to produce compositions of the invention. In some embodiments, the solid fraction may be washed.

Example 1. Bio-Degradable Capture in a Biogenic Slurry Obtained by Microbial Hydrolysis and Fermentation of MSW without Supplemental Cellulase Activity from Isolated Enzyme Preparations Experiments were conducted at the REnescience demonstration plant at Amager resource center (ARC), Copenhagen, Denmark. A schematic drawing showing principle features of the plant is shown in FIG. 1. The concept of the ARC REnescience Waste Refinery is to sort MSW into four products. A biogenic slurry suitable for biomethane production or other processes, inerts (glass and sand) for recycling and both a "two dimensional" (2D) and a "three dimensional" (3D) fraction of inorganic materials suitable for RDF production as well as for recycling of metals, plastic and wood.

MSW from urban areas is collected as-is in plastic bags. The MSW is transported to the REnescience Waste Refinery where it is stored in a silo until processing. Depending on the character of the MSW a sorting step can be installed in front of the REnescience system to take out oversize particles (above 500 mm).

As shown in FIG. 1, a stream of unsorted MSW is heated and its non-water content adjusted by addition of heated aqueous solution. In previous incarnations of REnescience process, we have relied on cellulase activity provided by isolated enzyme preparations to facilitate rapid degradation of the biodegradable component. We have previously added isolated enzyme preparations to the heated waste at an appropriate non-water content. The waste, with added enzymes, was then previously incubated in a reactor termed an "enzyme reactor" similar to that described in WO2011/032557, featuring a chamber that rotates on a substantially horizontal axis, equipped with attachments on its inner surface that form a spiral array, which moves MSW continuously from the input to the output end. Depending on the degree to which the reactor is filled, and depending on the size of the reactor, the average "residence time" of MSW within the reactor can be controlled. The reactor was equipped with heating elements such that an appropriate temperature could be maintained.

While continuously introducing MSW into the reactor and continuously removing partially degraded MSW from the reactor, a certain average residence time is obtained. Partially degraded MSW removed from the reactor is then subject to two distinct separation steps. First, a ballistic separator having 40 mm sieves is applied to produce a biogenic slurry stream, as well as a 3D non-degradable fraction and a 2D non-degradable fraction. Second, the 2D non-degradable fraction is further subject to de-watering using a screw press, with recovery of additional biogenic slurry that is, in turn, blended with the slurry obtained from the ballistic separator step.

The obtained biogenic slurry is then subject to further "fine" separation using two vibrating sieves, the first having 8 mm sieves, which separates out primarily non-degradable contaminants. The second vibrating sieve, having 3 mm sieves, typically separates out larger fibers, which comprise a considerable amount of bio-degradable material. After passing through the 3 mm sieve, the obtained biogenic slurry is stored in a large tank that is equipped with load cells, permitting an accurate recording of the mass of biogenic slurry obtained within a given time period.

The de-watered solid 2D fraction is then subject to a counter-current washing train to both clean the 2D fraction and also recover additional bio-degradable material that would otherwise be lost—The de-watered solid 2D fraction is then subject to a two-stage counter-current washing train in drums to both clean the 2D fraction and also recover additional bio-degradable material that would otherwise be lost. Details are provided in FIG. 1, which shows the water flows in the system. Fresh water is applied to washing 3D non-degradable material recovered from the ballistic separator in a simple drum. This wash water then is used as "clean" water which is fed into the second of two identical washing units so as to provide counter-current washing—the "clean" new water encounters the "cleanest" trash while consecutively more dirty water is applied to incoming "dirtier" trash. The washing train works as follows: the dirty 2D enters a drum in the first washing unit, where the waste is mixed with the counter-current washing water and mechanically mixed. Additionally the dirty wash water is subjected to sieve filtration having 0.04 to 0.08 mm sieves, to remove fibres, which typically comprise primarily bio-degradable material. Sand and heavy material is also removed by sedimentation and a screw conveyer in the bottom of each washing unit. The fraction removed is mostly sand/glass/heavy plastic/and other inorganics. After the first wash, the waste is moved by screw auger into a second washing unit, which is identical to the first. The wash water from the first wash unit typically has between 1-4% by weight TS whereas the wash water from the second wash unit typically has 0.5-3.0% by weight.

The wash waters, comprising some bio-degradable material recovered from the MSW as well as associated microorganisms, were then stored in a "buffer" tank. Aqueous solution from this "buffer" tank was then previously used to adjust the non-water content of incoming MSW. Previously we have typically first heated the solution from the "buffer" tank by applying steam, then mixing the heated solution with incoming MSW so as to simultaneously heat it to an appropriate temperature and also adjust the non-water content.

As is explained in examples presented subsequently to this example 1, we have previously determined that the inoculation of incoming MSW provided by the re-circulated washing waters enhances what we term bio-degradable capture that is achieved with the assistance of enzymatic hydrolysis using isolated cellulase preparations. By "bio-degradable capture," we mean the mass of volatile solids which is captured in the biogenic slurry, which is typically expressed as kg VS (volatile solids)/kg MSW processed.

In this experiment, we sought to test how effective bio-degradable capture would be if we did not apply any isolated enzyme preparation, but instead simply applied an inoculum of microorganisms naturally present in the MSW, to achieve a rapid degradation by microbial hydrolysis and fermentation.

For this purpose, we fitted the "buffer" tank, from which recirculated wash water solution is drawn to adjust the non-water content of incoming MSW, with a heat exchanger system, in order to be used as a fermenter maintaining a temperature of 45 degrees C., to promote bacterial growth. The "buffer" tank is equipped with an effective agitation system comprising a centre mounted vertical axle equipped with two sets of vanes attached to the axle. The two sets of vanes reach two-third of the tank diameter and are attached at a height on the axle corresponding to one-fourth of the distance from the bottom of the tank and three-fourths of the distance from the bottom of the tank. In order to avoid heating the "inoculum" drawn from the buffer tank/fermenter in such manner as might harm the micro-organisms, we used different procedures for heating the incoming MSW compared with the normal procedures used when applying isolated enzyme preparations.

The seventeen (17) day trial documented in this example was split up in five sections as shown in Table 2.

TABLE 2

Time course of the microbial hydrolysis and fermentation trial.

| Time (hours) | Added enzyme % | Comment |
|---|---|---|
| 0-153 | 0.9% | First enzyme run |
| 153-207 | | maintenance |
| 207-250 | 0% | Rise time without enzymes |
| 250-319 | 0% | Microbial fermentation only |
| 319-390 | 0.9% | Second enzyme run |

Unsorted MSW obtained from Copenhagen, Denmark was loaded continuously in to the REnescience demo plant. The isolated enzyme preparation used was a commercially available cellulase preparation optimized for conversion of lignocellulosic biomass and provided by NOVOZYMES™ under the trade name CELLIC CTEC 3™. For periods in which isolated cellulase preparation was used, an amount corresponding to 9 g of enzyme preparation was added for each kg of incoming MSW (0.9% by weight).

The settings for the operation was as follows for both periods in which isolated commercial enzyme preparation was added:
  Introduced an incoming MSW stream into the enzyme reactor at the rate 280 kg MSW/h
  Adjusted the non-water content of the incoming MSW stream by adding a solution of re-circulated wash water, which had been stored in the buffer tank at ambient temperature, then heated to approximately 75 degrees C. in the water heater at the rate 560 L water/h
  Introduced CTEC 3™ to the incoming MSW stream at 0.9% by weight corresponding to cellulase activity of approximately 670 FPU per L water content of the wetted MSW
  Ran the enzyme reactor so as to achieve an average retention time of approximately 18 hours at approximately 50° C., with pH adjusted using CaCO₃ to within the range pH 4.5-5.

During the "maintenance" period, the reactor was stopped. At the end of this period, approximately 2000 kg of contents were removed from the enzyme reactor before proceeding with continuous operation in the "no enzymes" period.

The period referred to as "rise time" without enzymes refers to the period during which residual CTEC3 was removed from the system.

The settings for the operation during the period without enzymes (i.e., both for "rise time" and "microbial fermentation only") was as follows:
  Introduced an incoming MSW stream into the enzyme reactor/microbial fermenter at the rate 130 kg MSW/h
  Adjusted the non-water content of the incoming MSW stream by adding an inoculum, comprising a solution of re-circulated wash water drawn from the buffer tank/fermenter, which was maintained at 45 degrees C. and continuously agitated using a the agitator described above running at about 30 rpm, and in which substrates had been added to promote bacterial growth and cellulase enzyme expression, including approximately 1% by weight yeast extract, approximately 1% by weight mixed glucose/sucrose, and approximately 1% by weight of microcrystalline cellulose (tradename AVI- CEL™). This "inoculum" was drawn through the water heater maintained at approximately 45 degrees C. at the rate 260 L water/h Ran the enzyme reactor/microbial fermenter (NOTE explain retention time) so as to achieve an average retention time of approximately 36 hours at approximately 45° C., with pH adjusted using $CaCO_3$ to within the range 4.5-5.

Samples were obtained at selected time points at the following places:

The biogenic slurry obtained after passing through the 3 mm sieve, which is termed "EC12B"

Material retained by the 8 mm sieve

Material retained by the 3 mm sieve

Material retained by Fibre sieve 1 applied to washing waters

Material retained by Fibre sieve 2 applied to washing waters

Washing water sampled after clearing the Fibre sieves 2D non-degradable fraction 3D non-degradable fraction Inert bottom fraction from both washing units The production of biogenic slurry was measured with load cells on the storage tank. The input flow of fresh waters was measured with flowmeters. The other fractions were separately weighed on a scale in such manner that total mass flows for any given time period could be accounted for.

For purposes of analysis of contents, samples were also obtained at selected time points from EC12B, from the buffer tank/fermenter, and from the enzyme reactor/microbial fermentation reactor. These samples were boiled so as to stop microbial and enzymatic activity.

FIG. 2 shows the sum of the microbial metabolites lactate, acetate and ethanol, expressed as a concentration in grams per liter, in samples of biogenic slurry obtained at various time points. As shown, during the first period with added cellulase activity, between hours 1 and 153, the level of microbial metabolites gradually rises until becoming relatively stable at about 35 g/L. During the period with microbial fermentation only, between hours 250 and 319, the level of metabolites was somewhat lower but stable at about 27-30 g/L. During the second period with added cellulase activity, between hours 319 and 390, the level of metabolites appears to be increased relative to the first period with added cellulase activity to between 35-40 g/L.

These results indicate, on the one hand, that it may be advantageous to include some supplemental cellulase activity with microbial fermentation. On the other hand, these results also indicate that the inoculum used was sufficient to promote rapid degradation of the MSW using only microbial fermentation.

FIG. 3 shows bio-degradable capture in kg TS (Total solids)/kg MSW for various time periods. Normally organic capture is determined in terms of volatile solids (VS). These samples were taken and results can be provided post-filing. Here results are presented in terms of TS, which includes ash content.

FIG. 3(A) shows bio-degradable capture in kg TS/kg MSW in samples of biogenic slurry obtained after passing through the 3 mm sieve termed "EC12B." For a given period, the average production of biogenic slurry obtained after passing through the 3 mm sieve termed "EC12B" is calculated=kg slurry/H; the average throughput of MSW is calculated=kg MSW/H; the average VS content of the slurry is analysed and the result expressed as VS % of total mass; the kg VS is calculated as kg slurry/H*VS %=kg VS/H Then kg VS/H/kg MSW/H=kg VS/kg MSW. During the period with microbial fermentation only, between hours 250 and 319, figures were corrected so as not to count the mass of special substrates added to the buffer tank/fermenter. As shown, during the first period with added cellulase activity, between hours 1 and 153, the level of bio-degradable capture in the biogenic slurry obtained after the 3 mm sieve was about 0.21-0.25 kg TS/kg MSW. During the period with microbial fermentation only, between hours 250 and 319, the level of "organic capture" in the biogenic slurry obtained after the 3 mm sieve was clearly diminished to about 0.10 to 0.15 kg TS/kg MSW. During the second period with added cellulase activity, between hours 319 and 390, the level of bio-degradable capture in the biogenic slurry obtained after the 3 mm sieve was similar to that observed during the first period with added cellulase activity, at about 0.21-0.25 kg TS/kg MSW.

FIG. 3(B) shows "total bio-degradable capture" in kg TS/kg MSW, combining both TS obtained in samples of biogenic slurry obtained after passing through the 3 mm sieve termed "EC12B" as well as TS obtained in the fibre fractions retained by the 3 mm sieve and by the Fibre sieves 1 and 2 applied to washing waters. During the period with microbial fermentation only, between hours 250 and 319, figures were corrected so as not to count the mass of special substrates added to the buffer tank/fermenter. As shown, during the first period with added cellulase activity, between hours 1 and 153, the level of "total bio-degradable capture" was only slighter higher than the level of bio-degradable capture in the liquid. During the period with microbial fermentation only, between hours 250 and 319, the level of "total bio-degradable capture" was much increased compared with capture in the liquid only, to levels approximately the same as achieved with added cellulase activity. During the second period with added cellulase activity, between hours 319 and 390, the level of "total bio-degradable capture" was similar to that observed during the first period with added cellulase activity.

These results indicate that, while added cellulase activity clearly facilitates a more complete degradation of the MSW during the short retention time prior to separation of non-degradable solids, nevertheless microbial fermentation alone can provide sufficient degradation of the MSW during a similarly short retention time so as to permit essentially equivalent "bio-degradable capture" in biological sorting of MSW.

This is particularly significant in that the biogenic slurry obtained using added commercial cellulase activity does not retain much activity following separation of non-degradable solids. This effect possibly arises from a substantially different mode of cellulase catalysis in the case of activity secreted by living organisms in real life, compared with the activities of the genetically engineered, secreted products that have been "harvested" and provided as CTEC3™. In previous trials at the demonstration plant, we have examined the various fractions described above, seeking to identify the fate of the added commercial cellulase activity. The levels of cellulase activity (FPU) observed in the biogenic slurry obtained after the 3 mm sieve termed "EC12B" were typically less than 0.5% of those observed in the enzyme reactor prior to separation of non-degradable materials.

In contrast, biogenic slurry obtained using only microbial fermentation can be expected to retain a very high level of microbially-derived cellulase activity, to the extent that it retains a high level of live cells.

Accordingly, in contrast with CTEC3™-dependent degradation, microbial fermentation permits the simple expedient of post-fermentation of the biogenic slurry, prior to biomethane production or other uses. In post-fermentation, "bio-degradable capture" retained by the various sieves is mixed with biogenic slurry and allowed to continue to ferment at an appropriate temperature.

Samples of biogenic slurry obtained at selected time points during the microbial fermentation period were analysed for dissolved solids. The volatile solids content of the supernatant sample was determined by subtracting from the dry matter measurement the ash remaining after furnace burning at 550° C. and expressed as a mass percentage as dissolved volatile solids in %. The dry matter content of the pellet is determined by drying at 60 degrees C. for 48 hours. The liquid part of the pellet being (1-dry matter of the pellet) expressed as a mass percentage of the pellet. The composition of the liquid part of the pellet is estimated to be similar to the supernatant. Thus the total dissolved volatile solids of the sample is the sum of the dissolved volatile solids of the supernatant and the (mass percentage of the liquid part of the pellet)×(the dissolved volatile solid of the supernatant). Results of the analysis are shown in Table 3. Lactate, acetate and ethanol concentrations are shown as overall weight %.

Jensen et al., 2010 based on Riber et al. 2009). Composition of the complete model waste was as follows:

| | % of model MSW (wet weight) |
|---|---|
| Animal | 23 |
| Vegetable | 81.6 |
| Cellulosic | 53.2 |

The cellulosic fraction consists of cardboard (coated and non coated), clean paper, advertisements, gift wrappings and more. The animal fraction consists of protein and fats from poultry, swine and beef. The vegetable fractions contain fruits, vegetables, and non edible parts such as shelled green pea pods.

The model waste was stored in aliquots at −20° C. and thawed overnight at 4° C. The model waste has a dry matter content of 28.4% (3.52 g model waste was added to yield 1 g dry matter (DM)). In addition, for each type of substrate, CELLIC CTEC3™ (VDNI0009, NOVOZYMES A/S, Bagsvaerd, Denmark) (CTec3) was applied at a dosage of 32

TABLE 3

Analysis of biogenic slurry.

| Hour | Dissolved VS % of total VS | Dissolved VS % of total TS | w % Dissolved VS | w % Lactate | w % Acetate | w % Ethanol | Sum: lactate, acetate, ethanol |
|---|---|---|---|---|---|---|---|
| 259 | 50.12 | 32.09 | 4.32 | 2.140 | 0.569 | 0.074 | 2.782 |
| 271 | 48.49 | 30.98 | 4.08 | | | | |
| 284 | 50.06 | 32.11 | 4.47 | 2.265 | 0.583 | 0.109 | 2.957 |
| 296 | 45.19 | 24.88 | 3.77 | 2.172 | 0.536 | 0.109 | 2.818 |
| 308 | 46.88 | 26.90 | 3.79 | 2.113 | 0.531 | 0.108 | 2.752 |

As shown, as a percentage of total volatile solids, the dissolved solids content of the biogenic slurry obtained using microbial fermentation alone was consistently between 40-50%. This indicates that microbial fermentation alone is sufficient to substantially degrade MSW so as to render the bio-degradable content susceptible of recovery in a biological sorting operation such as is described here. The slurry obtained as described was pumpable at all time periods during the microbial fermentation.

Example 2. Characterization of Microbially-Derived Cellulase Activity and Other MSW-Degrading Activities Expressed by Microbial Inoculum During the trial described in Example 1, a liquid sample from the buffer tank/fermenter tank (microbial inoculum) was withdrawn at hour 245. While this sample was taken slightly before the complete wash-out of residual CTEC3 activity, the residual CTEC activity in the buffer tank/fermenter at this point could not have been greater than 8 FPU/L in a worst-case estimate. From the time the sample was withdrawn until the experiment was started, 5.5 hours elapsed. 20 ml of the microbial inoculum was added to a 1 g dry substrate. The substrates were; tissue paper from 100% new paper pulp (LOMELETTER™), the cellulosic fraction from model waste and complete model waste. The model waste was prepared using fresh produce to comprise the "organic" fraction (defined as the cellulosic, animal and vegetable fractions) of municipal solid waste (prepared as in mg/g dry matter in the substrates, to compare with the extent of hydrolysis achieved by the microbial inoculum.

The cellulase activity of the CTEC3 was measured previously by the method reported in Ghose, T. K., *Measurement of cellulase activities*. Pure & Appl. Chem., 1987. 59(2): p. 257-268, and found to be 179 FPU/g of enzyme preparation. Accordingly the dose used in these experiments corresponds to approximately 5.7 FPU/g DM or, expressed in terms of the reaction volume, approximately 286 FPU/L.

To adjust and maintain the pH at 5 during the reaction with added CTEC3, a sodium acetate buffer (0.05M) was applied to make up the total volume to 20 g. Each reaction was done in triplicate, and one reaction of each substrate was incubated in parallel with only buffer added (substrate blank).

The reactions were incubated for 24 hours on a Stuart Rotator SB3 (turning at 4 RPM) placed in a heating cabinet (Binder, GmBH, Tuttlingen, Germany) set to 45° C. The tubes were then removed from the incubator and photographed. Since the physical structure of the samples appeared partially dissolved, the tubes were shaken vigorously by hand for approx. 2 seconds and once more photographed.

The tubes were then centrifuged at 1350 g for 10 minutes at 4° C. The supernatant was then decanted off, the supernatant and pellet were dried for 2 days at 60° C. in the heating cabinet. The weight of dried material was recorded and used to calculate the distribution of dry matter. The conversion of dry matter in the samples was calculated based on these numbers. As a control, a sample of microbial inoculum (solids content of 4.54%±0.06) was incubated without substrate to assess the background release of solids (33.9%±0.8). The conversion of solids from the substrates added by microbial inoculum was corrected by subtracting contribution of solids to the liquid fraction from the microbial inoculum itself. The relatively high background in these samples possibly overestimates the background observed in samples containing added substrate. This high background might include considerable contribution from cell mass which, in the absence of additional food source, returned to a soluble form during the course of the experiment, in contrast with the form of a living organism, which readily precipitates in these experimental conditions. For all substrates, addition of the microbial inoculum resulted in a higher release of solids than this background release of solid, indicating partial hydrolysis of the substrates by the microbial inoculum.

FIG. 4 shows comparative degradation of cellulosic substrates and model MSW by microbial inoculum and as assisted by CTEC3. As shown, with a clean cellulosic substrate such as tissue paper, CTEC3 clearly provides a more extensive degradation at the given dose level. Using the comparative degradation of tissue paper as an estimate of cellulase activity, the microbial inoculum is shown to exhibit approximately ⅙ of activity exhibited by CTEC3. The microbial-derived cellulase activity expressed by the microbial inoculum can thus be estimated as (⅙)*(286 FPU/L) or approximately 48 FPU/L within the 24 hour incubation time frame.

It should be noted that the precise mechanisms whereby microbial-derived cellulase activity is provided are not known. Without wishing to be bound by theory, it appears to us that contact with substrate induces expression of cellulase activity in a manner that is effectively "local" to the donor organism and effectively emerges during the course of the incubation. To the extent that this is correct, the microbially-derived cellulase activity will primarily "follow" the live cells.

The CTEC3 samples are also shown to provide a more extensive degradation of model MSW. Here, however, substrate blank degradation is high, suggesting that some microbial activity may also have contributed to the CTEC3 degradation.

Ironically, notwithstanding much lower levels of cellulase activity per se in FPU/L, the microbial inoculum is shown to achieve levels of degradation of the cellulosic fraction of model MSW that are comparable to levels achieved using CTEC3.

FIG. 5 shows a photograph taken after shaking of three tubes to which cellulosic fraction of model MSW were added as substrate, showing the comparative appearance at the end of incubation. As shown, the cellulosic fraction is indeed approximately equivalently degraded in comparing the CTEC3 and inoculum samples. It has been previously reported in lactic acid fermentations with simultaneous hydrolysis using isolated cellulase preparations, see Schmidt and Padukone 1997, that typical cellulase activities at levels as high as 25 FPU/g DM digest glossy magazine paper and other coated paper, as well as newsprint, with less than half the efficiency that they can digest clean paper. The results shown here suggest that some enzyme activities in addition to cellulase activity may be expressed by the microbial inoculum or its progeny which contribute to degradation of the cellulosic fraction of model MSW.

Example 3. Characterization of LAB Bacterial Counts

During the trial described in Example 1, samples from the buffer tank/fermenter (microbial inoculum) as well as samples from the biogenic slurry obtained after the 3 mm sieve termed "EC12B" were removed at various time points during the period from hour 235 to 319.

Aliquots from the samples were removed and dry matter content determined by drying at room temperature (so as to avoid damage to DNA content). The unfrozen samples obtained in 50 ml tubes then frozen with 50% by weight glycerol added.

Cell counts were determined by quantitative PCR (qPCR). 5 ml of the glycerol-suspended cells were suspended in 5 ml of sterile-filtered H2O. An aliquot was filtered onto a filter and the solids concentration was determined. DNA was extracted from the filtered cell mass using a FastDNA™ kit (MP BIOMEDICALS™). The number of the 16S rRNA gene copy numbers in the extracted DNA was quantified by qPCR analysis with universal 16S rRNA gene primers. The method quantifies only Bacteria and not Archaea. Bacterial cell number were calculated based on these data assuming an average of 3.0 copy numbers of the 16s rRNA gene per live cell. Calculated bacterial cell numbers were then related to the dry matter (total solids) concentration in the samples. The calculated CFU/g DM were used to estimate CFU/L where the microbial inoculum was, on average, 3.95% by weight DM during the time period and where the biogenic slurry was, on average, 11.98% by weight DM.

The bacterial counts per g dry matter for the samples are shown in Table 4, along with an estimate of CFU/L.

TABLE 4

Live bacterial counts in microbial inoculum and biogenic slurry.

| | CFU/g TS | | CFU/L | |
|---|---|---|---|---|
| Hour | Inoculum | biogenic slurry | Inoculum | biogenic slurry |
| 235 | $5.40 \times 10^{10}$ | $4.10 \times 10^{9}$ | $2.13 \times 10^{12}$ | $4.84 \times 10^{11}$ |
| 283 | $1.00 \times 10^{10}$ | $4.00 \times 10^{9}$ | $3.95 \times 10^{11}$ | $4.72 \times 10^{11}$ |
| 307 | $5.00 \times 10^{10}$ | $2.00 \times 10^{9}$ | $1.98 \times 10^{12}$ | $2.36 \times 10^{11}$ |

These results clearly demonstrate that the live bacterial cells follow the biogenic slurry. Accordingly, it can be expected that the biogenic slurry itself can provide an effective inoculum and will provide microbially-derived cellulase activity for post-fermentation of biodegradable fibers collected by the various sieves, as well as for undissolved solids retained in the slurry at the time of the initial separation of non-degradable solids.

These results indicate that microbial hydrolysis and fermentation induced by the microbial inoculum resulted in relatively stationary growth during the course of hydrolysis and fermentation and that the obtained biogenic slurry could be expected to provide an appropriate inoculum for post-fermentation with fibers recovered on the various sieves.

It is generally expected that LAB will comprise a major proportion of the microbial population the evolves where MSW is simply incubated at temperatures between 37 and 50 degrees C. See e.g Akao et al. 2007a; Akao et al. 2007b; Sakai et al. 2000; Sakai et al. 2004. Live LAB bacteria counts on the order of $10^{10}$ CFU/L can be routinely obtained within about 12 hours in lactic acid fermentation of model kitchen waste, without added enzyme activity. See Sakai et al. 2000 and Sakai et al. 2004. Generation doubling times of lactic acid bacteria identified in examples presented subsequently to this example 3 are on the order of 4 to 5 hours. See Liong and Shaw 2005.

The proportion of the live bacteria in the samples which represent lactic acid bacteria can be decisively determined from the 16s RNA measurements described in Example 4. However, these results will not be available until post-filing. In all previous experimental trials at the REnescience demonstration plant involving inoculation of incoming MSW with re-circulated washing waters, where samples were properly frozen with glycerol to protect the organisms, *Lactobacillus* species emerged as predominant, invariably comprising greater than 90% of total detected organisms in samples from the enzyme reactor/microbial fermentation reactor and from the biogenic slurry. Accordingly, where we estimate that *Lactobacillus* species (which are likely not the only LAB present) comprise at least 90% of the live cells, levels of LAB in the aqueous phase within the enzyme reactor/microbial fermentation reactor in Example 1 were maintained during the course of hydrolysis and fermentation to at least $2.1 \times 10^{10}$ CFU/L.

Example 4. Identification of Microorganisms Providing Hydrolysis and Fermentation in Example 1

Samples of the biogenic slurry obtained after passing through the 8 mm sieve termed "EC12B", and of the liquid (microbial inoculum) from the buffer tank/fermenter termed "EA02" as well as samples from the water heater "LB01" were taken during the test at hours 101 and 125, during the first period with added CTEC3, at hour 245, at the end of the "rise time without CTEC3," at hour 269, during the period with microbial fermentation only, and at hours 341 and 365, during the second period with added CTEC3.

The liquid samples were frozen in 20% glycerol and stored at −20° C. for the purpose of performing 16S rDNA analysis to identify the microorganisms. This analysis is well known in the art and is widely used for identification and phylogenic analysis of prokaryotes based on the 16S component of the small ribosomal subunit. The frozen samples were shipped on dry ice to GATC Biotech AB, Solna, SE where the 16S rDNA analysis was performed (GATC_Biotech).

The analysis comprised: extraction of genomic DNA, amplicon library preparation using the universal primers primer pair spanning the hypervariable regions V1 to V3 27F: AGAGTTTGATCCTGGCTCAG/534R: ATTACCGCGGCTGCTGG; 507 bp length), PCR tagging with GS FLX adaptors, sequencing on a Genome Sequencer FLX instrument to obtain 104.000-160.000 number of reads pr. sample. The resulting sequences will be queried in a BlastN against the rDNA database from Ribosomal Database Project (Cole et al., 2009). The database contains good quality sequences with at least 1200 bp in length and a NCBI taxonomic association. The current release (RDP Release 10, Updated on Sep. 19, 2012) contains 9,162 bacteria and 375 archaeal sequences The BLAST results will be filtered to remove short and low quality hits (sequence identity ≥90%, alignment coverage ≥90%).

The project number for the samples registered at GATC was NG-7116. Results will be available post-filing.

Example 5. Concurrent Microbial Fermentation Improves Organic Capture by Enzymatic Hydrolysis of Unsorted MSW Using Isolated Enzyme Preparations Laboratory bench scale reactions were conducted with bio-degradable slurry sample from the test described in example 9.

The model MSW substrate for laboratory scale reactions was prepared using fresh produce to comprise the organic fraction (defined as the cellulosic, animal and vegetable fractions) of municipal solid waste (prepared as described in Jensen et al., 2010 based on Riber et al. 2009).

The model MSW was stored in aliquots at −20° C. and thawed overnight at 4° C. The reactions were done in 50 ml centrifuge tubes and the total reaction volume was 20 g. Model MSW was added to 5% dry matter (DM) (measured as the dry matter content remaining after 2 days at 60° C.).

The cellulase applied for hydrolysis was Cellic CTec3 (VDNI0003, Novozymes A/S, Bagsvaerd, Denmark) (CTec3). To adjust and maintain the pH at pH5, a citrate buffer (0.05M) was applied to make up the total volume to 20 g.

The reactions were incubated for 24 hours on a Stuart Rotator SB3 (turning at 4 RPM) placed in a heating oven (Binder GmBH, Tuttlingen, Germany). Negative controls were done in parallel to assess background release of dry matter from the substrate during incubation. Following incubation the tubes were centrifuged at 1350 g for 10 minutes at 4° C. The supernatant was then decanted off, 1 ml was removed for HPLC analysis and the remaining supernatant and pellet were dried for 2 days at 60° C. The weight of dried material was recorded and used to calculate the distribution of dry matter. The conversion of DM in the model MSW was calculated based on these numbers.

The concentrations organic acids and ethanol were measured using an UltiMate 3000 HPLC (Thermo Scientific Dionex) equipped with a refractive index detector (Shodex® RI-101) and a UV detector at 250 nm. The separation was performed on a Rezex RHM monosaccharide column (Phenomenex) at 80° C. with 5 mM $H_2SO_4$ as eluent at a flow rate of 0.6 ml/min. The results were analyzed using the Chromeleon software program (Dionex).

To evaluate the effect of concurrent fermentation and hydrolysis, 2 ml/20 g of the bioliquid from the test described in example 5 (sampled on December 15th and 16th) was added to the reactions with or without CTec3 (24 mg/g DM). Conversion of DM in MSW.

The conversion of solids was measured as the content of solids found in the supernatant as a percent of total dry matter. FIG. 5 shows conversion for MSW blank, isolated enzyme preparation, microbial inoculum alone, and the combination of microbial inoculum and enzyme. The results shows that addition of EC12B from example 5 resulted in significantly higher conversion of dry matter compared to the background release of dry matter in the reaction blank (MSW Blank) (Students t-Test p<0.0001). Concurrent microbial fermentation induced by addition of the EC12B sample and enzymatic hydrolysis using CTec3 resulted in significantly higher conversion of dry matter compared to the reaction hydrolysed only with CTec3 and the reactions added EC12B alone (p<0.003).

HPLC Analysis of Glucose, Lactate, Acetate and EtOH.

The concentration of glucose and the microbial metabolites (lactate, acetate and ethanol) measured in the supernatant are shown in FIG. 6. As shown, there was a low background concentration of these in the model MSW blank and the lactic acid content presumably comes from bacteria indigenous to the model MSW since the material used to create the substrate was in no way sterile or heated to kill bacteria. The effect of addition of CTec3 resulted in an increase in glucose and lactic acid in the supernatant. The highest concentrations of glucose and bacterial metabolites was found in the reactions where EC12B bioliquid from example 9 was added concurrently with CTec3. Concurrent fermentation and hydrolysis thus improve conversion of dry matter in model MSW and increase the concentration of bacterial metabolites in the liquids.

REFERENCES

Jacob Wagner Jensen, Claus Felby, Henning Jørgensen, Georg Ørnskov Rønsch, Nanna Dreyer Nørholm. Enzymatic processing of municipal solid waste. Waste Management. December 2010; 30(12):2497-503.

Riber, C., Petersen, C., Christensen, T. H., 2009. Chemical composition of material fractions in Danish household waste. Waste Management 29, 1251-1257.

Example 6. Concurrent Microbial Fermentation Improves Organic Capture by Enzymatic Hydrolysis of Unsorted MSW Using Isolated Enzyme Preparations Tests were performed in a specially designed batch reactor shown in FIG. 8, using unsorted MSW with the aim to validate results obtained in lab scale experiments. The experiments tested the effect of adding an inoculum of microorganisms comprising bioliquid obtained from example 7 bacteria in order to achieve concurrent microbial fermentation and enzymatic hydrolysis. Tests were performed using unsorted MSW.

MSW used for small-scale trials were a focal point of the research and development at REnescience. For the results of trials to be of value, waste was required to be representative and reproducible.

Waste was collected from Nomi Holstebro in March 2012. Waste was unsorted municipal solid waste (MSW) from the respective area. Waste was shredded to 30×30 mm for use in small-scale trials and for collection of representative samples for trials. Theory of sampling was applied to shredded waste by sub-sampling of shredded waste in 22-liter buckets. Buckets were stored in a freezer container at −18° C. until use. "Real waste" was composed of eight buckets of waste from the collection. The content of these buckets was remixed and resampled in order to ensure that variability between repetitions was as low as possible.

All samples were run under similar conditions regarding water, temperature, rotation and mechanical effect. Six chambers were used: three without inoculation and three with inoculation. Designated non-water content during trial was set to 15% non-water content by water addition. Dry matter in the inoculating material was accounted for so the fresh water addition in the inoculated chambers was smaller. 6 kg of MSW was added to each chamber, as was 84 g CTEC3, a commercial cellulase preparation. 2 liter of inoculum was added to inoculated chambers, with a corresponding reduction in added water.

pH was kept at 5.0 in the inoculated chambers and at pH 4.2 in the non-inoculated chambers using respectively addition of 20% NaOH for increasing pH and 72% $H_2SO_4$ for decreasing the pH. The lower pH in the non-inoculated chamber helped ensure that intrinsic bacteria would not flourish. We have previously shown that, using the enzyme preparation used, CTEC3™, in the context of MSW hydrolysis, no difference in activity can be discerned between pH 4.2 and pH 5.0 The reaction was continued at 50 degrees C. for 3 days, with the pilot reactor providing constant rotary agitation.

At the end of the reaction, the chambers were emptied through a sieve and bioliquid comprising liquefied material produced by concurrent enzymatica hydrolysis and microbial fermentation of MSW.

Dry matter (TS) and volatile solids (VS) were determined Dry Matter (DM) method: Samples were dried at 60° C. for 48 hours. The weight of the sample before and after drying was used to calculate the DM percentage.

$$\text{Sample } DM \ (\%) \frac{\text{Sample dry weight (g)}}{\text{Wet weight (g)}} \times 100$$

Volatile Solids Method:

Volatile solids are calculated and presented as the DM percentage subtracted the ash content. The ash content of a sample was found by burning the pre-dried sample at 550° C. in a furnace for a minimum of 4 hours. Then the ash was calculated as:

Sample Ash percentage of dry matter:

$$\frac{\text{Sample ash weight (g)}}{\text{Sample dry weight (g)}} \times 100$$

Volatile Solids percentage:

$$(1 - \text{sample ash percentage}) \times \text{Sample } DM \text{ percentage}$$

Results were as shown below. As shown, a higher total solids content was obtained in bioliquid obtained in the inoculated chambers, indicating that concurrent microbial fermentation and enzymatic hydrolysis were superior to enzymatic hydrolysis alone.

|  | Bioliquid | |
| --- | --- | --- |
|  | TS (kg) | VS (kg) |
| Std. low lactate | 1.098 | 0.853 |
| Pode. High lactate | 1.376 | 1.041 |
| Added pode. TS + VS | TS | VS |
| Kg | 0.228 | 0.17 |

|  | Bioliquid | | | |
| --- | --- | --- | --- | --- |
| Produced | TS (kg) | stdev | VS (kg) | stdev |
| std. low lactate | 1.098 | 0.1553 | 0.853 | 0.116 |
| Pode. High lactate | 1.148 | 0.0799 | 0.869 | 0.0799 |
|  | more % |  | more % |  |
| std. low lactate |  |  |  |  |
| Pode. High lactate | 4.5579 |  | 1.8429 |  |

|  |  | % more |
| --- | --- | --- |
| Sum metabolics (lactate acetate and ethanol) produced | | |
| std avg. | 92.20903 g/L |  |
| pode avg. | 342.6085 g/L | 271.5564 |
| Sum metabolics (lactate acetate and ethanol) "captured" | | |
| std avg. (low lac) | 189.6075 g/L |  |
| pode avg. (high lac) | 461.6697 g/L | 143.4871 |

Example 7. Concurrent Microbial Fermentation Improves Organic Capture by Enzymatic Hydrolysis of Unsorted MSW Using Isolated Enzyme Preparations Experiments were conducted at the REnescience demonstration plant placed at Amager resource center (ARC), Copenhagen, Denmark. A schematic drawing showing principle features of the plant is shown in FIG. 1. The concept of the ARC REnescience Waste Refinery is as described generally in example 1.

REnescience technology as tested in this example comprises three steps.

The first step is a mild heating (pretreatment, as shown in FIG. 4) of the MSW by hot water to temperatures in the range of 40-75° C. for a period of 20-60 minutes. This heating and mixing period opens plastic bags and provides adequate pulping of degradable components preparing a more homogenous organic phase before addition of enzymes. Temperature and pH are adjusted in the heating period to the optimum of isolated enzyme preparations which are used for enzymatic hydrolysis. Hot water can be added as clean tap water or as washing water first used in the washing drums and then recirculated to the mild heating as indicated in FIG. 1.

The second step is enzymatic hydrolysis and fermentation (liquefaction, as shown in FIG. 4). In the second step of the REnescience process enzymes are added and optionally selected microorganisms. The enzymatic liquefaction and fermentation is performed continuously at a residence time of app. 16 hours, at the optimal temperature and pH for enzyme performance. By this hydrolysis and fermentation the biogenic part of the MSW is liquefied in to a bio-liquid high in dry matter in between non-degradable materials. pH is controlled by addition of $CaCO_3$.

The third step of REnescience technology as practiced in this example is a separation step where the bio-liquid is separated from the non-degradable fractions. The separation is performed in a ballistic separator, washing drums and hydraulic presses. The ballistic separator separates the enzymatic treated MSW into the bio-liquid, a fraction of 2D non-degradable materials and a fraction of 3D non-degradable materials. The 3D fraction (physical 3 dimensional objects as cans and plastic bottles) does not bind large amounts of bio-liquid, so a single washing step is sufficient to clean the 3D fraction. The 2D fraction (textiles and foils as examples) binds a significant amount of bio-liquid. Therefore the 2D fraction is pressed using a screw press, washed and pressed again to optimize the recovery of bio-liquid and to obtain a "clean" and dry 2D fraction. Inert material which is sand and glass is sieved from the bio-liquid. The water used in all the washing drums can be recirculated, heated and then used as hot water in the first step for heating.

The trial documented in this example was split up in three sections as shown in table 5

TABLE 5

| Time (hours) | Rodalon | Tap water/Washing water to mild heating |
|---|---|---|
| 27-68 | + | tap water |
| 86-124 | − | tap water |
| 142-187 | − | washing water |

In a 7-day trial, unsorted MSW obtained from Copenhagen, Denmark was loaded continuously by 335 kg/h in to the REnescience demo plant. In the mild heating was added 536 kg/h water (tap water or washing water) heated to app. 75° C. before entering the mild heating reactor. Temperature is hereby adjusted to app. 50° C. in the MSW and pH is adjusted to app. 4.5 by addition of $CaCO_3$.

In the first section the surface-active anti-bacterial agent Rodalon™ (benzyl alkyl ammonium chloride) was included in the added water at 3 g active ingredient per kg MSW.

In the liquefaction reactor is added app. 14 kg of Cellic Ctec3 (commercially available cellulase preparation from Novozymes) per wet ton of MSW. The temperature was kept in the range from 45-50° C. and the pH was adjusted in the range from 4.2-4.5 by adding $CaCO_3$. Enzyme reactor retention time is app. 16 hours.

In the separation system of ballistic separator, presses and washing drums the obtained bio-degradable slurry is separated from non-degradable materials.

Wash waters were selectively either poured out, recording organic content, or recirculated and re-used to wet incoming MSW in the mild heating. Recirculation of wash water has the effect of accomplishing bacterial inoculation using organisms thriving at 50° C. reaction conditions to levels higher than those initially present. In the process scheme used, recirculated wash water were first heated to approximately 70° C., in order to bring incoming MSW to a temperature appropriate for enzymatic hydrolysis, in this case, about 50° C. Particularly in the case of lactic acid bacteria, heating to 70 C has previously been shown to provide a selection and "inducement" of thermal tolerance expression.

Samples were obtained at selected time points at the following places:
- The bio-liquid leaving the small sieve, which is termed "EC12B"
- The bio-liquid in the storage tank
- Washing water after the whey sieves
- 2D fraction
- 3D fraction
- Inert bottom fraction from both washing units The production of bio-degradable slurry was measured with load cells on the storage tank. The input flow of fresh waters was measured with flowmeters, the recycled or drained washing waste was measured with load cells.

Bacterial counts were examined as follows: Selected samples of bioliquid were diluted 10-fold in the SPO (peptone salt solution) and 1 ml of the dilutions are plated at sowing depth on beef Extract Agar (3.0 g/L of Beef extract (Fluke, Cas.: B4888), 10.0 g/L Tryptone (Sigma, cas. no.: T9410), 5.0 g/L NaCl (Merck, cas. no, 7647-14-5), 15.0 g/L agar (Sigma, cas. no. 9002-18-0)). The plates were incubated at 50 degrees, respectively. aerobic and anaerobic atmosphere. Anaerobic cultivation took place in appropriate containers were kept anaerobic by gassing with Anoxymat and adding iltfjernende letters (AnaeroGen from Oxoid, cat. no AN0025A). The aerobic colonies were counted after 16 hours and again after 24 hours. The anaerobic growing bacteria were quantified after 64-72 hours.

FIG. 9 shows total volatile solids content in bio-degradable slurry samples at EC12B as kg per kg MSW processed. Points estimates were obtained at different time points during the experiment by considering each of the three separate experimental periods as a separate time period. Thus, a point estimate during period 1 (Rodalon) is expressed relative to the mass balances and material flows during period 1. A shown in FIG. 5, during period 1, which was initiated after a prolonged stop due to complications in the plant, total solids captured in bio-degradable slurry are seen to drop steadily, consistent with a slight anti-bacterial effect of Rodalon™. During period 2, total captured solids returns to slightly higher levels. During period 3, where recirculation provides an effective "inoculation" of incoming MSW, bio-degradable slurry capture kg VS/kg affald rises to considerably higher levels around 12%.

For each of the 10 time points shown in FIG. 9, bioliquid (EC12B) samples were taken and total solids, volatile solids, dissolved volatile solids, and concentrations of the presumed bacterial metabolites acetate, butyrate, ethanol, formate, and propionate were determined by HPLC. These results including glycerol concentrations are shown in Table 6 below. All percentages given are overall weight percent.

sequences with at least 1200 bp in length and a NCBI taxonomic association. Only BLAST hits ≥95% identity were included.

The sampled bio-degradable slurry was directly transferred to analysis without freezing before DNA extraction.

TABLE 6

Analysis of bio-degradable slurry samples.

| Time hours | Total solids % | VS % | Dissolved VS % | Lactate % | Formic acid % | Acetate % | Propionate % | Ethanol % | Glycerol % |
|---|---|---|---|---|---|---|---|---|---|
| 45 | 10.30 | 8.69 | 7.00 | 3.22 | 0.00 | 0.35 | 0.00 | 0.12 | 0.4165 |
| 53 | 9.77 | 8.22 | 6.62 | 3.00 | 0.00 | 0.42 | 0.00 | 0.17 | 0 |
| 63 | 9.31 | 7.74 | 6.07 | 2.74 | 0.09 | 0.41 | 0.03 | 0.17 | 0.415 |
| 67 | 8.66 | 7.15 | 5.54 | 2.82 | 0.00 | 0.39 | 0.03 | 0.20 | 0.475 |
| 88 | 9.57 | 7.97 | 6.02 | 3.24 | 0.00 | 0.31 | 0.04 | 0.13 | 0.554 |
| 116 | 10.57 | 8.90 | 6.77 | 3.27 | 0.01 | 0.25 | 0.00 | 0.11 | 0.5635 |
| 130 | 9.93 | 8.33 | 6.43 | 3.39 | 0.00 | 0.25 | 0.00 | 0.11 | 0 |
| 141 | 12.07 | 9.08 | 6.76 | 4.16 | 0.00 | 0.28 | 0.00 | 0.14 | 0.6205 |
| 159 | 11.30 | 8.68 | 6.33 | 4.63 | 0.00 | 0.31 | 0.00 | 0.11 | 0 |
| 166 | 11.04 | 8.17 | 5.72 | 4.50 | 0.00 | 0.32 | 0.03 | 0.12 | 0.646 |
| 181 | 11.76 | 8.75 | 6.11 | 5.48 | 0.12 | 0.37 | 0.00 | 0.11 | 1.38 |
| 188 | 11.20 | 8.05 | 6.20 | 5.40 | 0.00 | 0.40 | 0.00 | 0.11 | 0 |

For bio-degradable slurry samples taken at each of the ten time points, FIG. 10 shows both live bacterial counts determined under aerobic conditions and shown as counts per ml and also the weight percent "bacterial metabolites" (meaning the sum of acetate, butyrate, ethanol, formate, and proprionate) expressed as a percentage of dissolved volatile solids. As shown, the weight percent bacterial metabolites clearly increases with increased bacterial activity, and is associated with increased capture of solids in the bioliquid.

Example 8. Identification of Microorganisms Contributing to the Concurrent Fermentation in Example 7

Samples of bioliquid obtained from example 7 were analysed for microbial composition.

The microbial species present in the sample were identified by comparing their 16S rRNA gene sequences with 16S rRNA gene sequences of well-characterized species (reference species). The normal cut-off value for species identification is 97% 16S rRNA gene sequence similarity with a reference species. If the similarity is below 97%, it is most likely a different species.

The resulting sequences were queried in a BlastN against the NCBI databases. The database contains good quality A total of 7 bacterial species were identified (FIG. 11) and 7 species of Archea were identified. In some cases the bacterial species the subspecies could not be assigned (L. acidophilus, L. amylovorus, L. sobrius, L. reuteri, L. frumenti, L. fermentum, L. fabifermentans, L. plantarum, L. pentosus)

Example 9. Detailed Analysis of Organic Capture Using Concurrent Microbial Fermentation and Enzymatic Hydrolysis of Unsorted MSW Using Isolated Enzyme Preparations The REnescience demonstration plant described in example 1 and in example 7 was used to make a detailed study of total organic capture using concurrent bacterial fermentation and enzymatic hydrolysis of unsorted MSW.

Trash from Copenhagen was characterized by Econet to determine its content.

Waste analysis have been analysed to determine the content and variation. A large sample of MSW was delivered to Econet A/S, which performed the waste analyses. The primary sample was reduced to a sub sample around 50-200 kg. This subsample was the sorted by trained personnel into 15 different waste fractions. The weight of each fraction was recorded and a distribution calculated.

TABLE 7

Waste composition as (%) of total, analysed by Econet during the 300 hours test

| | Sample: | | | | | | | | | | |
|---|---|---|---|---|---|---|---|---|---|---|---|
| | 1. % | 2. % | 3. % | 4. % | 5. % | 6. % | 7. % | 8. % | 9. % | average % | Standard deviation |
| Plastic packaging | 5.1 | 6.7 | 8.0 | 4.9 | 6.2 | 2.5 | 6.2 | 7.5 | 6.4 | 5.9 | 1.64 |
| Plastic foil | 10.8 | 8.6 | 10.7 | 7.9 | 10.1 | 7.8 | 8.8 | 8.5 | 9.5 | 9.2 | 1.13 |
| Other plastic | 0.7 | 0.8 | 0.5 | 0.7 | 1.0 | 0.7 | 1.6 | 0.4 | 0.9 | 0.8 | 0.33 |
| Metal | 2.5 | 3.6 | 2.7 | 2.0 | 2.5 | 2.1 | 3.6 | 2.1 | 3.6 | 2.7 | 0.68 |
| Glass | 0.2 | 0.0 | 0.5 | 0.6 | 0.6 | 0.0 | 0.6 | 0.4 | 0.0 | 0.3 | 0.27 |
| Yard waste | 0.7 | 3.5 | 1.9 | 1.8 | 0.9 | 2.7 | 0.6 | 4.5 | 2.8 | 2.1 | 1.33 |
| WEEE (batteries etc.) | 0.7 | 0.1 | 0.6 | 0.4 | 0.7 | 0.8 | 1.1 | 0.1 | 0.5 | 0.6 | 0.33 |
| Paper | 14.8 | 8.3 | 13.3 | 8.8 | 10.5 | 5.6 | 10.2 | 12.6 | 12.4 | 10.7 | 2.86 |
| Plastic and cardboard packaging | 10.4 | 21.4 | 11.9 | 8.6 | 11.0 | 6.7 | 10.7 | 11.8 | 13.9 | 11.8 | 4.13 |

TABLE 7-continued

Waste composition as (%) of total, analysed by Econet during the 300 hours test

| | Sample: | | | | | | | | | | |
|---|---|---|---|---|---|---|---|---|---|---|---|
| | 1. % | 2. % | 3. % | 4. % | 5. % | 6. % | 7. % | 8. % | 9. % | average % | Standard deviation |
| Food waste | 19.8 | 15.6 | 25.9 | 27.6 | 26.3 | 24.5 | 24.5 | 23.3 | 18.0 | 22.8 | 4.09 |
| Diapers | 8.0 | 10.3 | 6.9 | 18.8 | 8.1 | 25.1 | 15.2 | 10.1 | 14.0 | 12.9 | 6.00 |
| Dirty paper | 8.5 | 6.7 | 7.3 | 7.4 | 8.5 | 8.6 | 7.9 | 5.7 | 6.3 | 7.4 | 1.03 |
| Fines | 9.7 | 2.5 | 4.2 | 2.1 | 4.5 | 4.7 | 2.7 | 7.0 | 4.9 | 4.7 | 2.40 |
| Other combustibles | 2.0 | 0.9 | 0.8 | 1.2 | 1.8 | 0.7 | 0.7 | 2.2 | 0.8 | 1.2 | 0.61 |
| Other non-combustibles | 6.2 | 11.1 | 5.0 | 7.3 | 7.2 | 7.6 | 5.6 | 3.7 | 6.2 | 6.7 | 2.07 |
| sum | 100 | 100 | 100 | 100 | 100 | 100 | 100 | 100 | 100 | 100.0 | |

The composition of waste varies from time to time, presented in table 7 is waste analysis result from different samples collected over 300 hours. the largest variation is seen en the fractions diapers plastic and cardboard packing and food waste which is all fractions that affect the content of organic material that can be captured.

Over the entire course of the "300 Hours Test," the average "captured" biodegradable material expressed as kg VS per kg MSW processed was 0.156 kg VS/kg MSW input.

Representative samples of bio-degradable slurry were taken at various time points during the course of the experiment, when the plant was in a period of stable operation. Samples were analysed by HPLC and to determine volatile solids, total solids, and dissolved solids as described in example 7. Results are shown in Table 8 below.

TABLE 8

Analysis of bioliquid samples.

| Time hours | Total solids % | VS % | Dissolved VS % | Formic acid % | Lactate % | Acetate % | Propionate % | Ethanol % | Glycerol % |
|---|---|---|---|---|---|---|---|---|---|
| 212 | 10.45 | 8.36 | 5.95 | 0.00 | 5.36 | 0.46 | 0.03 | 0.46 | 0.82 |
| 239 | 10.91 | 8.64 | 5.85 | 0.00 | 6.08 | 0.33 | 0.00 | 0.33 | 0.77 |
| 264.5 | 11.35 | 8.82 | 6.25 | 0.00 | 4.97 | 0.49 | 0.00 | 0.49 | 1.06 |
| 294 | 10.66 | 8.48 | 5.60 | 0.08 | 3.37 | 0.39 | 0.00 | 0.39 | 0.55 |

Example 10. Identification of Microorganisms Contributing to Concurrent Fermentation in Example 9

Note: In this example, the samples of material analysed for microorganism identification were frozen without glycerol. The results obtained are inconsistent with observed high lactate levels and with all other results obtained in all other tests where samples were frozen with added glycerol and are not believed to be accurate.

A sample of the biodegradable slurry "EC12B" was withdrawn during the test described in example 9 on Dec. 15 and 16, 2012 and stored at −20° C. for the purpose of performing 16S rDNA analysis to identify the microorganisms in the sample. The 16S rDNA analysis is widely used to identification and phylogenic analysis of prokaryotes based on the 16S component of the small ribosomal subunit. The frozen samples were shipped on dry ice to GATC Biotech AB, Solna, SE where the 16S rDNA analysis was performed (GATC_Biotech). The analysis comprised: extraction of genomic DNA, amplicon library preparation using the universal primers primer pair spanning the hypervariable regions V1 to V3 27F: AGAGTTTGATCCTG-GCTCAG/534R: ATTACCGCGGCTGCTGG; 507 bp length), PCR tagging with GS FLX adaptors, sequencing on a Genome Sequencer FLX instrument to obtain 104.000-160.000 number of reads pr. sample. The resulting sequences were then queried in a BlastN against the rDNA database from Ribosomal Database Project (Cole et al., 2009). The database contains good quality sequences with at least 1200 bp in length and a NCBI taxonomic association. The current release (RDP Release 10, Updated on Sep. 19, 2012) contains 9,162 bacteria and 375 archaeal sequences. The BLAST results were filtered to remove short and low quality hits (sequence identity 90%, alignment coverage 90%).

A total of 226 different bacteria were identified.

The predominant bacteria in the EC12B sample was *Paludibacter propionicigenes* WB4, a propionate producing bacteria (Ueki et al. 2006), which comprised 13% of the total bacteria identified. The distribution of the 13 predominant bacteria identified (*Paludibacter propionicigenes* W84, *Proteiniphilum acetatigenes, Actinomyces europaeus, Levilinea saccharolytica, Cryptanaerobacter phenolicus, Sedimentibacter hydroxybenzoicus, Clostridium phytofermentans* ISDg, *Petrimonas sulfuriphila, Clostridium lactatifermentans, Clostridium caenicola, Garciella nitratireducens, Dehalobacter restrictus* DSM 9455, *Marinobacter lutaoensis*) is shown in FIG. 11.

Comparing the bacteria identified at genus level showed that *Clostridium, Paludibacter, Proteiniphilum, Actinomyces* and *Levilinea* (all anaerobes) represented approximately half of the genera identified. The genus *Lactobacillus* comprised 2% of the bacteria identified. The predominant bacterial specie *P. propionicigenes* WB4 belong to the second most predominating genera (*Paludibacter*) in the EC12B sample.

The predominant pathogenic bacteria in the EC12B sample was *Streptococcus* spp., which comprised 0.028% of the total bacteria identified. There was not found any spore forming pathogenic bacteria in the bio-liquid.

*Streptococcus* spp. was the only pathogenic bacteria present in the bio-liquid in example 9. *Streptococcus* spp. is the bacteria with the highest temperature tolerance (of the non-spore forming) and D-value, which indicates that the amount of time needed at a given temperature to reduce the amount of living *Streptococcus* spp. cells tenfold, is higher than any of the other pathogenic bacteria reported by Déportes et al. (1998) in MSW. These results show that the conditions applied in example 9 are able to sanitize MSW during sorting in the REnescience process to a level where only *Streptococcus* spp. was present.

The competition between organism for nutrients, and the increased in temperature during the process will decrease the number of pathogenic organisms significantly and as shown above eliminate presence of pathogens in MSW sorted in the REnescience process. Other factors like pH, $a_w$, oxygen tolerance, $CO_2$, NaCl, and $NaNO_2$ also influence growth of pathogenic bacteria in bio-liquid. The interaction between the above mentioned factors, might lower the time and temperature needed to reduce the amount of living cells during the process.

Example 11. Detailed Analysis of Organic Capture Using Concurrent Microbial Fermentation and Enzymatic Hydrolysis Using Isolated Enzyme Preparations of Unsorted MSW Obtained from a Distant Geographic Location The REnescience demonstration plant described in example 7 was used to process MSW imported from the Netherlands. The MSW was found to have the following composition:

TABLE Y waste composition (5) of total, analysed by
Econet during the van Gansewinkel test.

|  | % |
|---|---|
| Plastic packaging | 5 |
| Plastic foil | 7 |
| Other plastic | 2 |
| Metal | 4 |
| Glass | 4 |
| Yard waste | 4 |
| WEEE (batteries etc) | 1 |
| Paper | 12 |
| Cardboard | 12 |
| Diapers | 4 |
| Dirty paper | 2 |
| Other combustibles | 15 |
| Other non-combustibles | 5 |
| Food waste | 13 |
| Fines | 9 |
| Total | 100 |

The material was subject to concurrent enzymatic hydrolysis and microbial fermentation as described in example 7 and 9 and tested for a plant run of 3 days. Samples of bio-degradable slurry obtained at various time points were obtained and characterized. Results are shown in Table 9. Percents given are total weight percent.

TABLE 9

Analysis of bioliquid.

| Time hours | Total solids % | VS % | Dissolved VS % | Lactate % | Formic acid % | Acetate % | Propionate % | Ethanol % | Glycerol % |
|---|---|---|---|---|---|---|---|---|---|
| 76 | 7.96 | 6.08 | 3.07 | 4.132 | 0.08 | 0.189 | 0 | 0.298 | 0.4205 |
| 95 | 9.19 | 6.99 | 6.66 | 6.943 | 0 | 0.352 | 0.034 | 0.069 | 0.6465 |

The dissolved VS has been corrected with 9% according to loss of lactate during drying.

Example 12. Biomethane Production Using Bioliquid Obtained from Concurrent Microbial Fermentation and Enzymatic Hydrolysis of Unsorted MSW Using Isolated Enzyme Preparations Bio-degradable slurry obtained in the experiment described in example 9 was frozen in 20 liter buckets and stored at −18° C. for later use. This material was tested for biomethane production using two identical well prepared fixed filter anaerobic digestion systems comprising an anaerobic digestion consortium within a biofilm immobilized on the filter support.

Initial samples were collected for both the feed and the liquid inside the reactor. VFA, tCOD, sCOD, and ammonia concentrations are determined using HACH LANGE cuvette tests with a DR 2800 Spectrophotometer and detailed VFAs were determined daily by HPLC. TSVS measurements are also determined by the Gravimetric Method. Gas samples for GC analysis are taken daily. Verification of the feed rate is performed by measuring headspace volume in the feed tank and also the amount of effluent coming out of the reactor. Sampling during the process was performed by collecting with a syringe of liquid or effluent."

Stable biogas production was observed using both digester systems for a period of 10 weeks, corresponding to between 0.27 and 0.32 L/g $CO_2$.

Feed of slurry was then discontinued on one of the two system and the return to baseline monitored, as shown in FIG. 13. Stable gas production level is shown by the horizontal line indicated as 2. The time point at which feed was discontinued is shown at the vertical lines indicated as 3. As shown, after months of steady operation, there remained a residual resilient material which was converted during the period indicated between the vertical lines indicated as 3 and 4. The return to baseline or "ramp down" is shown in the period following the vertical line indicated as 4. Following a baseline period, feed was again initiated at the point indicated by the vertical line indicated as 1. The rise to steady state gas production or "ramp up" is shown in the period following the vertical line indicated as 1.

Parameters of gas production from the bioliquid, including "ramp up" and "ramp down" measured as described are shown below.

| Parameter | Unit | Sample name 300 hour Amager waste |
|---|---|---|
| Feed rate | L/day | 1.85 |
| Total feed | Liter | 3.7 |
| Ramp-up time * | Hours | 15 |
| Ramp-down time ** | Hours | 4 |
| Burn-down time *** | Days | 4 |
| Gas production in stable phase **** | L/day | 122 |
| Total gas produced | L | 244 |
| $CH_4$ % | % | 60 |
| Total yield | Lgas/Lfeed | 66 |
| Gas from the easy convertible organics | % | 53 |
| Feed COD | g/L | 124 |
| Total COD feed-in | g | 459 |
| COD yield | Lgas/gCOD | 0.53 |
| Specific COD yield | L $CH_4$/gCOD | 0.32 |
| COD accounted for by mass balance | % of feed COD | 96 |
| COD to gas | g | 418 |
| COD to gas | % | 91 |

* Ramp-up time is the time from first feed till gas production seize to increase and stabilises. The ramp-up time indicates the level of easy convertible organics in the feed.
** Ramp-down time is the time from last feed till gas production seizes to fall steeply. The ramp-down time shows the gas production from easily convertible organics.
*** Burn-down is the time after the Ramp-down time until the gas production seizes totally at base level. The burn-down time shows the gas production from slowly convertible organics.
**** Corrected for background gas production of 2 L/day.

Example 13. Comparative Biomethane Production Using Bio-Degradable Slurry Obtained from Enzymatic Hydrolysis of Unsorted MSW Using Isolated Enzyme Preparations with and without Concurrent Microbial Fermentation "High lactate" and "low lactate" bio-degradable slurry obtained in example 6 were compared for biomethane production using the fixed filter anaerobic digestion system described in example 8. Measurements were obtained and "ramp up" and "ramp down" times were determined as described in example 11.

FIG. 14 shows "ramp up" and "ramp down" characterization of the "high lactate" bioliquid. Stable gas production level is shown by the horizontal line indicated as 2. The time point at which feed was initiated is shown at the vertical lines indicated as 1. The rise to steady state gas production or "ramp up" is shown in the period following the vertical line indicated as 1. The time point at which feed was discontinued is shown at the vertical line indicated as 3. The return to baseline or "ramp down" is shown in the period following the vertical line indicated as 3 to the period at the vertical line indicated by 4.

FIG. 15 shows the same characterization of the "low lactate" bioliquid, with the relevant points indicated as described for FIG. 14.

Comparative parameters of gas production from the "high lactate" and "low lactate" bioliquid, including "ramp up" and "ramp down" measured as described are shown below.

The difference in "ramp up"/"ramp down" times show differences in ease of biodegradability. The fastest bioconvertible biomasses will ultimately have the highest total organic conversion rate in a biogas production application. Moreover, the "faster" biomethane substrates are more ideally suited for conversion by very fast anaerobic digestion systems, such as fixed filter digesters.

As shown, the "high lactate" bioliquid exhibits a much faster "ramp up" and "ramp down" time in biomethane production.

| | | Sample name | |
|---|---|---|---|
| Parameter | Unit | High lactate Holstebro waste | Low lactate control Holstebro |
| Feed rate | L/day | 1.0 | 1.0 |
| Total feed | Liter | 2.83 | 3.95 |
| Ramp-up time * | Hours | 16 | 48 |
| Ramp-down time ** | Hours | 6 | 14 |
| Burn-down time *** | Days | 2 | 2 |
| Gas production in stable phase **** | L/day | 59 | 40 |
| Total gas produced | L | 115 | 140 |
| $CH_4$ % | % | 60 | 60 |
| Total yield | Lgas/Lfeed | 41 | 35 |
| Gas from the easy convertible organics | % | 86 | 82 |
| Feed COD | g/L | 106 | 90 |
| Total COD feed-in | g | 300 | 356 |
| COD yield | Lgas/gCOD | 0.38 | 0.39 |
| Specific COD yield | L $CH_4$/gCOD | 0.23 | 0.24 |
| COD accounted for by mass balance | % of feed COD | 91 | 95 |
| COD to gas | g | 197 | 240 |
| COD to gas | % | 66 | 68 |

* Ramp-up time is the time from first feed till gas production seize to increase and stabilises. The ramp-up time indicates the level of easy convertible organics in the feed.
** Ramp-down time is the time from last feed till gas production seizes to fall steeply. The ramp-down time shows the gas production from easily convertible organics.
*** Burn-down is the time after the Ramp-down time until the gas production seizes totally at base level. The burn-down time shows the gas production from slowly convertible organics.
**** Corrected for background gas production of 2 L/day.

Example 14. Biomethane Production Using Bio-Degradable Slurry Obtained from Concurrent Microbial Fermentation and Enzymatic Hydrolysis of Hydrothermally Pretreated Wheat Straw Using Isolated Enzyme Preparations Wheat straw was pretreated (parameters), separated into a fiber fraction and a liquid fraction, and then the fiber fraction was separately washed. 5 kg of washed fiber were then incubated in a horizontal rotary drum reactor with dose of Cellic CTEC3 with an inoculum of fermenting microorganisms consisting of bio-degradable slurry obtained from example 7. The wheat straw was subject to simultaneous hydrolysis and microbial fermentation for 3 days at 50 degrees.

This bioliquid was then tested for biomethane production using the fixed filter anaerobic digestion system described in example 11. Measurements were obtained for "ramp up" time as described in example 11.

FIG. 16 shows "ramp up" characterization of the hydrolysed wheat straw bioliquid. Stable gas production level is shown by the horizontal line indicated as 2. The time point at which feed was initiated is shown at the vertical lines indicated as 1. The rise to steady state gas production or "ramp up" is shown in the period following the vertical line indicated as 1.

Parameters of gas production from wheat straw hydrolysate bioliquid are shown below.

As shown, pretreated lignocellulosic biomass can also readily be used to practice methods of biogas production and to produce novel biomethane substrates of the invention.

| Parameter | Unit | Sample name Wheat hydrolysate + Bioliquid |
|---|---|---|
| Feed rate | L/day | 1 |
| Total feed | Liter | 1.2 |
| Ramp-up time * | Hours | 29 |
| Ramp-down time ** | Hours | N/A |
| Burn-down time *** | Days | N/A |
| Gas production in stable phase **** | L/day | 56 |
| Total gas produced | L | N/A |
| CH$_4$ % | % | 60 |
| Total yield | Lgas/Lfeed | N/A |
| Gas from the easy convertible organics | % | N/A |
| Feed COD | g/L | 144 |
| Total COD feed-in | g | 173 |
| COD yield | Lgas/gCOD | N/A |
| Specific COD yield | L CH$_4$/gCOD | N/A |
| COD accounted for by mass balance | % of feed COD | N/A |
| COD to gas | g | N/A |
| COD to gas | % | N/A |

\* Ramp-up time is the time from first feed till gas production seize to increase and stabilises. The ramp-up time indicates the level of easy convertible organics in the feed.
\*\* Ramp-down time is the time from last feed till gas production seizes to fall steeply. The ramp-down time shows the gas production from easily convertible organics.
\*\*\* Burn-down is the time after the Ramp-down time until the gas production seizes totally at base level. The burn-down time shows the gas production from slowly convertible organics.
\*\*\*\* Corrected for background gas production of 2 L/day.

Since *propionibacterium acidipropionici* is an anaerobe, the buffer applied in the reactions were this strain was applied, was purged using gaseous nitrogen and the live culture was inoculated to the reaction tubes inside a mobile anaerobic chamber (Atmos Bag, Sigma Chemical CO, St. Louis, Mo., US) also purged with gaseous nitrogen. The reaction tubes with *P. propionici* were closed before transferred to the incubator. The reactions were inoculated with 1 ml of either *P. propionici* or *L. amylophilus*.

The results displayed in table 10 clearly show that the expected metabolites were produced; propionic acid was detected in the reactions inoculated with *p. acidipropionic* while propionic acid was not detected in the control containing model MSW with or without CTec3. The concentration of lactic acid in the control reaction added only model MSW was almost the same as in the reactions added only *L. amylophilus*. The production of lactic acid in this control reaction is attributed to bacteria indigenous to the model MSW. Some background bacteria were expected since the individual components of the model waste were fresh produce, frozen, but not further sterilised in any way before preparation of the model MSW. When *L. amylophilus* was added concurrently with CTec3, the concentration of lactic acid was almost doubled (Table 10).

The positive effect on release of DM to the supernatant following hydrolysis was demonstrated as a higher DM conversion in the reactions added either *L. amylophilus* or *P. propionici* in conjunction with CTec3 (30-33% increase compared to the reactions added only CTec3).

TABLE 10

Bacterial cultures tested in lab scale alone or concurrently with enzymatic hydrolysis. The temperature, pH and CTec3 dosage 96 mg/g is shown. Control reactions with MSW in buffer with or without CTec3 were done in parallel to evaluate the background of bacterial metabolites in reaction. (Average and standard deviation of 4 reactions are shown except for the MSW control which were done as singles).
Nd. Not detected, below detection limit.

| Temperature | pH | Organism | CTec3 | Conversion of DM | Propionic acid (g/L) | Lactic acid (g/L) |
|---|---|---|---|---|---|---|
| 30° C. | 7 | Propionibacterium acidipropionici | 96 mg/g DM | 17.0 ± 1.0<br>40.8 ± 2.2 | 6.2 ± 1.8<br>3.7 ± 0.09 | |
| | | MSW control | 96 mg/g DM | 21<br>30.6 | Nd.<br>Nd. | |
| | 6.2 | Lactobacillus amylophilus | 96 mg/g DM | 19.7 ± 2.2<br>41.7 ± 6.5 | | 8.4 ± 0.8<br>21.2 ± 0.7 |
| | | MSW control | 96 mg/g DM | 21<br>32 | | 10.3<br>16.9 |

Example 15. Concurrent Microbial Fermentation and Enzymatic Hydrolysis of MSW Using Selected Organisms The concurrent microbial and enzymatic hydrolysis reactions using specific, monoculture bacteria were carried out in laboratory scale using model MSW (described in example 5) and the procedure described in following the procedure in example 5. The reaction conditions and enzyme dosage are specified in Table 10.

Live bacterial strains of *Lactobaccillus amylophiles* (DSMZ No. 20533) and *propionibacterium acidipropionici* (DSMZ No. 20272) (DSMZ, Braunsweig, Germany) (stored at 4° C. for 16 hours until use) were used as inoculum to determine the effect of these on the conversion of dry matter in model MSW with or without addition of CTec3. The major metabolites produced by these are lactic acid and propionic acid, respectively. The concentration of these metabolites were detected using the HPLC procedure (described in example 5).

Example 16. Identification of Microorganisms Contributing to Concurrent Fermentation in Example 11

Samples of the bioliquid "EC12B" and of the recirculated water "EA02" were taken during the test described in example 11 (sampling was done on March 21$^{st}$ and 22$^{nd}$). The liquid samples were frozen in 10% glycerol and stored at −20° C. for the purpose of performing 16S rDNA analysis to identify the microorganisms in the which is widely used to identification and phylogenic analysis of prokaryotes based on the 16S component of the small ribosomal subunit. The frozen samples were shipped on dry ice to GATC Biotech AB, Solna, SE where the 16S rDNA analysis was performed (GATC_Biotech). The analysis comprised:

extraction of genomic DNA, amplicon library preparation using the universal primers primer pair spanning the hypervariable regions V1 to V3 27F: AGAGTTTGATCCTG-GCTCAG/534R: ATTACCGCGGCTGCTGG; 507 bp length), PCR tagging with GS FLX adaptors, sequencing on a Genome Sequencer FLX instrument to obtain 104.000-160.000 number of reads pr. sample. The resulting sequences were then queried in a BlastN against the rDNA database from Ribosomal Database Project (Cole et al., 2009). The database contains good quality sequences with at least 1200 bp in length and a NCBI taxonomic association. The current release (RDP Release 10, Updated on Sep. 19, 2012) contains 9,162 bacteria and 375 archaeal sequences The BLAST results were filtered to remove short and low quality hits (sequence identity ≥90%, alignment coverage ≥90%).

In the samples EC12B-21/3, EC12B-22/3 and EA02B 21/3, EA02-22/3 a total of 452, 310, 785, 594 different bacteria were identified.

The analysis clearly showed, at a species level, that *Lactobacillus amylolyticus* was by far the most dominating bacterium accounting for 26% to 48% of the entire microbiota detected. The microbiota in the EC12B samples was similar; the distribution of the 13 predominant bacteria (*Lactobacillus amylolyticus* DSM 11664, *Lactobacillus delbrueckii* subsp. *delbrueckii*, *Lactobacillus amylovorus*, *Lactobacillus delbrueckii* subsp *indicus*, *Lactobacillus similis* JCM 2765, *Lactobacillus delbrueckii* subsp. *Lactis* DSM 20072, *Bacillus coagulans*, *Lactobacillus hamsteri*, *Lactobacillus parabuchneri*, *Lactobacillus plantarum*, *Lactobacillus brevis*, *Lactobacillus pontis*, *Lactobacillus buchneri*) was practically the same comparing the two different sampling dates.

The EA02 samples were similar to the EC12B although *L. amylolyticus* was less dominant. The distribution of the 13 predominant bacteria (*Lactobacillus amylolyticus* DSM 11664, *Lactobacillus delbrueckii* subsp *delbrueckii*, *Lactobacillus amylovorus*, *Lactobacillus delbrueckii* subsp. *Lactis* DSM 20072, *Lactobacillus similis* JCM 2765, *Lactobacillus delbrueckii* subsp. *indicus*, *Lactobacillus paraplantarum*, *Weissella ghanensis*, *Lactobacillus oligofermentans* LMG 22743, *Weissella beninensis*, *Leuconostoc gasicomitatum* LMG 18811, *Weissella soli*, *Lactobacillus paraplantarum*) was also similar with the exception of the presence of with the exception of the occurrence of *Pseudomonas extremaustralis* 14-3 in the 13 predominant bacterial species. This *Pseudomonas* found in EA02 (21/3) has previously been isolated from a temporary pond in *Antarctica* and should be able to produce polyhydroxyalkanoate (PHA) from both octanoate and glucose (Lopez et al. 2009; Tribelli et al., 2012).

Comparing the results at a genus level showed that *lactobacillus* comprised 56-94% of the bacteria identified in the samples Again the distribution across genera is extremely similar between the two sampling dates of EC12B and EA02. Interestingly, in the EA02 samples the genera *Weisella*, *Leuconostoc* and *Pseudomonas* are present to large extent (1.7-22%) while these are only found as minor constituents of the EC12B sample (>0.1%). *Weisella* and *Leuconostoc* both belong to the order lactobacillales, the same as the *lactobacillus*.

The predominant pathogenic bacteria in the EC12B and EA02 sampled during the test described in example 11 comprised 0.281-0.539% and 0.522-0.592%, respectively of the total bacteria identified. The predominant pathogenic bacteria in the EC12B samples were *Aeromonas* spp., *Bacillus cereus*, *Brucella* sp., *Citrobacter* spp., *Clostridium perfrigens*, *Klebsiells* sp., *Proteus* sp., *Providencia* sp., *Salmonella* spp., *Serratia* sp., *Shigellae* spp. and *Staphylococcus aureus* (see FIG. 3). No spore forming pathogenic bacteria were identified in the EC12B and EA02 described in example 11. The total amount of pathogen bacteria identified in both EC12B and EA02 was reduced during time, almost dismissing the amount of total bacteria in EC12B in one day.

In Déportes et al. (1998) an overview of the pathogens know to be present in MSW was made. The pathogens present in the MSW described in examples 7, 9 and 11 are shown in Table 11 (Déportes et al. (1998) and 16S rDNA analysis). In addition to the pathogens described by Déportes et al. (1998), *Proteua* sp. and *Providencia* sp. were both found in EC12B and EA02 sampled during the test described in example 11. Whereas the *Streptococcus* spp. the only pathogenic bacteria present in the bio-liquid in example 9, was not present here. This indicate that another bacterial community is present in EC12B and EA02 in example 11, which might be due to competition between organism for nutrients, and a slight decrease in temperature during the process which will favor the growth of another bacteria community.

TABLE 12

Overview of pathogens present in examples 7, 9 and 11

| Organism Bacteria | Optimal | Max (growth) | Temperature Bacteriosidal | Time req. [min] | D-value [min] | pH range Min | pH range Max | aw Min | Bio safetylevel | Sources Found in MSW | Ref on growing conditions |
|---|---|---|---|---|---|---|---|---|---|---|---|
| *Aeromonas* sp. | 37 | 55 | 55 | | 0.25 | | | 0.94 | 1-2 | (Déportes, et al.1998) | Rouf and Rigney 1971, Spinks et al 2006, |
| *Bacillus cereus* | 37 | 50 | 95 | 10 | | 4.8 | 9.3 | 0.951 | 2 | (Déportes, et al.1998) | Santos et al 1994 Lanciotti et al 2001 |
| *Brucella* sp. | | | | | | | | | 3 | (Déportes, et al.1998) | |
| *Citrobacter* sp. | | | 52.5 | 7 | | 4-5 | | 0.94 | 1-2 | (Déportes, et al.1998) | Verrips and Kwaps 1977, Smith and Bhagwat 2013, |
| *Clostridium perfringens* | 37 | 50 | 61 | 23 | | 5 | 8.5 | 0.95 | 2 | (Déportes, et al.1998) | Colavita et al 2003 Jay, J. M. 1991 |
| *Klebsiella* sp. | | | 55 | | 0.5 | <3 | | | 1-2 | (Déportes, et al.1998) | |
| *Salmonella* sp. | 37 | 45 | 55 | 2.5 | | 3.7 | 9.5 | 0.94 | 2-3 | (Déportes, et al.1998) | Jay, J. M. 1991, Spinks et al 2006 |
| *Serratia* sp. | | | 55 | 1.5 | | | | | 2 | (Déportes, et al.1998) | Spinks et al 2006 Spinks et al 2006 |
| *Shigellae* spp. | 37 | 48 | 60 | 1 | | 5 | 8 | — | 2-3 | (Déportes, et al.1998) | Jay, J. M. 1991 Francis, A. E. 1959 |

TABLE 12-continued

Overview of pathogens present in examples 7, 9 and 11

| Organism | Max | Temperature | Time req. | D-value | pH range | | aw | Bio | Sources Found in | Ref on |
| --- | --- | --- | --- | --- | --- | --- | --- | --- | --- | --- |
| Bacteria | Optimal | (growth) Bacteriosidal | [min] | [min] | Min | Max | Min | safetylevel | MSW | growing conditions |
| Staphylococcus aureus | 47.8 | | | | 4 | 9 | 0.86 | 2 | (Déportes, et al.1998) | |
| Streptococcus spp | | 65 | 20 | | | | | 2 | (Déportes, et al.1998) | |

Strain Identification and DSMZ Deposits

Samples of EA02 from March 21$^{st}$ and 22$^{nd}$ retrieved from the test described in example 7, were sent for plating at the Novo Nordic Centre for Biosustainability (NN Center) (Hoersholm, Denmark) with the purpose of identifying and obtaining monocultures of isolated bacteria. Upon arrival at the NN center, the samples were incubated overnight at 50° C., then plated on different plates (GM17, tryptic soy broth, and beef extract (GM17 agar: 48.25 g/L m17 agar, after 20 min. autoclaving added Glucose to final concentration at 0.5%, Tryptic soy agar: 30 g/L Tryptic soy broth, 15 g/L agar, Beef broth (Statens Serum Institute, Copenhagen, Denmark) added 15 g/l agarose) and grown aerobically at 50° C. After one day, the plates were visually inspected and selected colonies were re-streaked on the corresponding plates and send to DSMZ for identification.

The following strains isolated from the recirculated water from EA02 have been put in patent deposit at DMSZ, DSMZ, Braunsweig, Germany:

Identified Samples

Sample ID: 13-349 (*Bacillus safensis*) originating from (EA02-21/3), DSM 27312

Sample ID: 13-352 (*Brevibacillus brevis*) originating from (EA02-22/3), DSM 27314

Sample ID: 13-353 (*Bacillus subtilis* sp. *subtilis*) originating from (EA02-22/3), DSM 27315

Sample ID: 13-355 (*Bacillus licheniformis*) originating from (EA02-21/3), DSM 27316

Sample ID: 13-357 (*Actinomyces bovis*) originating from (EA02-22/3), DSM 27317

Not Identified Samples

Sample ID: 13-351 originating from (EA02-22/3), DSM 27313

Sample ID: 13-362A originating from (EA02-22/3), DSM 27318

Sample ID: 13-365 originating from (EA02-22/3), DSM 27319

Sample ID: 13-367 originating from (EA02-22/3), DSM 27320

REFERENCES

Cole, J. R., Wang, Q., Cardenas, E., Fish, J., Chai, B., Farris, R. J., & Tiedje, J. M. (2009). The Ribosomal Database Project: improved alignments and new tools for rRNA analysis. Nucleic acids research, 37 (suppl 1), (D141-D145).

GATC_Biotech supporting material. Defining the Microbial Composition of Environmental Samples Using Next Generation Sequencing. Version 1.

Tribelli, P. M., Iustman, L. J. R., Catone, M. V., Di Martino, C., Reyale, S., Méndez, B. S., López, N. I. (2012). Genome Sequence of the Polyhydroxybutyrate Producer *Pseudomonas extremaustralis*, a Highly Stress-Resistant Antarctic Bacterium. *J. Bacteriol.* 194(9):2381.

Nancy I. López, N. I., Pettinari, J. M., Stackebrandt, E., Paula M. Tribelli, P. M., Pötter, M., Steinbüchel, A., Méndez, B. S. (2009). *Pseudomonas extremaustralis* sp. nov., a Poly(3-hydroxybutyrate) Producer Isolated from an Antarctic Environment. Cur. Microbiol. 59(5):514-519.

The embodiments and examples are representative only and not intended to limit the scope of the claims.

LIST OF REFERENCES

Abe and Takagi (1990), "Simultaneous Saccharification and fermentation of cellulose to lactic acid", Biotechnology and Bioscience 37:93-96

Angelidaki, I. et al. (2006), "Enhanced biogas recovery by applying post-digestion in large-scale centralized biogas plants," Water Science & Technology 54(2):237-244

Akao et al. (2007a)"Effects of PH and temperature on products and bacterial community in I-lactate batch fermentation of garbage under unsterile condition" Water Research 41:2636-2642

Akao et al. (2007b) "Semi-continuous I-lactate fermentation of garbage without sterile condition and analysis of the microbial structure", Water research 41:1774-1780

Arriaga, S., et al. (2011), "Continuous production of hydrogen from oat straw hydrolysate in a biotrickling filter," International Journal of Hydrogen Energy 36:3442.

Asha et al. (2012), "Purification and Characterization of a thermophilic cellulose from a novel cellulolytic strain *Paenibacillus barcinonensi*"s, J. Microbiol. Biotechol. 22(11):1501-1509

Ballesteros, M. et al. (2010), "Ethanol production from the organic fraction obtained after thermal pretreatment of Municipal Solid Waste," Appl. Biochem. Biotechnol. 161:423-431

Bandounas L et al (2011), "Isolation and characterization of novel bacterial strains exhibiting ligninolytic potential", MNC Biotechnology, 11:94

Bendixen, H. (1994), "Safeguards against pathogens in Danish biogas plants," Water Science and Technology 30(12):171

Bilanin, M., et al. (1997), "Influence of fermented cereal and lactic acid and lactic acid bacteria concentrate on sewage sludge digestion," Environmental Technology 18:1061.

Blume et al. (2013), "Characterization of *clostridium thermocellum* isolates grown on cellulose and sugarcane bagasse", Bioenerg. Res. 6:763-775

Bugg T et al (2011) "The emerging role for bacteria in lignin degradation and bio-product formation", Current Opinion in Biotechnology, 22:394-400

Carrington, E. et al. (1998), "Review of the scientific evidence relating to the controls on the agricultural use of sewage sludge. Part—1 The evidence underlying the 1989 Department of the Environment Code of Practice for agricultural use of sludge and the Sludge (Use in Agriculture) Regulations, Report DETR 4415/3. Part 2—Evidence since 1989 relevant to controls on the agricultural use of sewage sludge, Report No. DETR 4454/4. WRc report to the Department of the Environment, Transport and the Regions, Department of Health, Ministry of Agriculture, Fisheries and Food and UK Water Industry Research Limited. ISBN 1 898920 37 0. WRc Publications, Swindon. NOTE full text is missing Chaganti, S., et al. (2012), "Impact of oleic acid on the fermentation of glucose and xylose mixtures to hydrogen and other byproducts," Renewable Energy 42:60.

Chandra R. et al (2011) "Bacterial decolorizatin of black liquer in axenic and mixed condition and characterization of metabolites", Biodegradation 22:603-611

Chandra, R., et al. (2012), "Methane production from lignocellulosic agricultural crop wastes: A review in context to second generation of biofuel production," Renewable and Sustainable Energy Reviews, 16:14621476.

Chen Y. H., Chai L. Y. (2011), "Biodegradation of kraft lignin by a bacterial strain Comamonas sp. B-) isolated from eroded bamboo slips", Journal of applied Microbiology 1364-5072

Chen and Lee (1997) "Membrane-mediated extractive fermentation for lactic acid production from cellulosic biomass", Applied Biochemistry and biotechnology 63-65: 435-448

Consonni, S., et al. (2005) "Alternative strategies for energy recovery from municipal solid waste—Part A: Mass and energy balances," Waste Management 25:123

Cysneiros, D. et al. (2011) "Temperature effects on the trophic stages of perennial rye grass anaerobic digestion," Water Science & Technology 64(1):70-76

Dahlen, L. et al. (2007). Comparison of different collection systems for sorted household waste in Sweden. Waste Management. 27, 1298-1305.

Davis et al. (2012), "Genome Sequence of amycolatopsis sp. strain ATCC 39116, a plant biomass-degrading actinomycete", Journal of Bacteriology 194(9):2396-2397

Del Borghi et al. (1999), "Hydrolysis and thermophilic anaerobic digestion of sewage sludge and organic fraction of municipal solid waste," Bioprocess Engineering 20:553-560

Delgenes, J. et al. (2000), "Investigations on the changes in anaerobic biodegradability and biotoxicity of an industrial microbial biomass induced by a thermochemical pretreatment," Water Science and Technology 41(3):137-144

Deportes, I. et al. (1998), "Microbial disinfection capacity of municipal solid waste (MSW) composting," Journal of Applied Microbiology 85:238-246

Diaz, J., et al., (2011), "Co-digestion of different waste mixtures from agro-industrial activities: Kinetic evaluation and synergistic effects," Bioresource Technology 102:10834.

Dong-Yeol Lee et al (2010) "Continuous H2 and CH4 production from high-solid food waste in the two-stage thermophilic fermentation process with the recirculation of digester sludge", Bioresource Technology 101

Dugba Prince N, Zhang Ruihong (1999) "Treatment of dairy wastewater with two-stage anaerobic sequencing batch reactor systems", Biosource Technology 68:225-233

Eida M. F et al (2012) "Isolation and characterization of cellulose-decomposing bacteria inhabiting sawdust and coffee residue composts", Microbes Environ 27(3):226-233

ENVIO Biogas Beteilingungs GmbH, 26 Aug. 2010, DE 10 2009 009 985

Fdez-Guelfo et al. (2011-A), "The use of thermochemical and biological pretreatments to enhance organic matter hydrolysis and solubilisation from organic fraction of municipal solid waste (MSW)," Chemical Engineering Journal 168:249-254

Fdez-Guelfo et al. (2011-B), "Biological pretreatment applied to industrial organic fraction of municipal solid wastes (OFMSW): Effect on anaerobic digestion," Chemical Engineering Journal 172:321-325

Fdez-Guelfo et al. (2012) "New parameters to determine the optimum pretreatment for improving the biomethanization performance," Chemical Engineering Journal 198-199:81-86

Fukuhara Y et al (2010) "Characterization of the isophthalate degradation genes of momamonas sp. strain E6" Applied and Environmental Microbiology 76(2):519

Gao et al (2008) "Rice straw fermentation using lactic acid bacteria", Bioresource technology 99:2742-2748

Ge, H. et al. (2010), "Pre-treatment mechanisms during thermophilic-mesophilic temperature phased anaerobic digestion of primary sludge," Water Research 44:123-130

Ghose, T. K. (1987), Measurement of cellulase activities. Pure & Appl. Chem., 59(2): p. 257-268

Goto et al: (2004), "Hydrothermal conversion of municipal organic waste into resources." Bioresource Technology 93:279-284.

Hansen, T. et al. (2007b). Composition of source-sorted municipal organic waste collected in Danish cities. Waste Management. 27, 510-518

Harris W. L., Dague R. R. (1993) "Comparative performance of anaerobic filters at mesophilic and thermophilic temperatures", Water Environment Research 65(6):764-771

Hartmann, H., and Ahring, B. (2006), "Strategies for the aerobic digestion of the organic fraction of municipal solid waste: an overview," Water Science & Technology 53(8):7.

Hyun-Woo Kim et al (2011) "A comparison study on the higerate co-digestion of sewage sludge and good waste using of temperature-phased anaerobic sequencing batch reactor system", Bioresource Technology 102:7272-7279

Iwaki H et al. (2011), "Tropicibacter phthalicus sp. nov., A Phthalate-Degrading bacterium from seawater", Curr. Microbiol 64:392-396

Iwaki H. et al (2012) "Isolation and characterization of marine bacteria capable of utilizing phthalate", Workd J Microbiol Biotechnol 28:1321-1325

Jensen, J. et al. (2010), "Enzymatic processing of municipal solid waste," Waste Management 30:2497-2503

Jensen, J., et al. (2011) "Cellulase hydrolysis of unsorted MSW," Appl. Biochem. Biotechnol. 165:1799-1811

Ji S et al (2012) "An untapped Bacterial cellulytic community enriched from coastal marine sediment under anaerobic and thermophilic conditions", Microbiol Lett 335:39-46

Kaiser S. K et al (1995) "Initial studies on the temperature-phased anaerobic biofilter process, Water environment research", 67(7):1095-1103

Kask, S., et al. (1999), "A study on growth characteristics and nutrient consumption of Lactobacillus plantarum in A-stat culture," Antonie van Leeuwenhoek 75:309.

Kato et al (2004), "*Clostridium* straminisolvens so, nov, a moderately thermophilic aerotolerant and cellulolytic bacterium isolated from a cellulose-degrading bacterial community", International Journal of Systematic and Evolutionary Microbiology 54:2043-2047

Kato et al (2005) "Stable Coexistence of Five Bacterial Strains as a cellulose-degrading community", Applied and environmental microbiology 71(11):7099-7106

Kim H. W et al (2004) "Anaerobic co-digestion of sewage sludge and food waste using temperature-phased anaerobic digestion process", Water Science and Technology 55(9):107-114

Kim, D., and Kim, M., (2012), "Thermophilic fermentative hydrogen production from various carbon sources by anaerobic mixed cultures," International Journal of Hydrogen Energy 37:2021.

Kornillowicz-Kowalska T., Bohacz J (2010), "Dynamics of growth and succession of bacterial and fungal communities during composting of feather waste", Bioresource Technoly 101:1268-1276

Kristensen et al. (2009), "Yield determining factors in high-solids enzymatic hydrolysis of lignocellulose," Biotechnology for Biofuels 2:11.

Kubler, H. and Schertler, C, (1994) "Three phase anaerobic digestion of organic wastes," Water Science and Technology 30(12):367-374

Kumar et al (2008) "Bioconversion of lignocellulosic biomass: biochemical and molecular perspectives", J Ind Microbiol Biotechnol 35:377-391

Lafitte-Trouque S., Forster C. F. (2000) "Dual anaerobic co-digestion of sewage sludge and confectionery waste", Bioresource Technology 71:77-82

Latorre I et al (2012) "PVC biodeterioration and DEHP leaching by DEHP-degrading bacteria", International Biodeterioration and Biodegradation 69:73-81

Lee, D. et al. (2010), "Continuous H2 and CH4 production from high solid food waste in the two-stage thermophilic fermentation process with the recirculation of digester sludge," Bioresource Technology 101:S42.

Li, A. et al. (2007) "Bioconversion of municipal solid waste to glucose for bioethanol conversion," Bioprocess. Biosyst. Eng. 30:189-196

Li, S. et al. (2012), "Production of fermentable sugars from enzymatic hydrolysis of pretreated municipal solid waste after autoclave process," Fuel 92:84-88

Liang et al (2008) "Phthalates biodegradation in the environment", Appl Microbiol Biotechnol 80:183-193

Liang et al (2010) "Genetic diversity of phthalic acid esters-degrading bacteria isolated from different geographical regions of China", Antonie van Leeuwenhoek 97:79-89

Liong, M. and Shah, N. (2005), "Optimisation of cholesterol removal, growth and fermentation patterns of *Lactobacillus acidophilus* ATCC 4862 in the presence of mannitol, fruto-oligosaccharide and inulin: a response surface methodology approach," Journal of Applied Microbiology 98:1115.

Lv, W. et al. (2010), "Putting microbes to work in sequence: Recent advances in temperature-phased anaerobic digestion processes," Bioresource Technology 101:9409

Maki et al (2012) "Newly isolated and characterized bacteria with great application potential for decomposition of lignocellulosic biomass", J Microbiol Biotechnol 22:156-66

Malkow, T. (2004) "Novel and innovative pyrolysis and gasification technologies for energy efficient and environmentally sound MSW disposal", Waste Management 24:53-79

Matthews et al (2004) "Lactic acid bacteria as a potential source of enzymes for use in vinification", Applied and environmental microbiology 70(10):5715-5731

Matthews et al (2006), "A survey of lactic acid bacteria for enzymes of interest to oenology", Australian journal of grape and wine research 12:235-244

Meyers, S. A. et al. (1996) "Lipase production by lactic acid bacteria and activity on butter oil", Food microbiology 13:383-389

Morita, M., and Sasaki, K. (2012), "Factors influencing the degradation of garbage in methanogenic bioreactors and impacts on biogas formation," Applied Microbiol. Biotechnol. 94:575-582

Muhle, S. et al. (2010). Comparison of carbon emissions associated with municipal solid waste management in Germany and the UK. Resources Conservation and Recycling. 54, 793-801

Nakasaki, K. et al. (1996) "The use of *Bacillus lichenformis* HA1 to accelerate composting of organic wastes," Compost. Sci. & Utilization 4(4):1.

Nakasaki, K. et al. (2013) "Inoculation of *Pichia kudriavzevii* RB1 degrades the organic acids present in raw compost material and accelerates compositing," Bioresource Technology 144:521

Navacharoen A., Vnagnai A. S (2011) "Biodegradation of diethyl phthalate by an organic-solvent-tolerant *bacillus subtilis* strain 3C3 and effect of phthalate ester coexistence", International Biodeterioration and Biodegradation 65:818-816

Ou, M., et al. (2011), "Lactic acid production from non-food carbohydrates by thermotolerant *Bacillus coagulans*," J. Ind. Microbiol. Biotechnol. 38:599.

Papadimitriou, E. K., (2010) "Hydrolysis of organic matter during autoclaving of commingled household waste," Waste Management 30:572.

Parajo et al (1997) "Production of lactic acid from lignocellulose in a single stage of hydrolysis and fermentation, Food Biotechnology 11(1):45-58

Park et al (2009) "Biodegradation of diisodecyl phthalate (DIDP) by *bacillus* sp. SB-007", Journal of Basic Microbiology 46:31-35

Patel, M., et al. (2005), "Simultaneous saccharification and co-fermentation of crystalline cellulose and sugar cane bagasse hemicellulose hydrolysate to lactate by thermotolerant acidophilus *Bacillus* sp." Biotechnol. Prog. 21:1453.

Riau et al (2010) "Temperature-phased anaerobic digestion (TPAD) to obtain class A biosolids: A semi-continuous study", Bioresource Technology 101:2706-2712

Riber, C. et al. (2007) Method for fractional solid-waste sampling and chemical analysis. International Journal of Environmental Analytical Chemistry 87 (5), 321-335.

Riber, C. et al. (2009), "Chemical composition of material fractions in Danish household waste," Waste Management 29:1251

Sakai et al. (2000) "Selective proliferation of lactic acid bacteria and accumulation of lactic acid during open fermentation of kitchen refuse with intermittent pH adjustment", Food Sci. Tech. 6(2):140-145

Sakai et al. (2004) "Fluorescent In Situ hybridization of open lactic acid fermentation of kitchen refuse using rRNA-targeted oligonucleotide Probes", Journal of Bioscience and Bioengineering, 98(1):58-56

Sasaki et al (2012) "Acceleration of cellulose degradation and shift of product via methanogenic co-culture of a cellulolytic bacterium with a hydrogenotrophic methanogen", Journal of Bioscience and Bioengineering 114(4):435-439

Schmidt and Padukone (1997) "Production of lactic acid from wastepaper as a cellulosic feedstock", Journal of industrial Microbiology and Biotechnology 18:10-14

Schmit Kathryn H., Ellis Timothy G (2001) "Comparison of Temperature-Phased and Two-Phase Anaerobic Co-Digestion of Primary Sludge and Municipal Solid Waste", Water Environment Research 73:314-321

Schneider, R., (2002). "Sustainable recovery of animal by-products, of which the disposal is regulated, in a pilot facility at the animal by-product recovery plant of St. Erasmus." Final report to the Bavarian Ministry for State-Development and Environmental Affairs, Germany. Project No. E79, ATZ-EVUS, Centre for Development and Process Engineering, Sulzbach-Rosenberg, Germany.

Shanwei Xu et al. (2012) "Biodegradation of specified risk material and fate of scrapie prions in compost, Journal of environmental science and health", Part A 48:26-36

Shiratori H et al (2006) "Isolation and characterization of a new *clostridium* sp. that performs effective cellulosic waste digestion in of thermophilic methanogenic bioreactor", Appl Environ Microbiol 72(5):3702-3709

Shiratori H et al (2009) "*Clostridium* clariflavum sp. nov. and *clostridium* caenicola sp. nov., moderately thermophilic cellulose-/cellobiose-digesting bacteria isolated from methanogenic sludge", International Journal of Systematic and Evolutionary Microbiology 59:1764-1770

Simmons, P. et al. (2006). The state of Garbage in America. Biocycle. 47, 26-43.

Six and Debaere (1992) "Dry anaerobic conversion of municipal solid waste by means of the Dranco process, Water Science and Technology 25(7):295-300

Sizova et al (2011), "Cellulose- and Xylan-Degrading Thermophilic Anaerobic Bacteria from Biocompost", Applied and Environmental Microbiology 77(7):2282-2291

Stehlik Petr. (2009) "Contribution to advances in waste-to-energy technologies," Journal of Cleaner Production 17:919.

Supaphol, S. et al. (2011), "Microbial community dynamics in mesophilic anaerobic co-digestion of mixed waste," Bioresource Technology 102:4021-4027

Tai et al (2004), "Isolation and characterization of a cellulytic *geobacillus thermoleovorans* T4 strain from sugar refinery wastewater", Extremophiles 8:345-349

Tonini, T., and Astrup, T. (2012) "Life-cycle assessment of a waste refinery process for enzymatic treatment of municipal solid waste," Waste Management 32:165-176

Van den Keybus (2006) WO2006/029971

Wu et al. (2010) "Complete degradation of di-n-octyl phthalate by biochemical cooperation between *Gordonia* sp-strain JDC-2 and *Arthrobacter* sp. Strain JDC-32 isolated from activated sludge", Journal of Hazardous Material 176:262-268

Wu, S., et al. (2008), "Dark fermentative hydrogen production from xylose in different bioreactors using sewage sludge microflora," Energy & Fuels 22:113

Wu et al (2011) "Isolation and characterization and characterization of four di-nbutyl phthalate (DBP)-degrading *gordonia* sp. strains and cloning the 3,4 phthalate diozygenase gene", World J Micorbiol Biotechnol 27:2611-2617

Yang et al (2001), "Bioconversion of corn straw by coupling ensiling and solid-state fermentation", Bioresource technology 78:277-280

Yoshida, H., Takavoli, O., (2004). "Sub-critical water hydrolysis treatment for waste squid entrails and production of amino acids, organic acids, and fatty acids." Journal of Chemical Engineering of Japan 37 (2), 253-260

Yu et al (2012) "Experimental and modelling study of a two-stage pilot scale high solid anaerobic digester system", Bioresource Technology 124:8-17

Zhang et al. (2007), "Extracellular enzyme activities during regulated hydrolysis of high-solid organic wastes", Water Research 41:4468-4478

Zhang, D. et al. (2010), "Municipal solid waste management in China: Status, problems and challenges," Journal of Environmental Management 91:1623.

Zverlov et al (2010) "Hydrolytic bacteria in mesophilic and thermophilic degradation of plant biomass", Eng Life Sci 10(6):528-536

The invention claimed is:

1. A method of processing Municipal Solid Waste (MSW) comprising the steps of fermenting a stream of unsorted MSW in a microbial fermentation reactor in which the unsorted MSW is fermented with an inoculated microbial consortium and with agitation at a non-water content of between 10 and 50% by weight and at a temperature of between 35 and 75 degrees C. for a period of between 1 and 72 hours, under conditions sufficient to maintain a live lactic acid bacteria concentration of at least $1.0 \times 10^{10}$ CFU/L, wherein said microbial consortium comprises live lactic acid bacteria and wherein said microbial consortium provides a microbially-derived cellulase activity of at least 30 Filter Paper Units/Liter (FPU/L), and wherein said unsorted MSW comprises a mixture of biogenic and non-biogenic material in which 15% by weight or greater of the dry weight is non-biogenic material, and removing a stream of fermented unsorted MSW from the reactor and subjecting it to a separation step whereby non-biodegradable solids are removed to provide a slurry of bio-degradable components.

2. The method of claim 1, wherein the unsorted MSW stream is inoculated with a microbial consortium of microorganisms naturally occurring in the waste, and propagated on local waste or components of local waste as a food source in fermentation conditions of temperatures within the range 37 to 55 degrees C., or 40 to 55 degrees C., or 45 to 50 degrees C., and at a pH within the range 4.2 and 6.0.

3. The method of claim 1, wherein water content has been added to the MSW in order to achieve a constant mass ratio of water between 0.5 and 2.5 kg water per kg MSW.

4. The method claim 1, wherein cellulase activity is added by inoculation with a selected microorganism that exhibits extra-cellular cellulase activity.

5. The method of claim 1, wherein the slurry of bio-degradable components is subject to post-fermentation following separation of non-degradable solids.

6. The method of claim 1, wherein inoculation of the unsorted MSW stream is provided by recycling wash waters or process solutions used to recover residual organic material from non-degradable solids and/or wherein inoculation of the unsorted MSW stream is provided before or concurrently with the addition of enzymatic activities.

7. The method of claim 6, wherein said recycled wash waters or process solutions have been enriched prior to inoculation of the microbial fermentation reactor, wherein the enriched recycled wash waters or process solutions are better able to promote bacterial growth compared to the recycled wash waters or process solutions prior to enrichment.

8. The method of claim 7, wherein said enrichment comprises incubation of the recycled wash waters or process solutions at 45° C. with continuous agitation in the presence of approximately 1% by wt yeast extract, approximately 1% by weight mixed glucose/sucrose, and approximately 1% by weight microcrystalline cellulose.

9. The method of claim 1, wherein said slurry of bio-degradable components comprises dissolved solids and wherein at least 40% by weight of the dissolved volatile solids comprises lactate and/or wherein at least 40% by weight of the non-water content of the slurry of bio-degradable components comprises dissolved volatile solids.

10. The method of claim 1, wherein the microbial fermentation is conducted within the temperature range 45-50 degrees C.

11. The method of claim 1, wherein the unsorted MSW was heated to a temperature not higher than 75 degrees C.

12. The method of claim 1, wherein the removed non-biodegradable solids comprise at least 20% of the dry weight of the MSW, and/or wherein the removed non-biodegradable solids comprise at least 20% by dry weight of recyclable materials.

13. The method of claim 1, wherein removal of the non-biodegradable solids is performed within 36 hours from the start of enzymatic hydrolysis.

14. The method of claim 1, wherein ethanol or lactate are first removed from the slurry of bio-degradable components prior to anaerobic digestion to produce biomethane.

* * * * *